US010150793B2

(12) United States Patent
Piazza et al.

(10) Patent No.: US 10,150,793 B2
(45) Date of Patent: Dec. 11, 2018

(54) ANTAGONISTS OF CB1 RECEPTOR

(75) Inventors: Pier Vincenzo Piazza, Bordeaux (FR);
Monique Vallee, Bordeaux (FR);
Giovanni Marsicano, Bordeaux (FR);
Francois-Xavier Felpin, Nantes (FR);
Luigi Bellocchio, Bordeaux (FR);
Daniela Cota, Bordeaux (FR);
Jean-Michel Revest, Bordeaux (FR);
Sergio Vitiello, Bordeaux (FR);
Umberto Spampinato, Bordeaux (FR);
Rafael Maldonado, Barcelone (ES)

(73) Assignees: INSERM (Institut National de la Santé et de la Recherche Médicale), Paris (FR); UNIVERSITE DE BORDEAUX, Bordeaux (FR)

(*) Notice: Subject to any disclaimer, the term of this patent is extended or adjusted under 35 U.S.C. 154(b) by 564 days.

(21) Appl. No.: 14/118,420

(22) PCT Filed: May 18, 2012

(86) PCT No.: PCT/EP2012/059310
§ 371 (c)(1),
(2), (4) Date: Feb. 26, 2014

(87) PCT Pub. No.: WO2012/160006
PCT Pub. Date: Nov. 29, 2012

(65) Prior Publication Data
US 2014/0200200 A1 Jul. 17, 2014

(30) Foreign Application Priority Data

May 20, 2011 (EP) ..................... 11305625

(51) Int. Cl.
*A61K 31/57* (2006.01)
*C07J 11/00* (2006.01)
*C07J 7/00* (2006.01)
*C07J 31/00* (2006.01)
*C07J 41/00* (2006.01)
*C07J 5/00* (2006.01)
*C07J 13/00* (2006.01)

(52) U.S. Cl.
CPC ............. *C07J 7/0075* (2013.01); *A61K 31/57* (2013.01); *C07J 5/0015* (2013.01); *C07J 7/0005* (2013.01); *C07J 7/007* (2013.01); *C07J 7/0015* (2013.01); *C07J 7/0045* (2013.01); *C07J 11/00* (2013.01); *C07J 13/005* (2013.01); *C07J 13/007* (2013.01); *C07J 31/006* (2013.01); *C07J 41/005* (2013.01); *C07J 41/0011* (2013.01); *C07J 41/0027* (2013.01)

(58) Field of Classification Search
CPC ....... A61K 31/57; C07J 7/0075; C07J 5/0015; C07J 7/0005; C07J 7/0015; C07J 7/0045; C07J 7/007; C07J 11/00; C07J 13/005; C07J 13/007; C07J 31/006; C07J 41/0011; C07J 41/0027; C07J 41/005
See application file for complete search history.

(56) References Cited

U.S. PATENT DOCUMENTS

| | | | |
|---|---|---|---|
| 3,084,174 A * | 4/1963 | Hoffman | C07J 5/00 540/26 |
| 3,169,133 A | 2/1965 | Ayer | |
| 3,244,696 A | 4/1966 | Mainil | |
| 3,351,639 A | 11/1967 | Allen et al. | |
| 3,361,744 A | 1/1968 | Schaub et al. | |
| 4,622,317 A | 11/1986 | Hsia et al. | |
| 4,628,052 A * | 12/1986 | Peat | A61K 31/565 514/171 |
| 4,933,157 A | 6/1990 | Counsell et al. | |
| 5,175,154 A | 12/1992 | Schwartz et al. | |
| 5,226,943 A | 7/1993 | Hulshof | |
| 5,232,917 A | 8/1993 | Bolger et al. | |
| 5,506,220 A | 4/1996 | Schwadrohn | |
| 5,763,431 A | 6/1998 | Jackson | |
| 5,968,918 A | 10/1999 | Kanda | |
| 6,455,516 B1 | 9/2002 | Backstrom et al. | |
| 7,960,553 B1 | 6/2011 | Dudley | |
| 2003/0125311 A1 | 7/2003 | Baulieu et al. | |
| 2006/0199790 A1 * | 9/2006 | Baulieu | A61K 31/57 514/175 |

(Continued)

FOREIGN PATENT DOCUMENTS

DE 972443 10/1959
DE 1166189 3/1964

(Continued)

OTHER PUBLICATIONS

Banday, A. et al., Steroid, vol. 75, Issue 12, Dec. 2010, pp. 805-809.*
Allen et al., "New Progestational Agents, Nonclassical 17-Alkylpregnene Structures," J. Med. Chem., 7:684-686 (1964) XP002681208.
Chianese et al., "Desulfohaplosamate, a new phosphate-containing steroid from *Dasychalina* sp., is a selective cannabinoid CB2 receptor ligand," Steroids, 76(10):998-1002 (2011) XP028240831.
Database CA [Online] Chemical Abstracts Service, Columbus, Ohio, US: Vitali et al., "Alkylation of steriods during Claisen rearrangement of allyl and propargyl enolethers. IV. Transposition of 20-oxo steroid enol ethers," retrieved from STN, Database accession No. 1967:28976 abstract & Gazzetta Chimica Italiana, 96(8-9), 1125-38 CODEN: GCITA9; ISSN: 0016-5603, 1966 XP002653712.

(Continued)

*Primary Examiner* — Yong S. Chong
(74) *Attorney, Agent, or Firm* — Whitham & Cook, P.C.

(57) ABSTRACT

The invention relates to an antagonist of CB1 receptor for use in the treatment of a pathologic condition or disorder selected from the group consisting of bladder and gastrointestinal disorders; inflammatory diseases; cardiovascular diseases; nephropathies; glaucoma; spasticity; cancer; osteoporosis; metabolic disorders; obesity; addiction, dependence, abuse and relapse related disorders; psychiatric and neurological disorders; neurodegenerative disorders; autoimmune hepatitis and encephalitis; pain; reproductive disorders and skin inflammatory and fibrotic diseases.

2 Claims, 11 Drawing Sheets

(56) References Cited

U.S. PATENT DOCUMENTS

Figure 1:
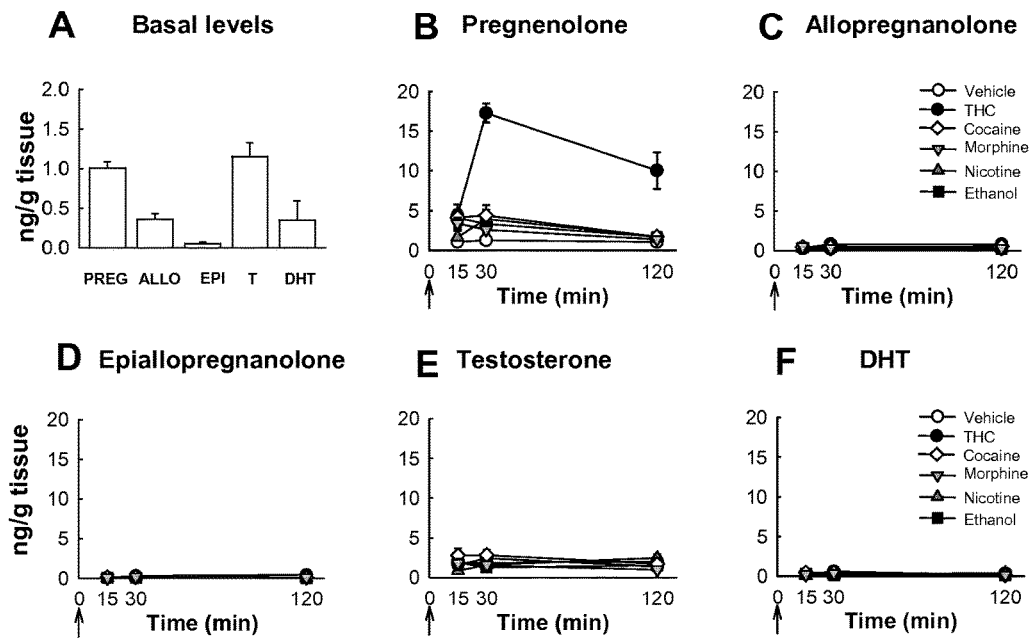

| | | |
|---|---|---|
| 2008/0015171 A1 | 1/2008 | Smith |
| 2008/0171728 A1 | 7/2008 | Bridges |
| 2009/0143347 A1 | 6/2009 | Baulieu et al. |
| 2009/0203658 A1 | 8/2009 | Marx et al. |

FOREIGN PATENT DOCUMENTS

| | | |
|---|---|---|
| EP | 1020191 | 7/2000 |
| KR | 20050023998 | 3/2005 |
| WO | 9833506 | 8/1998 |
| WO | 98/37897 | 9/1998 |
| WO | 01/22959 | 4/2001 |
| WO | 2002/036128 | 5/2002 |
| WO | 2002/072003 | 9/2002 |
| WO | 2002/089814 | 11/2002 |
| WO | 03/045362 | 6/2003 |
| WO | 2003059357 | 7/2003 |
| WO | 2004067010 | 8/2004 |
| WO | 2006/002907 | 1/2006 |
| WO | 2006037016 | 4/2006 |
| WO | 2006/077209 | 7/2006 |
| WO | 2010/107922 | 9/2010 |
| WO | 2010136000 | 12/2010 |
| WO | 2014083068 | 6/2014 |

OTHER PUBLICATIONS

De Fonseca et al., "Cannabinoid receptors in rat brain areas: Sexual differences, fluctuations during estrous cycle and changes after gonadectomy and sex steroid replacement," Life Sciences, 54(3):159-170 (1994) XP023720575.

Deghenghi et al., "New Synthesis and Structure Activity Relationship in the 17-Alkylated Progesterone Series," J. Med. Chem., 6:301-304 (1963) XP002653711.

Anaraki et al., "Modulation by female sex hormones of the cannabinoid-induced catalepsy and analgesia in ovariectomized mice," Eur. J. Pharmcol., 586(1-3):189-196 (2008) XP022671780.

Roberts, "Pregneolone—from Selye to Alzheimer and a model of the pregnenolone sulfate binding site on the GABAA receptor," Biochem. Pharmacol., 49(1):1-16 (1995) XP002681207.

Pozzi et al.; "A Mild Radical Procedure for the Reduction of B-Alkylcatecholboranes to Alkanes"; Journal of the American Chemical Society; 2005, vol. 127, No. 41, pp. 14204-14205.

Shi et al.; "OSW Saponins: Facile Synthesis toward a New Type of Structures with Potent Antitumor Activities"; Journal of Organic Chemistry; 2005, vol. 70, No. 25, pp. 10354-10367.

Banday et al.; "Studies on novel D-ring substituted steroidal pyrazolines as potential anticancer agents"; Steroids, vol. 75, Issue 12, Dec. 2010, pp. 805-809.

Pillai, G.V. et al, : "Multiple structural features of steroids mediate subtype-selective effects on human a4β3σ"—Biochemical Pharmacology 2004 vol. 68, pp. 819-831.

Li et al., "Synthesis of 3β-hydroxypregn-5-en-20-one derivatives (A, B Ring) and studies on their structure-activity relationships", English abstract enclosed, 1 page.

Luo et al. "Study on the synthesis of 3β, 21-dihydroxypregn-5-en-20-one-21-methyl ether".

Hodosan and Serban., "A new partial synthesis of Holaphyllamine", Sep. 15, 1968, 2 pages.

Autenrieth et al., "Synthesis of 3- and 6-substituted steroidal heterocycles as potential anticancer agents", Feb. 3, 1981, 5 pages.

Benedetti et al., "Improved Procedure for the Cleavage of Alkyl and Benzyl Ethers with Zinc Iodide", 1990, 2 pages.

Chen et al., "Intradermal pregnenolone sulfate attenuates caspasaicin-induced nociception in rats". Biochem. Biophys. Res. Commun., Aug. 22, 2006, 249(2):626-633.

\* cited by examiner

ANTAGONISTS OF CB1 RECEPTOR

The present application is filed pursuant to 35 U.S.C. 371 as a U.S. National Phase application of International Patent Application No. PCT/EP2012/059310, which was filed May 18, 2012, claiming the benefit of priority to European Patent Application No. 11305625.3, which was filed on May 20, 2011. The entire text of the aforementioned applications is incorporated herein by reference in its entirety.

FIELD OF THE INVENTION

The present invention relates to compounds for use in the treatment of a pathologic condition or disorder selected from the group consisting of bladder and gastrointestinal disorders; inflammatory diseases; cardiovascular diseases; nephropathies; glaucoma; spasticity; cancer; osteoporosis; metabolic disorders; obesity; addiction, dependence, abuse relapse and related disorders; psychiatric and neurological disorders; neurodegenerative disorders; autoimmune hepatitis and encephalitis; pain; reproductive disorders and skin inflammatory and fibrotic diseases.

BACKGROUND OF THE INVENTION

The CB1 receptor is one of the main G-coupled seven membrane receptor (GCPR) of the body. It is the principal GCPR of the brain and it is also expressed by most body tissues including, but not limited to, the adipose tissue, liver, pancreas, muscles, kidney, bladder and the bones.

The CB1 is activated by endogenous ligands named endocannabinoids including, but not limited to, Anandamide and 2-arachidonyl glycerol (2-AG).

Through activation by endogenous ligands, the CB1 has been involved in the regulation of a large number of physiological functions and pathological states. A non exhaustive list of the functions in which the activation of the CB1 receptor has been involved include: energy metabolism; inflammation and immunity; fibrosis, bone homeostasis; lipid storage and accumulation in various organs, behaviors; self-administration of drugs of abuse, memory, stress-related adaptation, behaviors mediated by positive reinforcers; gastrointestinal motility and motility of other visceral contractile organs; cell proliferation and differentiation; pain regulation; reproduction and fertility. (Marsicano et al., J Endocrinol Invest., 2006; 29(3 Suppl):27-46 Review; Pagotto U et al., Int J. Obes. 2006, Suppl 1:S39-43 Review; Pagotto U et al., Endocr Rev., 2006 (1):73-100. Review; Bifulco M, et al. Mol. Pharmacol. 2007, 71(6):1445-56 Review)

Because of this wide spread physiological role, over-activation of the CB1 receptor has been involved in a large number of pathologies, diseases and pathophysiological processes. A non exhaustive list of examples of diseases and diseases-related process in which the activation of the CB1 receptor has been involved include: bladder and gastrointestinal disorders; inflammatory diseases; cardiovascular diseases; nephropathies; glaucoma; spasticity; cancer; osteoporosis; metabolic disorders; obesity; addiction, dependence, abuse and relapse related disorders; psychiatric and neurological disorders; neurodegenerative disorders; autoimmune hepatitis and encephalitis; pain; reproductive disorders and skin inflammatory and fibrotic diseases. (Di Marzo et al., Nat. Rev., Drug Discov., 2004, 3: 771-784).

The CB1 receptor is the major target of Δ9tetrahydrocannabinol (THC), the active principle contained in the drugs of abuse obtained from *Cannabis sativa*. It is through CB1 activation that THC exercises its addictive effects and its behavioral and physiological disrupting effects. In addition the CB1 receptor is also involved in mediating the effects of all the other known drugs of abuse, including, but not limited to, nicotine, opioids, psychostimulants and alcohol. The CB1 receptor is also involved in mediating the appetitive properties of non-drug reinforcing stimuli that are able to induce addiction, including, but not limited to, food, sexual partners or gambling. The general effects of CB1 on drugs of abuse and other reinforcing stimuli that are able to induce addiction is explained by the excitatory control that activation of the CB1 receptor exercise on the activity of the dopaminergic transmission. Thus, activation of the dopaminergic transmission is involved in mediating the appetitive properties and addictive liability of drug of abuse and non-drug positive reinforcers. For this reason a blockade of CB1 activity has been proposed as a method for treating addiction, drug abuse, drug dependence and relapse (Scherma M et al., CNS Neurol Disord Drug Targets. 2008; 7(5):468-81. Review; Wiskerke J et al., Addict Biol. 2008; 13(2):225-38. Review; Moreira F A, et al., Addict Biol. 2008; 13(2):196-212. Review; López-Moreno J A et al, Addict. Biol. 2008; 13(2):160-87. Review; Janero D R et al., Curr Psychiatry Rep., 2007; 9(5):365-73. Review; Laviolette S R et al., Cell Mol Life Sci., 2006; 63(14):1597-613. Review; Maldonado R, et al. Trends Neurosci., 2006; 29(4):225-32. Review; Colombo G et al., Pharmacol Biochem Behav., 2005; 81(2):369-80. Review; Gardner E L. Pharmacol Biochem Behav., 2005; 81(2):263-84. Review).

Inhibition of the CB1 receptor has been shown to reduce weight and enhance improvements in cardiometabolic risk parameters. Thus, CB1 receptor antagonists have been shown to prophylactically prevent overweight, to assist in regulating food intake, to assist as a diet aid, to treat obesity and ameliorate metabolic disorders often associated with obesity such as diabetes and dislipedimia. (Bermudez-Silva F J et al., 2010; Lee H K et al. 2009; Xie S et al., 2007).

Central CB1 receptor signaling is functionally linked to monoaminergic neurotransmission. This makes CB1 antagonists candidates for the treatment of psychosis, affective and cognitive disorders brought about by disturbances in any of the central monoaminergic systems. Furthermore, CB1 agonists lead to memory impairment. CB1 antagonists are therefore good candidate agents for memory enhancement (see Reibaud M et al., Eur. J. Pharmacol, 1999; 379 (1):R1-2, and Terranova J P et al, Psychopharmacology., 1996; 126(2): 165-72). CB1 activation can also lead to impairment in movement and movement disorders like Parkinson's disease have been associated with elevated brain endocannabinoids. CB1 antagonism would therefore be a good candidate treatment for Parkinson's disease (see Di Marzo V et al, FASEB J., 2000; 14(10): 1432-8). Therefore, CB1 antagonists are candidates to treatment of various psychiatric and neurological diseases.

CB1 receptor is also involved in spasticity as disclosed by Pryce G et al., (Br J Pharmacol, 2007, 150 (4): 519-525.) and by Baker D. et al. (FASEB J., 2001, 15: 300-302).

Chien F Y, et al. have shown that WIN 55212-2, a cannabinoid agonist at the CB(1) receptor, reduces intraocular pressure in both normal and glaucomatous monkey eyes. CB1 receptors are expressed in some peripheral tissues such as nerve endings in the gastrointestinal tract depress gastrointestinal motility, mainly by inhibiting ongoing contractile transmitter release. Antagonists of CB1 receptor could thus find use in pathological states consisting of decreased intestinal motility such as Paralytic ileus caused by peritonitis, surgery, or other noxious situations (Mascolo N et al, FASEB J., 2002 December; 16(14): 1973-5).

Also about gastrointestinal diseases, CB1 receptors are also shown to be involved in liver diseases and in particular in liver steatosis, steatohepatitis (NASH) and cirrosis. The CB1 activation play a role in these diseases by a double mechanism: 1. Promoting the accumulation of fat in the liver; 2. Promoting the release of inflammatory factor such as TNFα. CB1 inhibitor are beneficial in these pathologies because they both reduce fat accumulation and the release of THFα. 3. In this case For examples see: 1. Mallat A and Lotersztajn S. *Diabetes and Metabolis* 34 (2008) 680-684; 2. Tam J et al., HEPATOLOGY 2011; 53:346-355; 3. Sören V. Siegmund S V and Schwabe R F *Am J Physiol Gastrointest Liver Physiol* 294: G357-G362, 2008; 4. DeLeve D L et al., *The American Journal of Pathology*, 173, No. 4, 2008; 5. Roche M et al., *Immunology*, 2008 125, 263-271; 6. Murumalla R et al., *Journal of Inflammation* 2011, 8:33; 7. Croci T, et al., *British Journal of Pharmacology* (2003) 140, 115-122.

CB1 receptors are also expressed in noradrenergic terminals innervating the bone. CB1 activation is able to inhibit Noradrenaline release in the bone which in turn increases osteoclaste activity decreasing bone mass, including, but not limited to menopause associated osteoporosis. For this reason CB1 antagonists have also been proposed as a treatment for osteoporosis. (Idris A I Curr Neuropharmacol. 2010 8(3):243-53.

CB1 receptors also play a role in vascular endothelial cells where they mediate the hypotensive effects of platelet and macrophage-derived endocannabinoids. CB1 antagonists would be useful agents in inhibiting endotoxin-induced or cirrhotic hypotension (see Batkai S et al, Nat. Med., 2001 July; 7(7): 827-32) both of which are characterized by elevated levels of endocannabinoids. CB1 also stimulate angiogenesis, as a consequence blockade of the CB1 receptor has been proposed for the treatment of diseases in which an increase in angiogenesis plays a pathophyisiological role as for example in tumor development.

CB1 receptors have also been involved in pathologies of the cardiovascular system including cardiomiopathies such as cyrrotic cardiomiopathy and antideoplastic drugs induced cardiomiopathies, contractile disfunction, infarction and atherosclerosis. The CB1 receptors play a role in these diseases with multiple mechanisms that involve control of blood pressure, inflammation, lipid accumulation, vascularisation and heart contractility. For example see: 1. Bákal S et al., *Am J Physiol Heart Circ Physiol*. 2007, 293: H1689-H1695; 2. Seyed Ali Gaskari S A et al., *British Journal of Pharmacology* (2005) 146, 315-323; 3. Bátkai S and Pacher P. *Pharmacol Res*. 2009, 60: 99-106. 4. Nissen S E et al., *JAMA*. 2008; 299(13): 1547-1560. 5. Mukhopadhyay P et al., *J Am Coll Cardiol*. 2007, 50: 528-536.

CB1 receptors have also been shown to be involved in inflammatory diseases and in particular but not limited to in skin diseases including skin inflammation, skin inflammation and cancer induced by UV, skin fibrosis and wound healing. In this context an inhibition or suppression of the CB1 receptor has been shown beneficial for all these pathological states. For example see: 1. Marquart S et al., ARTHRITIS & RHEUMATISM, 2010, 62:3467-3476; 2. Zheng D et al., *Cancer Res*. 2008 May 15; 68(10): 3992-3998.

Furthermore, endocannabinoid signalling is found in some human malignancies compared with the corresponding healthy tissues, as well as in human cancer cells with a high degree of invasiveness (Sarnataro D et al., 2006; Gazzerro P et al., 2010; Santoro A, et al. 2009).

The endocannabinoid signalling is also implied in fertilization, preimplantation embryo and spermatogenesis and it is therefore a relevant target to improve infertility and reproductive health in humans.

For these reasons the inhibition of the CB1 receptor has been suggested as a therapy of all these pathological states and associated diseases.

Methods aimed at blocking the activity of the CB1 through inhibition of the orthosteric binding site, the site at which the endogenous ligands bind to activate the receptor, have been developed and submitted for clinical trials. One of these compounds, rimonabant, has even been put on the market with the brand name Acomplia. Acomplia has been tested and revealed a beneficial effect for the treatment of metabolic disorders, diabetes and dyslipidemia, obesity and also in one study for nicotine addiction.

Unfortunately, available orthosteric antagonists such as rimonabant also act as inverse agonists of the CB1 receptor, i.e. they not only inhibit the activation of the CB1, but also the basal activity of the receptor in the absence of the endogenous ligand. Because of this inverse agonist action and the total inhibition of the receptor activity, available methods based on the administration of orthosteric CB1 antagonists also have a series of serious adverse effects. Because of these adverse effects commercialization of Acomplia has been suspended and the development of other methods inhibiting the orthosteric site of the CB1 stopped.

Many of the pathologies for which ortostheric antagonists of the CB1 receptor have demonstrated good therapeutic efficacy are still in need of new efficient therapies. There is consequently need to develop methods that can allow to inhibit the CB1 receptor without interfering with orthosteric binding and have less side effects than orthosteric antagonists.

Therefore, there is still a need to develop ligands that allow an inhibition of the CB1 receptors without modifying the orthosteric binding or inducing adverse effects.

SUMMARY OF THE INVENTION

The present invention relates to a compound of formula (A) or a pharmaceutical salt thereof:

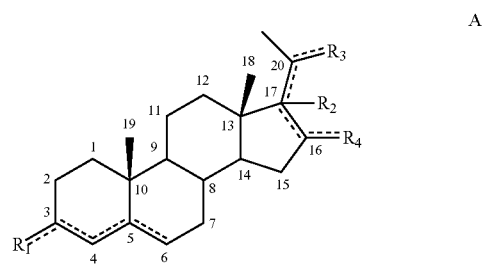

wherein:
--- denotes that the bound is a single or a double bond,
--- R1 denotes that C3 is substituted with
—H,
-halogen,
—OH,
C1-8 alkoxy,
Bn-O—

Bn- optionally substituted with C1-8 alkyl, C1-8 alkoxy, cyano, nitro, amino, carboxyl or halogen,
Ph- optionally substituted with C1-8 alkyl, C1-8 alkoxy, cyano, nitro, amino, carboxyl or halogen,
=O,
—NR5R6 wherein R5 and R6 each independently is H, C1-8 alkyl, Bn or Ph,
—O—CO—R7 wherein R7 is alkyl,
—O—CO—C$_2$H$_4$—COOH, or
—N$_3$,
—R2 denotes that C17 is substituted with
—H,
—OH,
halogen,
C1-8 alkyl,
C1-8 alkoxy,
C2-6 alkenyl,
Bn optionally substituted with C1-8 alkyl, C1-8 alkoxy, cyano, nitro, amino, carboxyl or halogen,
Ph- optionally substituted with C1-8 alkyl, C1-8 alkoxy, cyano, nitro, carboxyl or halogen, or
Bn-O—,
--- R3 denotes that C20 is substituted with
—H,
—OH,
C1-8 alkyl,
Bn,
—NR8R9 wherein R8 and R9 each independently is H, C1-8 alkyl or Bn,
=CR10R11 wherein R10 and R11 each independently is H or C1-7 alkyl, or
=O,
--- R4 denotes that C16 is substituted with
—H,
—OH, or
=O,
with the proviso that
when the bond between C16 and C17 is double, R2 is absent and the bond between C17 and C20 is single, and
when the bond between C17 and C20 is double, C20 is substituted with —H or —OH and R2 is absent,
when the bond between C4 and C5 is double, the bond between C5 and C6 is single and inversely,
for use in the treatment of a pathologic condition or disorder selected from the group consisting of bladder and gastrointestinal disorders; inflammatory diseases; cardiovascular diseases; nephropathies; glaucoma; spasticity; cancer; osteoporosis; metabolic disorders; obesity; addiction, dependence, abuse and relapse related disorders; psychiatric and neurological disorders; neurodegenerative disorders; autoimmune hepatitis and encephalitis; pain; reproductive disorders and skin inflammatory and fibrotic diseases.

The present invention also relates to a compound of formula (II)

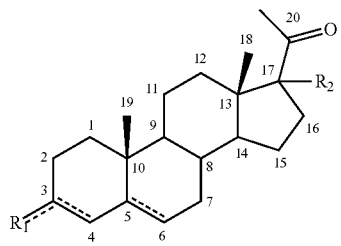

II or a pharmaceutical salt thereof, wherein:
--- denotes that the bound is a single or a double bond
--- R1 denotes that C3 is substituted with —OH, and
—R2 denotes that C17 is substituted with
C3-8 alkyl,
C2-8 alkoxy,
Bn- optionally substituted with C1-8 alkyl, C1-8 alkoxy, cyano, nitro, amino, carboxyl or halogen,
Ph- optionally substituted with C1-8 alkyl, C1-8 alkoxy, cyano, nitro, carboxyl or halogen, or
Bn-O—,
or wherein
--- R1 denotes that C3 is substituted with
C1-8 alkoxy,
Bn-O, or
Halogen, and
—R2 denotes that C17 is substituted with
C1-8 alkyl,
C2-6 alkenyl,
C1-8 alkoxy,
Bn- optionally substituted with C1-8 alkyl, C1-8 alkoxy, cyano, nitro, amino, carboxyl or halogen,
Ph- optionally substituted with C1-8 alkyl, C1-8 alkoxy, cyano, nitro, carboxyl, or halogen, or
Bn-O—.

DETAILED DESCRIPTION OF THE INVENTION

Definitions

"Agonist" refers to a compound that enhances the activity of another compound or receptor site.

The terms "Antagonist" and "Inhibitor" refer to a compound that diminishes or prevents the activity of another compound at a receptor site and more generally refer to a compound that diminishes or prevents the activation and/or the activity of a receptor.

"Treatment or treating" refers to both therapeutic treatment and prophylactic or preventive measures, wherein the object is to prevent or slow down the targeted pathologic condition or disorder. Those in need of treatment include those already with the disorder as well as those prone to have the disorder or those in whom the disorder is to be prevented. Hence, the subject to be treated herein may have been diagnosed as having the disorder or may be predisposed or susceptible to the disorder.

As used herein, the term "subject" denotes a mammal, such as a rodent, a feline, a canine, and a primate. Preferably a subject according to the invention is a human.

A "therapeutically effective amount" is intended for a minimal amount of active agent (e.g.,) which is necessary to impart therapeutic or a preventive benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

As used therein, the term "cancer" refers to or describes the physiological condition in subjects that is typically characterized by unregulated cell growth or death. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

As used therein, the terms "addiction and dependence" refers to behavioural alterations towards a reinforcing stimuli, including but not limited to pharmacological compounds, food, sexual partners, gambling, risk taking behaviors. This behavioral alteration is characterized by one or all of the following characteristics: 1. the inability of the individual to restrain from consume, intake or be in contact with the above mentioned stimuli, which results in consumptions of higher quantity of the stimuli that originally intended and unsuccessful attempts to discontinue these behaviors for prolonged periods of time; 2. a strong motivation to obtain, consume, intake or be in contact with the above mentioned stimuli which become the principal activity of the subject and that can be associated with the neglecting of other activities; 3. The appearance of a discomfort, physical or psychological, at the discontinuation of the consumption or in the absence of the reinforcing stimuli.

As used therein, the terms "abuse" refer to a physiological condition in which the integrity of the organism of an individual is permanently or transitorily impaired as a results of the consumption, intake or being in contact with reinforcing stimuli, including but not limited to, pharmacological compounds, food, sexual partners, gambling, These impairments include but are not limited to, cardiovascular complications, respiratory problems, liver diseases, infection diseases, traumatic injuries. These impairments of bodily integrity can be associated or not with the behavioral manifestations that characterize addiction and dependence as described above.

As used therein, the terms "relapse" refer to the reinstatement of addiction, dependence or abuse after a period of continuous restraint form the consumption, intake or being in contact with reinforcing stimuli, including but not limited to, pharmacological compounds, food, sexual partners, gambling.

As used therein, the terms "metabolic disorders" refer to a physiological condition in which the normal levels of chemicals used by the body as energetics or more generally as components that are necessary for guaranteeing the structural or functional integrity of the organisms are altered. These chemicals include but are not limited to: glucides, lipids, aminoacids, and electrolytes. The pathologies generally resulting from metaboic disorders include but are not limited to diabetes and dislypidemia. Metabolic disorder can also facilitate gastrointestinal and cardiovascular diseases such as atherosclerosis, NASH and cirrhosis. Metabolic disorders can be associated to obesity or be of idiopathic nature.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (Dorland's Illustrated Medical Dictionary, 28th Edition, W. B. Saunders Company, Philadelphia, Pa.). The goal of treatment of pain is to reduce the degree of severity of pain perceived by a treatment subject.

Skin inflammatory and fibrotic diseases refer to pathologies of the skin, idiopatic or induced by external agent including UV, that results in an alteration of the skin, in skin cancer and/or in a disruption of the wound healing process.

The other designation of pathologies used therein, including but not limited to, osteoporosis, neurodegenerative diseases, Parkinson, Alzheimer, schizophrenia, mood disorders, bladder and gastrointestinal disorders; inflammatory diseases; cardiovascular diseases; atherosclerosis, liver steatosis, NASH and cirrhosis nephropathies; glaucoma; spasticity; autoimmune hepatitis and encephalitis; reproductive disorders are used in within their medical inception as defined in any manual of medicine.

The expression "Ci is substituted with X" means that the carbon at position i of the chemical formula bears a substituent X, which may be an atom, such as H or an halogen, or a functional group.

"Alkyl" means monovalent linear or branched saturated hydrocarbon moiety, consisting solely of carbon and hydrogen atoms. C1-8 alkyl means a linear or branched alkyl having from one to eight carbon atoms.

"Alkoxy" means a moiety of the formula —OR, wherein R is an alkyl moiety as defined herein.

The term "halogen", refers to a fluorine, chlorine, bromine, or iodine atom.

"Amino" means a moiety of the formula —NRR' wherein R and R' each independently is hydrogen, or alkyl as defined herein.

The abbreviation Bn refers to a benzyl group.
The abbreviation Ph refers to a phenyl group.
Substituents above the plane of the molecule are shown as a solid line (⎯) and are described as β; those below the plane are shown by a broken line (⋯⋯) and are described as α.

"Optionally" means that the subsequently described event or circumstance may but need not occur, and that the description includes instances where the event or circumstance occurs and instances in which it does not.

Inhibition of CB1 Receptor

The present invention relates to a compound of formula (A) or a pharmaceutical salt thereof:

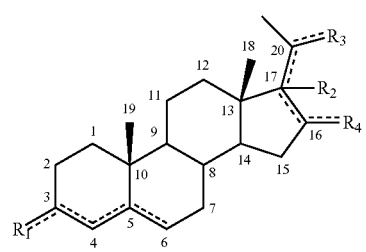

wherein:
⋯ denotes that the bound is a single or a double bond,
⋯ R1 denotes that C3 is substituted with
—H,
-halogen,
—OH,
C1-8 alkoxy,
Bn-O—
Bn- optionally substituted with C1-8 alkyl, C1-8 alkoxy, cyano, nitro, amino, carboxyl or halogen, Ph- optionally substituted with C1-8 alkyl, C1-8 alkoxy, cyano, nitro, amino, carboxyl or halogen,
=O,
—NR5R6 wherein R5 and R6 each independently is H, C1-8 alkyl, Bn or Ph,
—O—CO—R7 wherein R7 is alkyl,
—O—CO—C$_2$H$_4$—COOH, or
—N$_3$,
—R2 denotes that C17 is substituted with
—H,
—OH,
halogen,
C1-8 alkyl,
C1-8 alkoxy,
C2-6 alkenyl,
Bn optionally substituted with C1-8 alkyl, C1-8 alkoxy, cyano, nitro, amino, carboxyl or halogen,
Ph- optionally substituted with C1-8 alkyl, C1-8 alkoxy, cyano, nitro, carboxyl or halogen, or
Bn-O—,
--- R3 denotes that C20 is substituted with
—H,
—OH,
C1-8 alkyl,
Bn,
—NR8R9 wherein R8 and R9 each independently is H, C1-8 alkyl or Bn,
=CR10R11 wherein R10 and R11 each independently is H or C1-7 alkyl, or
=O,
--- R4 denotes that C16 is substituted with
—H,
—OH, or
=O,
with the proviso that
when the bond between C16 and C17 is double, R2 is absent and the bond between C17 and C20 is single, and
when the bond between C17 and C20 is double, C20 is substituted with —H or —OH and R2 is absent,
when the bond between C4 and C5 is double, the bond between C5 and C6 is single and inversely,
for use in the treatment of a pathologic condition or disorder selected from the group consisting of bladder and gastrointestinal disorders; inflammatory diseases; cardiovascular diseases; nephropathies; glaucoma; spasticity; cancer; osteoporosis; metabolic disorders; obesity; addiction, dependence, abuse and relapse related disorders; psychiatric and neurological disorders; neurodegenerative disorders; autoimmune hepatitis and encephalitis; pain; reproductive disorders and skin inflammatory and fibrotic diseases.

Indeed, the inventors have shown that pregnenolone and some of its derivatives are inhibitors of the CB1 receptor and are able to block the activation of the CB1 receptor induced by natural or synthetic agonists or endogenous ligands without modifying orthosteric binding.

Therefore, the compounds of the invention act similarly to other antagonists of CB1 receptor such as rimonabant and may be used in the treatment of pathologies wherein an antagonist of CB1 receptor is required.

Furthermore, this inhibition is an endogenous mechanism. Then, it modifies the activity of the receptor in a more physiological way modulating the response of the receptor to endogenous or exogenous agonists and not blocking the binding of the agonists to the receptor. Because of this more physiological mechanism inhibitors such as pregenolone and its derivatives are susceptible to presents less side-effect than ortostheric antagonists.

Examples of bladder and gastrointestinal disorders that may be treated with an antagonist of CB1 receptor include but are not limited to liver fibrosis; liver steatosis; non alcoholic steatohepatitis (NASH), liver cirrhosis; alcoholic steatosis; hepatic ischemic reperfusion injury complicated by endotoxaemia; acute pancreatitis; overactive and painful bladder disorders and motility alteration of contractile visceral organs.

Examples of inflammatory diseases that may be treated with an antagonist of CB1 receptor include but are not limited to inflammation and arthritis associated with obesity; chronic-immune inflammatory diseases and ulcer.

Examples of cardiovascular diseases that may be treated with an antagonist of CB1 receptor include but are not limited to cardiomiopathy such as cirrotic cardiomiopathy, anti-neoplastic drugs induced cardiomiopathy, endothelial dysfunction and cell death involved in the development of vascular dysfunction associated with congestive heart failure; hypertension; coronary artery disease; atherosclerosis; myocardial infarction; diseases resulting from lipid accumulation such as atherosclerosis, pathologies derived by increased angiogenesis and diseases involving angiogenesis.

Examples of metabolic disorders that may be treated with an antagonist of CB1 receptor include but are not limited to dyslipidemia, diabetes and diabetic complications.

Examples of addiction, dependence, abuse and relapse related disorders that may be treated with an antagonist of CB1 receptor include but are not limited to drug dependence; drug abuse; relapse in drug dependence, abuse and addiction; *cannabis* and derived products use; *cannabis* and derived products abuse; *cannabis* and derived products toxicity; *cannabis* and derived products induced psychosis.

Examples of neurodegenerative disorders that may be treated with an antagonist of CB1 receptor include but are not limited to Parkinson and Alzheimer Examples of psychiatric and neurological disorders that may be treated with an antagonist of CB1 receptor include but are not limited to schizophrenia; mood disorders; L-DOPA induced dyskinesia; memory disorders.

Examples of reproductive disorders that may be treated with an antagonist of CB1 receptor include but are not limited to infertility and recurrent abortion.

Example of skin inflammatory and fibrotic diseases that may be treated with an antagonist of CB1 receptor include but are not limited to skin inflammation, skin inflammation and cancer induced by UV, skin fibrosis and wound healing.

The invention relates to a method for the treatment of a pathologic condition or disorder selected from the group consisting of bladder and gastrointestinal disorders; inflammatory diseases; cardiovascular diseases; nephropathies; glaucoma; spasticity; cancer; osteoporosis; metabolic disorders; obesity; addiction, dependence, abuse and relapse related disorders; psychiatric and neurological disorders; neurodegenerative disorders; autoimmune hepatitis and encephalitis; pain; reproductive disorders and skin inflammatory and fibrotic diseases in a subject in need thereof comprising administering to said subject an effective amount of a compound of formula (A) or a pharmaceutical salt thereof:

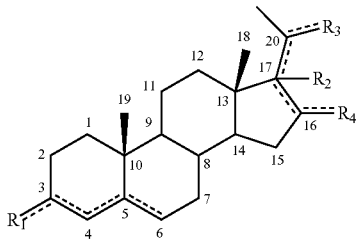

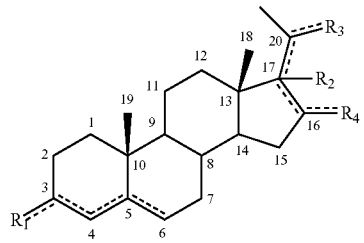

wherein:
--- denotes that the bound is a single or a double bond,
--- R1 denotes that C3 is substituted with
  —H,
  -halogen,
  —OH,
  C1-8 alkoxy,
  Bn-O—
  Bn- optionally substituted with C1-8 alkyl, C1-8 alkoxy, cyano, nitro, amino, carboxyl or halogen,
  Ph- optionally substituted with C1-8 alkyl, C1-8 alkoxy, cyano, nitro, amino, carboxyl or halogen,
  =O,
  —NR5R6 wherein R5 and R6 each independently is H, C1-8 alkyl, Bn or Ph,
  —O—CO—R7 wherein R7 is alkyl,
  —O—CO—C$_2$H$_4$—COOH, or
  —N$_3$,
—R2 denotes that C17 is substituted with
  —H,
  —OH,
  halogen,
  C1-8 alkyl,
  C1-8 alkoxy,
  C2-6 alkenyl,
  Bn optionally substituted with C1-8 alkyl, C1-8 alkoxy, cyano, nitro, amino, carboxyl or halogen,
  Ph- optionally substituted with C1-8 alkyl, C1-8 alkoxy, cyano, nitro, carboxyl or halogen, or
  Bn-O—,
--- R3 denotes that C20 is substituted with
  —H,
  —OH,
  C1-8 alkyl,
  Bn,
  —NR8R9 wherein R8 and R9 each independently is H, C1-8 alkyl or Bn,
  =CR10R11 wherein R10 and R11 each independently is H or C1-7 alkyl, or
--- R4 denotes that C16 is substituted with
  —H,
  —OH, or
  =O,
with the proviso that
  when the bond between C16 and C17 is double, R2 is absent and the bond between C17 and C20 is single, and
  when the bond between C17 and C20 is double, C20 is substituted with —H or —OH and R2 is absent,
  when the bond between C4 and C5 is double, the bond between C5 and C6 is single and inversely.
The invention relates to use of a compound of formula (A) or a pharmaceutical salt thereof:

wherein:
--- denotes that the bound is a single or a double bond,
--- R1 denotes that C3 is substituted with
  —H,
  -halogen,
  —OH,
  C1-8 alkoxy,
  Bn-O—
  Bn- optionally substituted with C1-8 alkyl, C1-8 alkoxy, cyano, nitro, amino, carboxyl or halogen,
  Ph- optionally substituted with C1-8 alkyl, C1-8 alkoxy, cyano, nitro, amino, carboxyl or halogen,
  =O,
  —NR5R6 wherein R5 and R6 each independently is H, C1-8 alkyl, Bn or Ph,
  —O—CO—R7 wherein R7 is alkyl,
  —O—CO—C$_2$H$_4$—COOH, or
  —N$_3$,
—R2 denotes that C17 is substituted with
  —H,
  —OH,
  halogen,
  C1-8 alkyl,
  C1-8 alkoxy,
  C2-6 alkenyl,
  Bn optionally substituted with C1-8 alkyl, C1-8 alkoxy, cyano, nitro, amino, carboxyl or halogen,
  Ph- optionally substituted with C1-8 alkyl, C1-8 alkoxy, cyano, nitro, carboxyl or halogen, or
  Bn-O—,
--- R3 denotes that C20 is substituted with
  —H,
  —OH,
  C1-8 alkyl,
  Bn,
  —NR8R9 wherein R8 and R9 each independently is H, C1-8 alkyl or Bn,
  =CR10R11 wherein R10 and R11 each independently is H or C1-7 alkyl, or
--- R4 denotes that C16 is substituted with
  —H,
  —OH, or
  =O,
with the proviso that
  when the bond between C16 and C17 is double, R2 is absent and the bond between C17 and C20 is single, and when the bond between C17 and C20 is double, C20 is substituted with —H or —OH and R2 is absent,
  when the bond between C4 and C5 is double, the bond between C5 and C6 is single and inversely,
for the preparation of a medicament for the treatment of a pathologic condition or disorder selected from the group consisting of bladder and gastrointestinal disorders; inflammatory diseases; cardiovascular diseases; nephropathies;

glaucoma; spasticity; cancer; osteoporosis; metabolic disorders; obesity; addiction, dependence, abuse and relapse related disorders; psychiatric and neurological disorders; neurodegenerative disorders; autoimmune hepatitis and encephalitis; pain; reproductive disorders and skin inflammatory and fibrotic diseases.

The present invention also relates to a compound of the invention, the compound being of formula (I) or a pharmaceutical salt thereof:

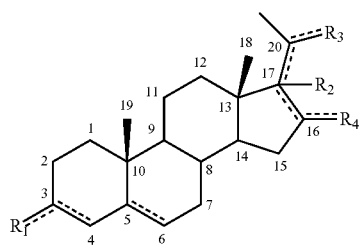

wherein:
- - - denotes that the bound is a single or a double bond,
- - - R1 denotes that C3 is substituted with
—H,
-halogen,
—OH,
C1-8 alkoxy,
Bn-O—
Bn- optionally substituted with C1-8 alkyl, C1-8 alkoxy, cyano, nitro, amino, carboxyl or halogen,
Ph- optionally substituted with C1-8 alkyl, C1-8 alkoxy, cyano, nitro, amino, carboxyl or halogen,
=O,
—NR5R6 wherein R5 and R6 each independently is H, C1-8 alkyl, Bn or Ph,
—O—CO—R7 wherein R7 is alkyl, or
—O—CO—C2H4-COOH,
—R2 denotes that C17 is substituted with
—H,
—OH,
halogen,
C1-8 alkyl,
C1-8 alkoxy,
C2-6 alkenyl,
Bn optionally substituted with C1-8 alkyl, C1-8 alkoxy, cyano, nitro, amino, carboxyl or halogen,
Ph- optionally substituted with C1-8 alkyl, C1-8 alkoxy, cyano, nitro, carboxyl or halogen, or
Bn-O—,
- - - R3 denotes that C20 is substituted with
—H,
—OH,
C1-8 alkyl,
Bn,
—NR8R9 wherein R8 and R9 each independently is H, C1-8 alkyl or Bn,
=CR10R11 wherein R10 and R11 each independently is H or C1-7 alkyl, or
=O,
- - - R4 denotes that C16 is substituted with
—H,
—OH, or
=O, with the proviso that
when the bond between C16 and C17 is double, R2 is absent and the bond between C17 and C20 is single, and
when the bond between C17 and C20 is double, C20 is substituted with —H or —OH and R2 is absent, for use in the treatment of a pathologic condition or disorder selected from the group consisting of bladder and gastrointestinal disorders; inflammatory diseases; cardiovascular diseases; nephropathies; glaucoma; spasticity; cancer; osteoporosis; metabolic disorders; obesity; addiction, dependence, abuse and relapse related disorders; psychiatric and neurological disorders; neurodegenerative disorders; autoimmune hepatitis and encephalitis; pain; and reproductive disorders and skin inflammatory and fibrotic diseases.

The invention also relates to a pharmaceutical composition comprising a compound of the invention or a pharmaceutical salts thereof and a pharmaceutically acceptable carrier.

"Pharmaceutical" or "pharmaceutically acceptable" refers to molecular entities and compositions that do not produce an adverse, allergic or other untoward reaction when administered to a mammal, especially a human, as appropriate. A pharmaceutically acceptable carrier refers to a non-toxic solid, semi-solid or liquid filler, diluent, encapsulating material or formulation auxiliary of any type.

A pharmaceutically acceptable carrier refers but without being limited to a non-toxic solid, semi-solid or liquid filler, diluent, binding agent, disintegrating agent, dissolving agent, stabilizing agent, salt forming agent, lubricating agent and encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for any route of administration including, but without being limited, oral, intravenous, intramuscular, intraarterial, intramedullary, intratechal, transdermal, topical, subcutaneous, intraperitoneal, intranasal, enteral, sublingual, vaginal and rectal.

Preferably according to the invention, the active ingredient is administered by oral route and be presented as a unit dosage form such as solid dosage form. This unit dosage form could be either tablets, coated tablets, pills, powders or granules, sachets or hard gel capsule in order to facilitate product administration to adult or children. For oral administration, in any conventional dosage form, the compositions are prepared by a classical technique with pharmaceutically acceptable excipients including, but without being limited, binding agents (e.g. pregelatinized maize starch, polyvinylpyrrolidone hydroxypropyl methylcellulose, sodium carboxymethyl cellulose, gum derivatives as guar gum, carrageenan, alginic acid or its salt, . . . ); fillers agents (e.g. lactose, saccharose, microcrystalline cellulose, calcium hydrogen phosphate, di calcium phosphate, polyol as mannitol, sorbitol or xylitol, fructose, dextrin, maltodextrin . . . ); lubricants (e.g., magnesium stearate, sodium sterayl fumarate, talc or silica); disintegrating agents (e.g potato starch or sodium starch glycollate, crospovidone, croscarmellose . . . ), salt forming agent (e.g n-methyl glucamine, sodium hydroxyde, potassium hydroxide or chlorydric acid . . . ), or wetting agents (e.g., sodium lauryl sulphate,). The tablets or hard gel capsules can be coated by methods known in the art. For example, the tablet or hard gel capsule can have an enteric or delayed-release coating which protects the active ingredient until it reaches the colon.

Another possibility is to sustain release or control release the active ingredient in order to deliver it during a long period of time (maximum 24 hours) and limit the number of administration per day. The tablets or hard gel capsules can be coated with polymer which ensure the control release of active ingredient or in the case of tablet, they can be matrixes tablet said tablets present in their composition components which ensure the control release of active ingredient; such ingredient are generally, without being limited to, hydrophilic polymers (e.g. hydroxypropylmethylcellulose, carboxymethyl cellulose sodium, xanthan gum, chitosan, polyethylene oxide . . . ) water-insoluble and hydrophobic polymers (e.g. ethylcellulose, poly(vinylacetate) cellulose acetate . . . ), fatty acids (e.g. hydrogenated vegetable oil, glyceryl palmitosterate . . . ), alcohol (e.g. cetyl alcohol, stearyl alcohol . . . ), waxes (e.g. bees'wax, carnauba wax . . . ). In the specific case of pregnenolone the sustained release formulation will also serve the function to reduce the production of downstream active metabolites of pregnenolone.

When a solid composition in tablet form is prepared, the tablet can be manufactured either by direct compression, wet granulation process or dry granulation process. The active ingredient whatever the manufacturing process used is first mixed with the entire or a part of the vehicles described above, then lubricated before being compressed into tablet.

In another embodiment the present invention could be useful for buccal delivery of active ingredient; the compositions can take the form of tablets or lozenges formulated in conventional manner. The ingredients used are the same for conventional tablet; only the proportions between ingredients change.

Preferably, the active ingredient could be delivered only for local activity; the tablets are presented as muccoadhesive tablets.

On the other hand, the active ingredient could be delivered directly in the mouth, but for systemic absorption, when water is not available, the dosage form is an orally disintegrating tablet which presents the advantage to be administered without water . . . .

In another embodiment, the present invention could be also presented as liquid preparations for oral administration. They can take the form of, for example, solutions, syrups or suspensions, or they can be presented as a dry product for constitution with water or other suitable vehicle before use. These pharmaceutical forms could be either unit dosage form as ampoule or multi dose form generally filled in vials. Such liquid preparations can be prepared by conventional techniques with pharmaceutically acceptable additives including without being limited to, suspending agents (e.g. sorbitol or manitol syrup, saccharose syrup, cellulose derivatives as sodium carboxymethyl cellulose or hydroxypropylcellulose, gum derivatives as guar gum, xanthan gum or acacia gum . . . or hydrogenated edible fats); emulsifying agents (e.g. lecithin, polysorbate, polyoxyethylated castor oil, sorbitan ester or ploxamer . . . ); aqueous and non-aqueous vehicles (e.g water, monopropylene glycol, polyethylene glycol, glycerol, sesame oil, cottonseed oil, soybean oil, castor oil, almond oil, oily esters, ethyl alcohol or fractionated vegetable oils, medium chain triglycerides . . . ); and preservatives (e.g., generally, methyl or propyl-p-hydroxybenzoates and their salts, sorbic acid and its salts, benzoic acid and its salts). The preparations can also contain buffer salts, stabilizing agent, antioxidant agent, flavouring, colouring, and sweetening agents as appropriate.

Another administration route suitable for the invention is the parenteral route. The active ingredient will be presented as an injectable product suitable for intravenous route, intramuscular route or subcutaneous route; the pharmaceutical compositions may contain vehicles which are pharmaceutically acceptable for a formulation capable of being injected. These compositions could be presented as a solution or an emulsion (for example fine emulsion, microemulsion or nanoemulsion . . . ) and may be sterile. Such composition could contain saline components (monosodium or disodium phosphate, sodium, potassium, calcium or magnesium chloride and the like or mixtures of such salts) in order to be isotonic. In some cases, when active ingredient is not sufficiently stable to be presented directly as a solution, the active ingredient is presented dry, either as a freeze-dried compositions or as powder form which upon addition, depending on the case, of sterilized non-aqueous solution suitable for injection, sterilized water or physiological saline solution, permit the constitution of injectable solutions suitable for being administered to the patient.

The final product is generally presented filled in a vial or in an ampoule form.

The doses used for the administration can be adapted as a function of various parameters, and in particular as a function of the mode of administration used, of the relevant pathology, or alternatively of the desired duration of treatment.

In order to maintain systemic drug level, and in order to avoid frequent injection, depot-type parenteral formulation could be used. These pharmaceutical forms are generally, without being limited to, in the form of microparticles, implants or a liquid that form in situ a gel or colloid or semi-solid depot after injection. Such depot formulation can be prepared by conventional techniques with pharmaceutically acceptable additives including without being limited to, biocompatible and biodegradable polymers (e.g. poly($\varepsilon$-caprolactone), poly(ethylene oxide), poly(glycolic acid), poly[(lactic acid)-co-(glycolic acid) . . . )], poly(lactic acid) . . . ), non-biodegradable polymers (e.g. ethylene vinylacetate copolymer, polyurethane, polyester(amide), polyvinyl chloride . . . ) aqueous and non-aqueous vehicles (e.g water, sesame oil, cottonseed oil, soybean oil, castor oil, almond oil, oily esters, ethyl alcohol or fractionated vegetable oils, propylene glycol, DMSO, THF, 2-pyrrolidone, N-methylpyrrolidinone, N-vinylpyrrolidinone . . . ). In the specific case of pregnenolone depot formulation will also serve the function to decrease the production of active downstream metabolite of pregnenolone.

To prepare pharmaceutical compositions, an effective amount of the compounds of the invention may be dissolved or dispersed in a pharmaceutically acceptable carrier or aqueous medium.

The liquid pharmaceutical forms suitable for injectable use include, without being limited to, sterile aqueous solutions or dispersions; or non aqueous formulations including sterile oily components such as sesame oil, peanut oil, cottonseed oil . . . , medium chain triglycerides, triacetine oil, sterile propylene glycol, sterile polyethylene glycol, sterile glycerol or sterile polyol solution.

Solutions of the active compounds as free base or pharmacologically acceptable salts can be prepared in a suitable solvent, mixed if necessary with solubilizing agent generally as surfactant, such as, without being limited to, polysorbate derivatives, polyethoxylated castor oil (cremophor RH40 for example . . . ), PEG 15 hydroxystearate (solutol HS15), poloxamer (as lutrol F68), with stabilizing agent for example EDTA and its salts, with buffering agent or with antioxidant agent (ascorbic acid and its salt, tocopherol acetate or sodium metabisulfite). Said preparation can contain preservative agent to prevent the growth of microorganisms.

For stability reason the formulation could be presented as a powder form said powder is sterile and is extemporaneously solubilized by an aqueous solvent or a non-aqueous solvent. Said preparation is generally for the extemporaneous administration of sterile injectable solutions or dispersions.

In all cases, the form must be sterile and stable under the conditions of use, manufacture and storage and must be preserved against the contaminating action of microorganisms, such as bacteria and fungi.

Compounds of the Invention

General Formulas:
The compounds of the invention have the formula:

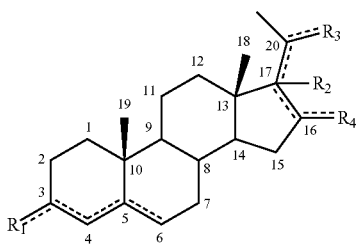

wherein:
--- denotes that the bound is a single or a double bond,
--- R1 denotes that C3 is substituted with
 —H,
 -halogen,
 —OH,
 C1-8 alkoxy,
 Bn-O—
 Bn- optionally substituted with C1-8 alkyl, C1-8 alkoxy, cyano, nitro, amino, carboxyl or halogen,
 Ph- optionally substituted with C1-8 alkyl, C1-8 alkoxy, cyano, nitro, amino, carboxyl or halogen,
 =O,
 —NR5R6 wherein R5 and R6 each independently is H, C1-8 alkyl, Bn or Ph,
 —O—CO—R7 wherein R7 is alkyl,
 —O—CO—C2H4—COOH, or
 —N3,
—R2 denotes that C17 is substituted with
 —H,
 —OH,
 halogen,
 C1-8 alkyl,
 C1-8 alkoxy,
 C2-6 alkenyl,
 Bn optionally substituted with C1-8 alkyl, C1-8 alkoxy, cyano, nitro, amino, carboxyl or halogen,
 Ph- optionally substituted with C1-8 alkyl, C1-8 alkoxy, cyano, nitro, carboxyl or halogen, or
 Bn-O—,
--- R3 denotes that C20 is substituted with
 —H,
 —OH,
 C1-8 alkyl,
 Bn,
 —NR8R9 wherein R8 and R9 each independently is H, C1-8 alkyl or Bn,
 =CR10R11 wherein R10 and R11 each independently is H or C1-7 alkyl, or
 =O,
--- R4 denotes that C16 is substituted with
 —H,
 —OH, or
 =O,
with the proviso that
 when the bond between C16 and C17 is double, R2 is absent and the bond between C17 and C20 is single, and
 when the bond between C17 and C20 is double, C20 is substituted with —H or —OH and R2 is absent,
 when the bond between C4 and C5 is double, the bond between C5 and C6 is single and inversely.

In one embodiment, the compounds of the invention have the formula (I):

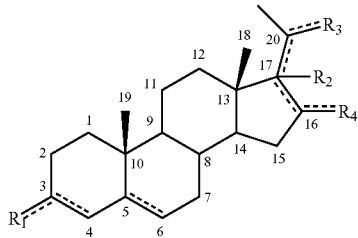

wherein:
--- denotes that the bound is a single or a double bond,
--- R1 denotes that C3 is substituted with
 —H,
 -halogen,
 —OH,
 C1-8 alkoxy,
 Bn-O—
 Bn- optionally substituted with C1-8 alkyl, C1-8 alkoxy, cyano, nitro, amino, carboxyl or halogen,
 Ph- optionally substituted with C1-8 alkyl, C1-8 alkoxy, cyano, nitro, amino, carboxyl or halogen,
 =O,
 —NR5R6 wherein R5 and R6 each independently is H, C1-8 alkyl, Bn or Ph,
 —O—CO—R7 wherein R7 is alkyl, or
 —O—CO—C2H4—COOH,
—R2 denotes that C17 is substituted with
 —H,
 —OH,
 halogen,
 C1-8 alkyl,
 C1-8 alkoxy,
 C2-6 alkenyl,
 Bn optionally substituted with C1-8 alkyl, C1-8 alkoxy, cyano, nitro, amino, carboxyl or halogen,
 Ph- optionally substituted with C1-8 alkyl, C1-8 alkoxy, cyano, nitro, carboxyl or halogen, or
 Bn-O—,
--- R3 denotes that C20 is substituted with
 —H,
 —OH,
 C1-8 alkyl, Bn, —NR8R9 wherein R8 and R9 each independently is H, C1-8 alkyl or Bn, =CR10R11 wherein R10 and R11 each independently is H or C1-7 alkyl, or

=O,

--- R4 denotes that C16 is substituted with

—H,

—OH, or

=O, with the proviso that when the bond between C16 and C17 is double, R2 is absent and the bond between C17 and C20 is single, and when the bond between C17 and C20 is double, C20 is substituted with —H or —OH and R2 is absent.

Pregnenolone:

In a particular embodiment, the compound of the invention is pregnenolone or pharmaceutical salt thereof.

Pregnenolone is a well-known steroid (CAS number 145-13-1). It is the first step of steroid synthesis in the brain and other organs.

As disclosed above, the inventors have shown that pregnenolone and its pharmaceutical salts such as pregnenolone acetate or hemisuccinate are inhibitors of CB1 receptor and then may be used in the treatment of pathologic disorders and diseases wherein an antagonist of CB1 receptor is required.

In a preferred embodiment pregnenolone is administered to a subject in a dosage such that the plasmatic concentration of pregnenolone in the subject does not exceed 100 ng/ml. Preferably, the pregnenolone is administered by sustained released formulation.

Indeed, when administered at low doses that allow pregnenolone to be in the range of effective doses (around 100 ng/ml or 100 ng/g of tissue) the conversion of pregnenolone in downstream active metabolite is diminished. Thus the inventors have shown that pregnenolone administered at low concentrations that do not induce the increase of downstream active metabolite is able to inhibit the effect of the activation of the CB1 receptor. This is a major difference and innovation compared to previous documents in which pregnenolone is administered at high dose in order to increase downstream active metabolite to which the observed therapeutic effects have been attributed. The administration of pregnenolone at low doses is advantageous because it allow to act on CB1-dependent pathologies without the unwanted and undesiderable effects due to the increase of downstream active steroids derivatives of pregnenolone that are endowed with progestative, androgenic, estrogenic, glucocorticoid activity, or neuromodulatory properties as in the case of others brain steroids derived from pregnenolone, including but not limited to allopregnanolone, Testoterone, DHEA.

Compounds with No or Low Metabolization

Alternatively, the compound of the invention is not substantially converted into active pregnenolone downstream derivatives after administration to a subject.

Pregnenolone is generally considered an inactive precursor of downstream active steroids. Active pregnenolone down stream derivatives including but not limited to pregnenolone-sulphate, allopregnanolone, DHEA, DHEA-sulfate, have been involved in the regulation of various behavioural functions.

However, the inventors have shown that inhibition of CB1 receptor is specific of pregnenolone and does not involve active downstream pregnenolone derivatives.

Using derivatives of pregnenolone that are not or not substantially converted into pregnenolone metabolites avoids side effects that may be related with metabolites whose pregnenolone is precursor and that are endowed with progestative, androgenic, estrogenic, glucocorticoid activity, or neuromodulatory properties as in the case of others brain steroids derived from pregnenolone, including but not limited to allopregnanolone, Testosterone, DHEA.

The capacity of a compound of the invention to be or not to be converted into active pregnenolone downstream derivatives may be evaluated by administering this compound, for example by injecting 50 mg/kg, to a rat, sacrificing the rat 30 min later, measuring the concentration of allopregnanolone and epiallopregnanolone in nucleus accumbens of rat by GC/MS and comparing these concentrations to allopregnanolone and epiallopregnanolone in a rat whose has been injected only a vehicle or pregnenolone.

Alternatively the compound can be administered to any cell line expressing the enzyme that metabolizes pregnenolone in culture, measuring then the content of allopregnanolone and epiallopregnanolone within the cell or on the cell culture medium by GC/MS and comparing these concentrations to allopregnanolone and epiallopregnanolone in cell cultures that have been received only a vehicle or pregnenolone In one embodiment, the compound of the invention is a compound of formula I wherein --- R1 denotes that C3 is substituted with —H, -halogen, —OH, C2-8 alkoxy, Bn-O—, Bn- optionally substituted with C1-8 alkyl, C1-8 alkoxy, cyano, nitro, amino, carboxyl or halogen, Ph- optionally substituted with C1-8 alkyl, C1-8 alkoxy, cyano, nitro, amino, carboxyl or halogen,

=O,

—NR5R6 wherein R5 and R6 each independently is H, C1-8 alkyl, Bn or Ph,

—O—CO—R7 wherein R7 is alkyl, or

—O—CO—C2H4—COOH and —R2, --- R3, --- R4 are as defined previously.

The inventors have tested a wide range of derivatives of pregnenolone to find derivatives of pregnenolone that were not substantially converted into active pregnenolone downstream derivatives after administration to a subject as they keep an inhibitor activity on CB1.

Several of group of derivatives have been found:

Bonds Between C16 and C17 and C17 and C20 are Single Bonds.

In one embodiment, the bond between C16 and C17 and the bond between C17 and C20 are single bonds.

Bond Between C4 and C5 is a Double Bond.

In one embodiment, the bonds between C3 and C4 and C5 and C6 are single bonds and the bond between C4 and C5 is double.

In this embodiment, the compound of the invention has the formula B:

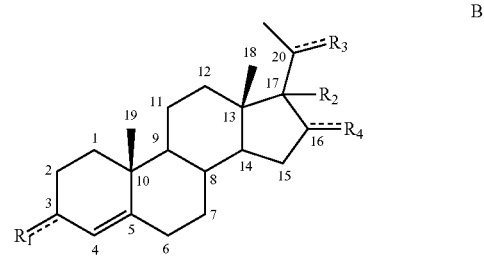

B wherein:
- R1 denotes that C3 is substituted with —OH or =O,
- R2 denotes that C17 is substituted with —H, —OH, C1-8 alkyl, halogen or Bn,
- R3 denotes that C20 is substituted with —OH or =O,
- R4 denotes that C16 is substituted with —H.

Indeed, the inventors have found that derivatives of pregnenolone with a double bond between C4 and C5 and substituted in R1, R2 and/or R3 as disclosed above were not metabolized in down-stream derivatives of pregnenolone.

Preferably, the compound is selected from the group consisting of 4-pregnen-17α,20α-diol-3-one, 4-pregnen-3β,20α-diol, 4-pregnen-20α-ol-3-one, 17α-methylprogesterone and 17α-benzylprogesterone.

Bonds Between C5 and C6 and Between C4 and C5 are Single Bonds

In one embodiment, the bonds between C3 and C4, C5 and C6 and between C4 and C5 are single bonds.

In this embodiment, the compound of this invention has the formula (C)

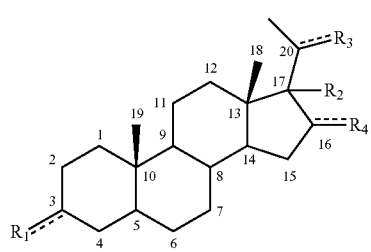

C wherein:
- R1 denotes that C3 is substituted with =O or —OH
- R2 denotes that C17 is substituted with —H
- R3 denotes that C20 is substituted with =O, and
- R4 denotes that C16 is substituted with —H.

Preferably, said compound is 5β-pregnan-3,20-dione or 5β-pregnan-3β-ol-20-one

Bond Between C5 and C6 is a Double Bond

In one embodiment, the bonds between C3 and C4 and C4 and C5 are single and the bond between C5 and C6 is double bond.

In this embodiment, the compound of the invention has the formula (D):

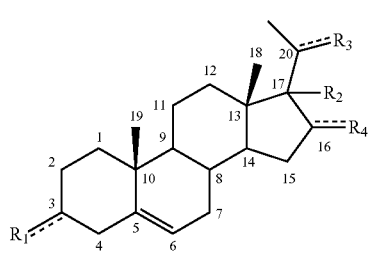

D

In this embodiment, the compound of the invention is preferably a pregnenolone modified at C3, C17 and/or C20.

Modification at C3:

In one embodiment, the compound is a pregnenolone modified at C3.

In this embodiment, the compound has the formula (D) and
- R1 denotes that C3 is substituted with
    —H, -halogen, C1-8 alkoxy, Bn-O—,
    Bn- optionally substituted with C1-8 alkyl, C1-8 alkoxy, cyano, nitro, amino, carboxyl or halogen,
    Ph- optionally substituted with C1-8 alkyl, C1-8 alkoxy, cyano, nitro, amino, carboxyl or halogen,
    =O,
    —NR5R6 wherein R5 and R6 each independently is H, C1-8 alkyl, Bn or Ph,
    —O—CO—R7 wherein R7 is alkyl, or
    —O—CO—C$_2$H$_4$—COOH,
- R2 denotes that C17 is substituted with —H
- R3 denotes that C20 is substituted with =O, and
- R4 denotes that C16 is substituted with —H.

Also, in this embodiment, the compound has the formula (D) and
- R1 denotes that C3 is substituted with
    Halogen, Bn-O or, —N$_3$,
- R2 denotes that C17 is substituted with —H,
- R3 denotes that C20 is substituted with =O, and
- R4 denotes that C16 is substituted with —H.

Preferably, the compound of this embodiment is selected from the group consisting of 3β-benzyloxypregnenolone, 3-azidopregnenolone, and 3β-fluoropregnenolone.

Modification at C3 and C17:

In one embodiment, the compound of the invention is a pregnenolone modified at C3 and at C17.

In this embodiment, the compound has the formula (D) and
- R1 denotes that C3 is substituted with C1-8 alkoxy, halogen, Bn-O— or N$_3$
- R2 denotes that C17 is substituted with Bn, —CH$_3$ or C2-6 alkenyl,
- R3 denotes that C20 is substituted with =O, and
- R4 denotes that C16 is substituted with —H.

Preferably, the compound of this embodiment is selected from the group consisting of 3β-fluoro-17α-methylpregnenolone, 17α-benzyl-3β-fluoropregnenolone, 17α-benzyl-3β-benzyloxypregnenolone and 3β-benzyloxy-17α-methylpregnenolone.

Modification at C17:

In one embodiment, the compound is a pregnenolone modified at C17 only.

In this embodiment, the compound has the formula (D) and:
- R1 denotes that C3 is substituted with —OH
- R2 denotes that C17 is substituted with
    —OH, halogen, C1-8 alkyl, C1-8 alkoxy, C2-6 alkenyl,
    Bn- optionally substituted with C1-8 alkyl, C1-8 alkoxy, cyano, nitro, amino, carboxyl or halogen,
    Ph- optionally substituted with C1-8 alkyl, C1-8 alkoxy, cyano, nitro, carboxyl or halogen, or
    Bn-O—,
- R3 denotes that C20 is substituted with =O, and
- R4 denotes that C16 is substituted with —H.

Preferably, —R2 denotes that C17 is substituted with C1-8 alkyl, C1-8 alkoxy or Bn-.

More preferably, said compound is selected from the group consisting of 17α-methylpregnenolone, 17α-benzylpregnenolone, 17-methoxypregnenolone and 17α-ethylpregnenolone.

Modification at C3 and/or C17

The present invention also relates to a compound of formula (II)

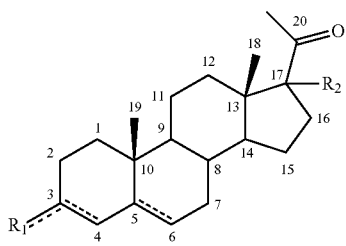

II or a pharmaceutical salt thereof, wherein:
--- denotes that the bound is a single or a double bond,
--- R1 denotes that C3 is substituted with —OH, and
—R2 denotes that C17 is substituted with
  C3-8 alkyl,
  C2-8 alkoxy,
  Bn- optionally substituted with C1-8 alkyl, C1-8 alkoxy, cyano, nitro, amino, carboxyl or halogen,
  Ph- optionally substituted with C1-8 alkyl, C1-8 alkoxy, cyano, nitro, carboxyl or halogen, or
  Bn-O—,
or wherein
--- R1 denotes that C3 is substituted with
  C1-8 alkoxy,
  Bn-O, or
  Halogen, and
—R2 denotes that C17 is substituted with
  C1-8 alkyl,
  C2-6 alkenyl,
  C1-8 alkoxy,
  Bn- optionally substituted with C1-8 alkyl, C1-8 alkoxy, cyano, nitro, amino, carboxyl or halogen,
  Ph- optionally substituted with C1-8 alkyl, C1-8 alkoxy, cyano, nitro, carboxyl, or halogen, or
Bn-O—.

Preferably, the compound of formula II is selected from the group consisting of 3(3β-fluoro-17α-methylpregnenolone, 17α-benzyl-3β-fluoropregnenolone, 17α-benzyl-3β-benzyloxypregnenolone, 3β-benzyloxy-17α-methylpregnenolone, 17α-benzylpregnenolone 3β-methoxy-17α-methylpregnenolone, 17α-allyl-3β-methoxypregnenolone, and 17α-benzyl-3β-methoxypregnenolone The invention also relates to a pharmaceutically composition comprising a compound of formula II or a pharmaceutically salts thereof and a pharmaceutically acceptable carrier.

Modification at C20:
In one embodiment, the compound is a pregnenolone modified at C20.

In this embodiment, the compound has the formula D, wherein:
--- R1 denotes that C3 is substituted with —OH,
—R2 denotes that C17 is substituted with —H,
--- R3 denotes that C20 is substituted with
  —H, —OH and C1-8 alkyl, Bn,
  —NR8R9 wherein R8 and R9 each independently is H, C1-8 alkyl or Bn,
  =CR10R11 wherein R10 and R11 each independently is H or C1-7 alkyl, or
  =O, and
--- R4 denotes that C16 is substituted with —H.
Preferably, --- R3 denotes that C20 is substituted with —H, —OH or —NR8R9 wherein R8 and R9 each independently is H or C1-8 alkyl.

More preferably, said compound is selected from the group consisting of 5-pregnen-3β,20α-diol, 20-deoxypregnenolone and 20-methylamino-5-pregnen-3β-ol.

Modification at C20 and C16:
In one embodiment the compound is a pregnenolone modified at C20 and/or at C16.

In this embodiment, the compound has the formula D wherein
--- R1 denotes that C3 is substituted with —OH,
—R2 denotes that C17 is substituted with —H,
--- R3 denotes that C20 is substituted with —OH or —H, and
--- R4 denotes that C16 is substituted with —OH or =O. Bond Between C16 and C17 is a Double Bond and the Bond C17 and C20 is a Single Bond.

In another embodiment, the bond between C16 and C17 is a double bond and the bond between C17 and C20 is a single bond and --- R1 denotes that C3 is substituted with —H, —OH or =O, --- R3 denotes that C20 is substituted with —H, —OH or =O, and --- R4 denotes that C16 is substituted with —H.

This embodiment is disclosed in the formula E below.

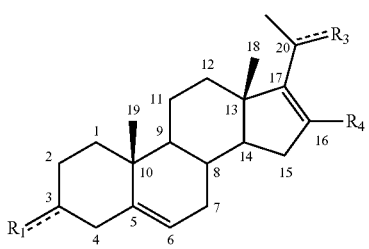

E

Preferably, said compound is 5,16 pregnadiene-20-one.
R1 is in β Position:
In the most preferred embodiment, when the bonds between C3 and R1 and C3 and C4 are single, R1 is in β position.

Indeed, the inventors have shown that contrary to the derivatives with R1 in α position, the derivatives with R1 in β position have no effect on GABA and glutamate receptors and avoid the side effects induced by modifications of these receptors, as for example but not limited to sedation, memory impairments, motor agitations. Further, the derivatives with C3 in β position keep their inhibitor activity of CB1 receptor.

Treatment of Pathologic Conditions or Disorders

The present invention also relates to a compound of the invention as defined above or a pharmaceutical salt thereof for use in a method of treatment.

In one embodiment, the compounds of formula II as defined above or a pharmaceutical salt thereof is for use in a method of treatment.

The present invention also relates to a compound of the invention as defined above or a pharmaceutical salt thereof is for the preparation of a medicament.

In one embodiment, the compounds of formula II as disclosed above or a pharmaceutical salt thereof is for the preparation of a medicament.

The present invention also relates to a method for the treatment of a pathologic condition or disorder in a subject in need thereof comprising administering to said subject an effective amount of a compound of the invention as defined above or a pharmaceutical salt thereof.

The present invention also relates to a compound of the invention as defined above or a pharmaceutical salt thereof for use in the treatment of a pathologic condition or disorder selected from the group consisting of bladder and gastrointestinal disorders; inflammatory diseases; cardiovascular diseases; nephropathies; glaucoma; spasticity; cancer; osteoporosis; metabolic disorders; obesity; addiction, dependence, abuse and relapse related disorders; psychiatric and neurological disorders; neurodegenerative disorders; autoimmune hepatitis and encephalitis; pain; reproductive disorders; and skin inflammatory and fibrotic diseases.

The invention relates to a method for the treatment of a pathologic condition or disorder selected from the group consisting of bladder and gastrointestinal disorders; inflammatory diseases; cardiovascular diseases; nephropathies; glaucoma; spasticity; cancer; osteoporosis; metabolic disorders; obesity; addiction, dependence, abuse and relapse related disorders; psychiatric and neurological disorders; neurodegenerative disorders; autoimmune hepatitis and encephalitis; pain; reproductive disorder; skin inflammatory and fibrotic diseases in a subject in need thereof comprising administering to said subject an effective amount of a compound of the invention as defined above or a pharmaceutical salt thereof.

The invention relates to use of a compound of the invention as defined above for the preparation of a medicament for treatment of a pathologic condition or disorder selected from the group consisting of bladder and gastrointestinal disorders; inflammatory diseases; cardiovascular diseases; nephropathies; glaucoma; spasticity; cancer; osteoporosis; metabolic disorders; obesity; addiction, dependence, abuse and relapse related disorders; psychiatric and neurological disorders; neurodegenerative disorders; autoimmune hepatitis and encephalitis; pain; skin inflammatory and fibrotic diseases.

Gastrointestinal Diseases:

In a preferred embodiment, the compound of the invention is for use in the treatment of gastrointestinal diseases.

In a preferred embodiment, the use of a compound of the invention is for the preparation of a medicament for treatment of gastrointestinal diseases.

In a preferred embodiment, the method is for the treatment of gastrointestinal diseases in a subject in need thereof comprising administering to said subject an effective amount of a compound.

Preferably, the compound of the invention is for use in the treatment of a liver disease, in particular non alcoholic liver steatohepatitis (NASH) and cirrosis.

Indeed, the inventors have shown that pregnenolone and it derivatives inhibit lipid accumulation in a model of obesity, and the production of TNFα.

Obesity or Metabolic Disorders:

In a preferred embodiment, the compound of the invention is for use in the treatment of obesity or metabolic disorders.

In a preferred embodiment, the use of a compound of the invention is for the preparation of a medicament for treatment of obesity or metabolic.

In a preferred embodiment, the method is for the treatment of obesity or metabolic disorders, in a subject in need thereof comprising administering to said subject an effective amount of a compound.

Preferably, the compound of the invention is for use in the treatment of diabetes and dislipidemia.

Indeed, the inventors have shown that pregnenolone and it derivatives inhibit acute food-intake, fat accumulation in a model of obesity, and the production of TNFα.

Addiction, Dependence Abuse and Relapse Related Disorders:

In another preferred embodiment, the compound of the invention is for use in the treatment of addiction, dependence abuse and relapse related disorders.

In a preferred embodiment, the use of a compound of the invention is for the preparation of a medicament for treatment of addiction, dependence abuse and relapse related disorders.

In another preferred embodiment, the method is for the treatment of addiction, dependence, abuse and relapse related disorders in a subject in need thereof comprising administering to said subject an effective amount of a compound.

Preferably, the compound of the invention is for use in the treatment of *cannabis* addiction, dependence, abuse, intoxication and relapse related disorders.

Indeed, the inventors have shown that, in particular, pregnenolone and it derivatives inhibit the endocannabinoid tetrad induced by activation of the CB1 receptor by THC; THC-induced food-intake; THC-induced memory impairements; THC-induced alteration of synaptic transmission; Sel-administration of CB1 agonists.

Preferably, the compound of the invention is also for use in the treatment of alcohol addiction, dependence abuse and relapse related disorders.

Neurodegenerative and Psychiatric Disorders:

In another preferred embodiment, the compound of the invention is for use in the treatment of neurodegenerative and psychiatric disorders.

In another preferred embodiment, the use of a compound of the invention is for the preparation of a medicament for treatment of neurodegenerative and psychiatric disorders.

In another preferred embodiment, the method is for the treatment of neurodegenerative and psychiatric in a subject in need thereof comprising administering to said subject an effective amount of a compound.

Preferably, the compound of the invention is for use in the treatment of Parkinson disease and schizophrenia.

Thus the inventors have shown that pregnenolone is able to modulate the activity of the dopaminergic system increased either by THC or cocaine and the effects of CB1 activation on excitatory synaptic transmission.

Skin Inflammatory and Fibrotic Diseases:

In another preferred embodiment, the compound of the invention is for use in the treatment of skin inflammatory and fibrotic diseases.

In another preferred embodiment, the use of a compound of the invention is for the preparation of a medicament for treatment of skin inflammatory and fibrotic diseases.

In another preferred embodiment, the method is for the treatment of skin inflammatory and fibrotic diseases. Thus the inventors have shown that compounds of the invention inhibit the production of TNFα.

Preferably, the compound of the invention is for use in the treatment of skin inflammation, skin inflammation and cancer induced by UV, skin fibrosis and wound healing.

Cardiovascular Diseases:

In another preferred embodiment, the compound of the invention is for use in the treatment of cardiovascular diseases.

In another preferred embodiment, the use of a compound of the invention is for the preparation of a medicament for treatment of cardiovascular diseases.

In another preferred embodiment, the method is for the treatment of cardiovascular diseases.

Thus the inventors have shown that compounds of the invention decrease lipid accumulation and inhibit the production of TNFα.

Preferably, the compound of the invention is for use in the treatment of cardiomyopathy.

More preferably, the compound of the invention is for use in the treatment of cardiomyopathy selected from the group consisting of cyrrotic cardiomiopathy and antideoplastic drugs induced cardiomiopathies, contractile disfunction, infarction and atherosclerosis.

The invention will be further illustrated by the following figures and examples. However, these examples and figures should not be interpreted in any way as limiting the scope of the present invention.

FIGURES

FIG. 1 shows diagrams depicting in Wistar rats: (A) Basal levels of pregnenolone PREG), allopregnanolone (ALLO), epiallopregnanolone (EPI), testosterone (T) and dihydrotestosterone (DHT) in the nucleus accumbens. (B) The effects of the injection of THC (3 mg/kg, ip), which induces a high and long-lasting increase of pregnenolone concentrations in the nucleus accumbens. The effects of other drugs of abuse: cocaine (20 mg/kg, ip), morphine (2 mg/kg, ip) nicotine (0.4 mg/kg, ip) and ethanol (1 g/kg, ip), which induce a much smaller increase in pregnenolone in the nucleus accumbens. The effects of THC and other drugs of abuse on pregnenolone-derived downstream steroids: allopregnanolone (C), epiallopregnanolone (D), testosterone (E) and DHT (F), which were largely lower than the one observed for pregnenolone. Arrows indicate the time of injection of all drugs. Data are expressed as mean±SEM (n=6-8 per group).

Figure 2:
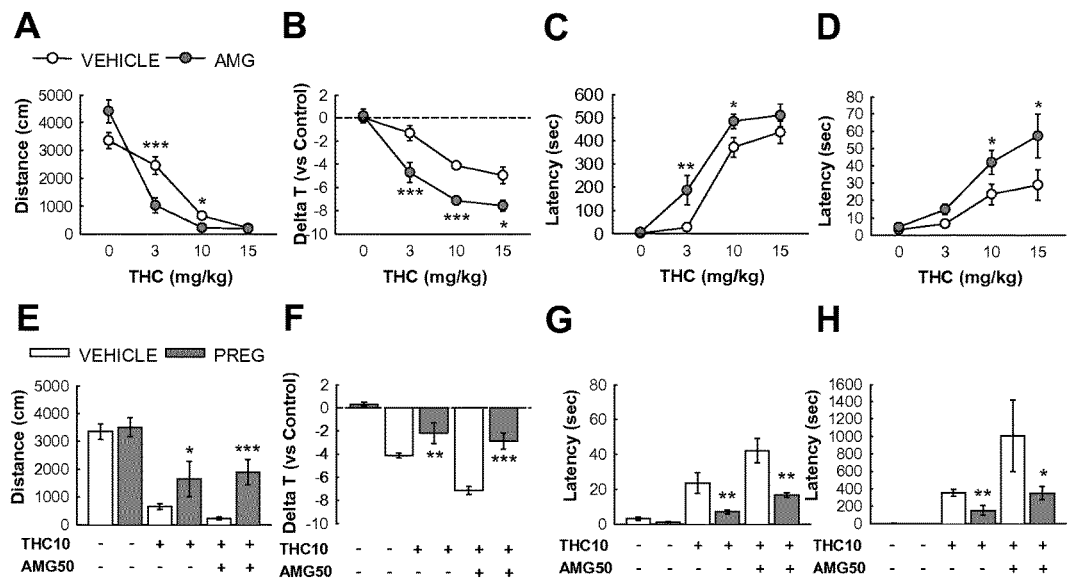

FIG. 2 shows diagrams depicting the negative regulation of pregnenolone on the THC-induced behavioural tetrad in C57B1/6 mice. THC dose-dependently (Vehicle group) decreased (A) locomotor activity $[F(3,59)=17.7, P<0.001]$ and (B) body temperature (delta T compared to control) $[F(3,59)=39.9, P<0.001]$ and increased (C) catalepsy (latency to initiate movement) $[F(3,59)=47.5, P<0.001]$ and (D) analgesia (latency to initiate a nociceptive response in the hot plate test) $[F(3,59)=5.15, P<0.01]$. The P450scc inhibitor, aminoglutethimide (AMG, 50 mg/kg, ip), which block the synthesis of pregnenolone, amplified all the behavioural effects of THC: (A) hypolocomotion $[F(3,98)=13.8, P<0.001]$, (B) hypothermia $[F(3,98)=4.7, P<0.01]$, (C) catalepsy $[F(3,98)=2.1, P<0.05]$, and (D) analgesia $[F(3,98)=2.2, P<0.05]$. Pregnenolone (PREG, 6 mg/kg, sc) reduced the effects of THC (10 mg/kg, ip) and completely rescued the effect of AMG (50 mg/kg, ip) on: (E) locomotion, (F) body temperature, (G) catalepsy and (H) analgesia. Pregnenolone had no effects in animals that did not receive THC. Data are expressed as mean±SEM (n=6-12 per group). *=P<0.05; , P<0.01; *=P<0.001 compared to vehicle-treated mice.

Figure 3:
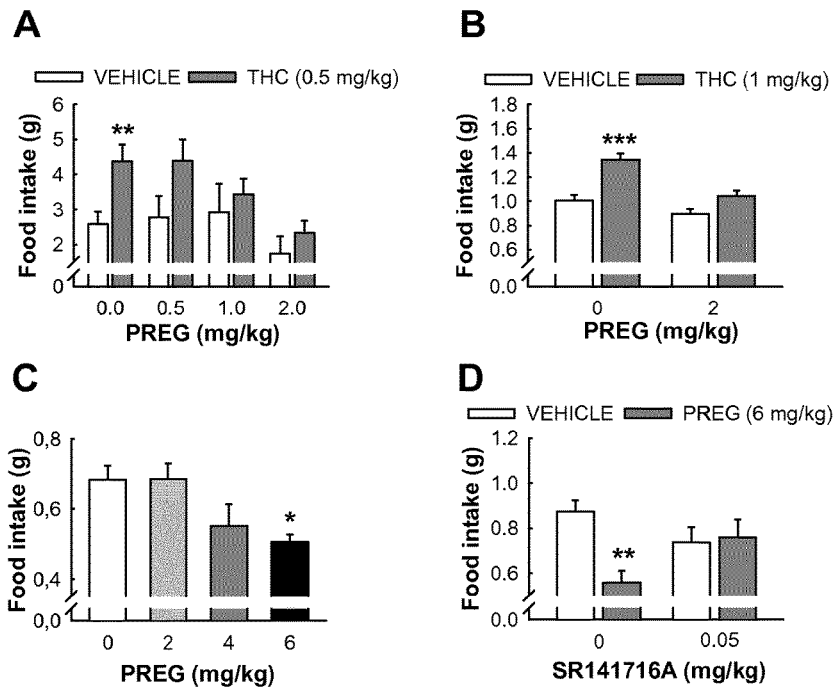

FIG. 3 shows diagrams depicting the inhibition by Pregnenolone of CB1-mediated food intake. (A) The increase in food intake induced by THC (0.5 mg/kg, ip) in ad-libitum fed Wistar rats was dose-dependently inhibited by pregnenolone injections $[F(3,94)=3.65; P<0.02]$. (B) The increase in food intake induced by THC (1 mg/kg, ip) in 24 h-food deprived C57B1/6 mice was suppressed by pregnenolone (2 mg/kg, sc). (C) Pregnenolone dose-dependently reduced food intake in 24 h-food deprived C57B1/6 mice. (D) The decrease in food intake induced by pregnenolone (PREG 6 mg/kg) in 24 h-food deprived C57B1/6 mice was reversed by a pre-treatment with the CB1R antagonist, SR141716A (0.05 mg/kg, ip). Data are expressed as mean±SEM (n=6-12 per group). *=P<0.05; , P<0.01; *=P<0.001 compared to vehicle treated animals.

Figure 4:
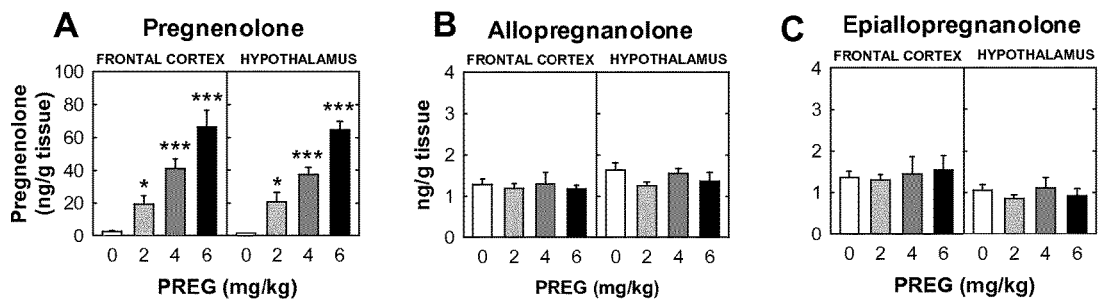

FIG. 4 shows diagrams depicting the effects of pregnenolone injections on pregnenolone-derived downstream active steroids in the brain. (A) Pregnenolone administration (s.c.) dose-dependently increased pregnenolone levels in frontal cortex and hypothalamus $[F(3,19)=20, P<0001; F(3,19)=23, P<0.001$, respectively] of 24 h-food deprived C57B1/6 mice. Pregnenolone did not modify concentrations of: (B) allopregnanolone, (C) epiallopregnanolone. Data are expressed as mean±SEM (n=7-8 per group). *=P<0.05, ***=P<0.001 compared to vehicle-treated animals (PREG 0 mg/kg).

Figure 5:
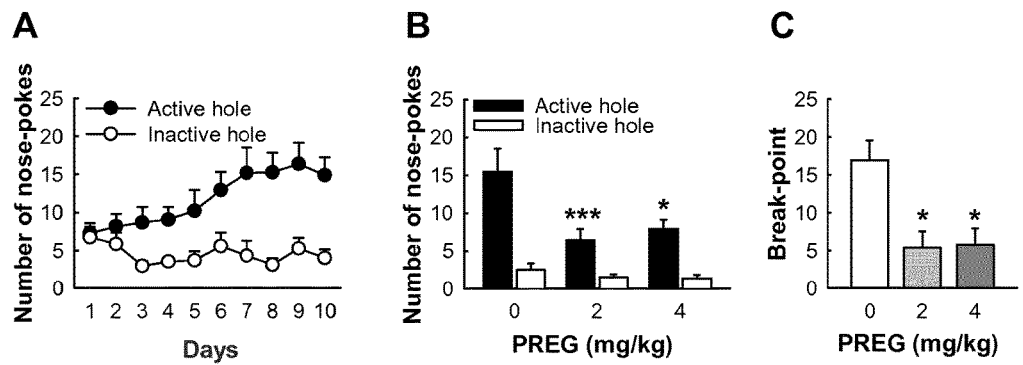

FIG. 5 shows diagrams depicting the inhibition by pregnenolone of the self-administration of the CB1 agonist WIN 55, 512-2 in CD1 mice. (A) During the acquisition of WIN 55, 512-2 self-administration (0.0125 mg/kg/infusion) the number of nose-pokes was significantly higher in the active hole than in the inactive hole $[F(1,18)=38.3, P<0.001]$. (B) After acquisition, the injection of pregnenolone (2 or 4 mg/kg, sc) decreased the number of responses in the active hole. (C) Pregnenolone also decreased the motivation for WIN 55, 512-2 as measured by the reduction in the breakpoint in a progressive ratio schedule. Data are expressed as mean±SEM (n=5-8 per group). , P<0.05, *, P<0.001 compared to vehicle-treated animals (PREG 0 mg/kg).

Figure 6:
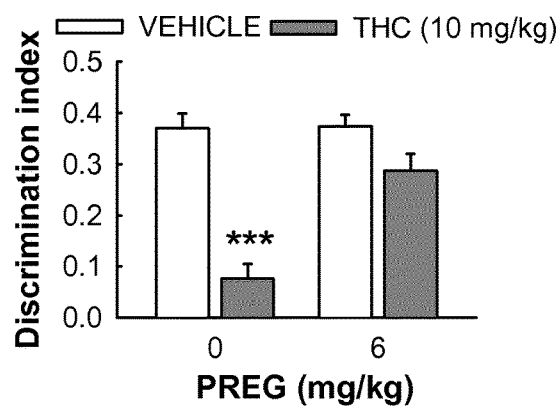

FIG. 6 shows diagrams depicting the inhibition by pregnenolone of the adverse effects of THC on memory. As indicated by the discrimination index in the object recognition test, THC (10 mg/kg, ip) induced a significant amnesia, which was abolished by pregnenolone (PREG, 6 mg/kg, sc) $[F(3,23)=24.6, P<0.001]$. Data are expressed as mean±SEM (n=6-7 per group). ***=P<0.001 compared to vehicle-treated mice.

Figure 7:
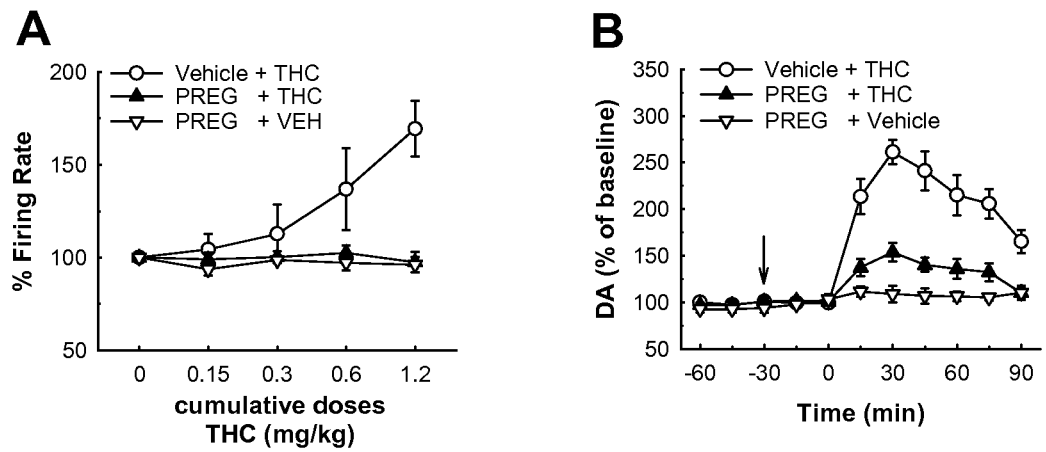

FIG. 7 shows diagrams depicting the inhibition by pregnenolone of the increase in dopaminergic activity induced by THC. Pregnenolone injection (PREG, 2 mg/kg, sc) in rats decreased $\Delta^9$-tetrahydrocannabinol (THC)-induced increase in (A) the firing rate of ventral tegmental area (VTA) dopaminergic neurons $[F(4,32)=7.14, p<0.001]$ and (B) the increase in dopamine outflow in the nucleus accumbens $[F(10,80)=10.80, p<0.001]$. Cumulative doses of THC (from 0.15 to 1.2 mg/kg) were administered i.v. at time 0 over 4 min (1 min recording per dose).

Figure 8:
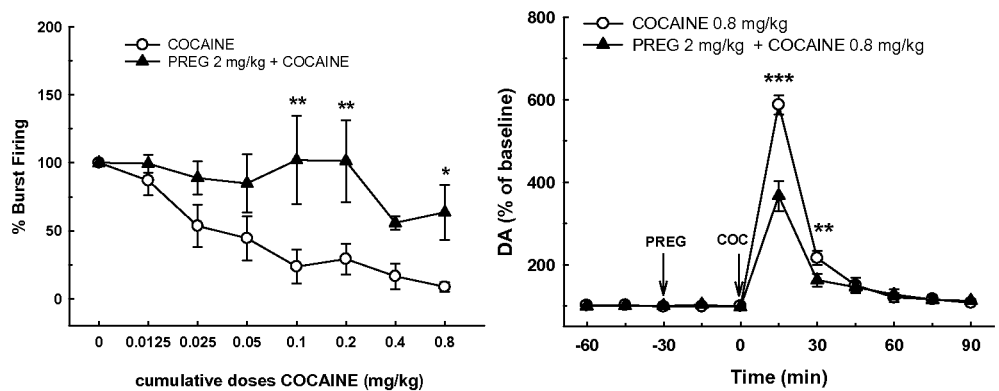

FIG. 8 Show diagrams depicting the inhibition by pregnenolone of the modification in dopaminergic activity induced by cocaine Pregnenolone injection (PREG, 2 mg/kg, sc) in rats abolished cocaine-induced decrease in (A) the bursting activity of dopaminergic neurons and the increase in dopamine outflow in the nucleus accumbens. Cumulative doses of cocaine (from 0.0125 to 0.8 mg/kg) were administered i.v. at time 0 over 4 min (1 min recording per dose). *=P<0.05=P<0.01*=P<0.001 compared to vehicle-treated rats.

Figure 9:
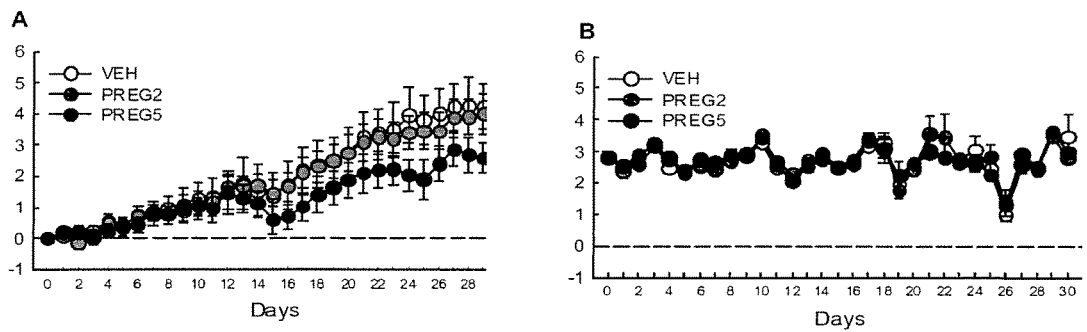

FIG. 9 shows diagrams depicting the effects of pregnenolone administration on body weight and food intake. (A) Pregnenolone 5 mg/kg (PREG5) injected subcutaneously once a day before the beginning of the dark phase progressively induced a significant decrease in body weight $[F(1,29)=3.13; p<0.001]$ in animals fed with a high fat diet. (B) However, pregnenolone did not modify food-intake.

Figure 10:
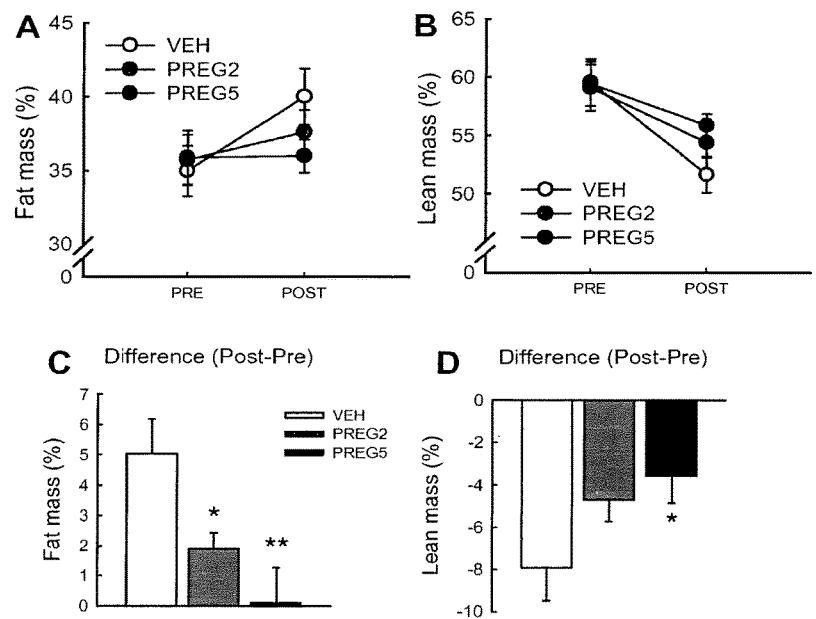

FIG. 10 shows diagrams depicting the effects of pregnenolone on the accumulation of fat and lean mass in obese mice. Pregnenolone, injected subcutaneously once a day before the start of the dark cycle, dose dependently blocked the increase in fat mass (A,C) and blunted the decrease in lean mass (B,D) observed during feeding with a high fat diet. Fat and lean mass were calculated using magnetic resonance in mice. PRE=value obtained before the start of pregnenolone administration. POST=values obtained after 30 days of treatment with pregnenolone or vehicle. *=P<0.05 **=P<0.01.

Figure 11:
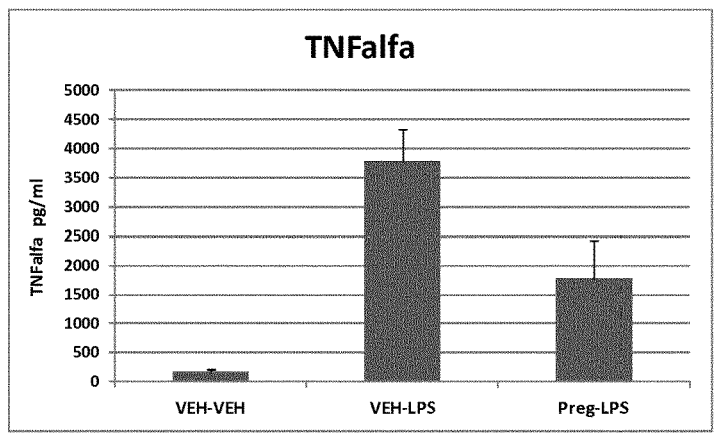

FIG. 11 shows diagrams depicting the inhibition by pregononlone of the increase in TNF alpha induced by LPS. The bacterial toxin LPS was injected intraperitoneally 30 min after the injection of Pregnenolone (6 mg/kg subcutaneously) or vehicle solution. Pregnenolone halved the increase in TNF-alpha induced by the injection of LPS. *=P<0.5

Figure 12:
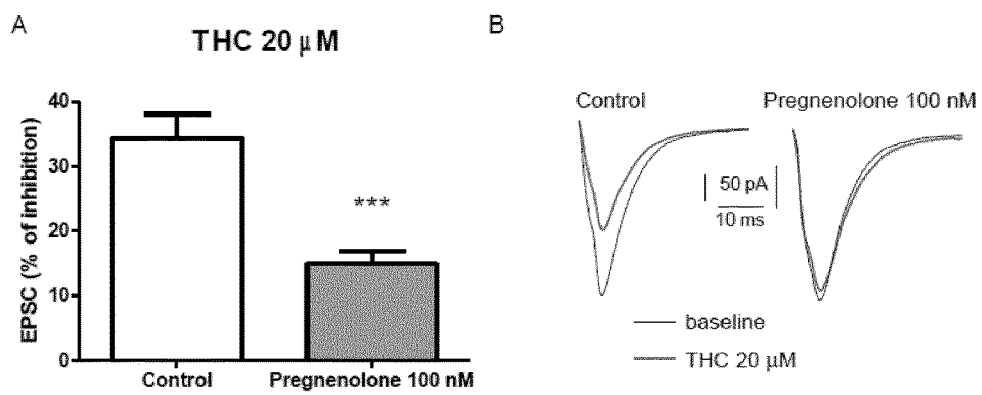

FIG. 12 shows diagrams depicting the inhibition by pregononlone of THC-induced inhibition of excitatory synaptic currents in the Nucleus Accumbens of rats. Excitatory post-synaptic currents (EPSC) induced by electrically stimulating local axons were recorded using patch clamp in Nucleus Acccumbens principal neurons in brain slices obtained from adult rats. (A) Bath application of THC (20 mM) reliably inhibited synaptic transmission in control slices (34.3±3.7% of inhibition, N=8). The effect of THC was significantly attenuated when slices were pre-treated with Pregnenolone 100 nM (15.1±1.8% of inhibition, N=9). (B) Synaptic current traces from representative experiments averaged during baseline and after 40 minutes of THC exposure. ***T test: t=4.820, df=15, p=0.0002.

Figure 13:
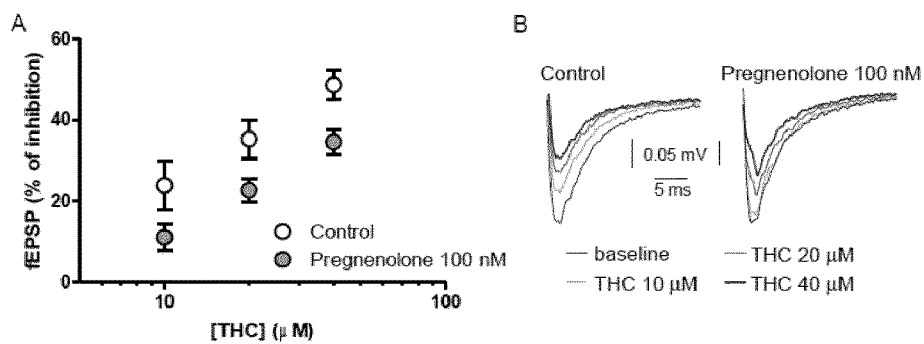

FIG. 13 shows diagrams depicting the inhibition by pregononlone of the THC-induced inhibition of excitatory synaptic transmission in mouse Nucleus Accumbens. (A) Field excitatory post-synaptic potentials (fEPSP) induced by electrically stimulating local axons were recorded in Nucleus Acccumbens brain slices obtained from adult mice. Bath application of THC induced a dose-dependent inhibition of synaptic transmission in control slices (N=5-9). The effects of THC were reduced when slices were pre-treated with Pregnenolone 100 nM (N=5-6). (B) Representative fEPSP average traces recorded during baseline and after 40 minutes of THC exposure. Two Way ANOVA: Pregnenolone effect p<0.002; THC effect p<0.0003.

Figure 14:
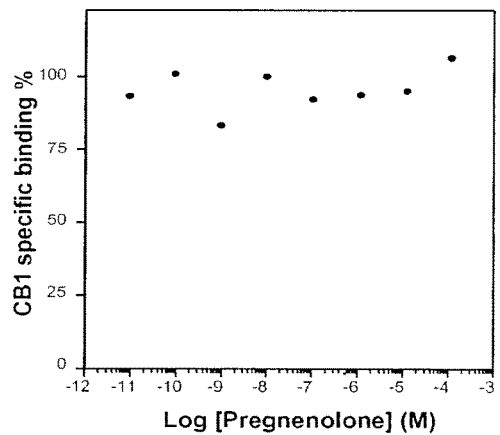

FIG. 14 shows diagrams depicting that pregnenolone is an inhibitor of the activation of the CB1 receptor, which does not modify the orthosteric binding of agonists of the CB1. Pregnenolone (10-12 to 10-4 M) did not modify the specific binding of the CB1 agonist [3H]CP55,940 to the human CB1 receptor expressed by CHO cells. Data are expressed as mean±SEM (n=2-3 per concentration).

Figure 15:
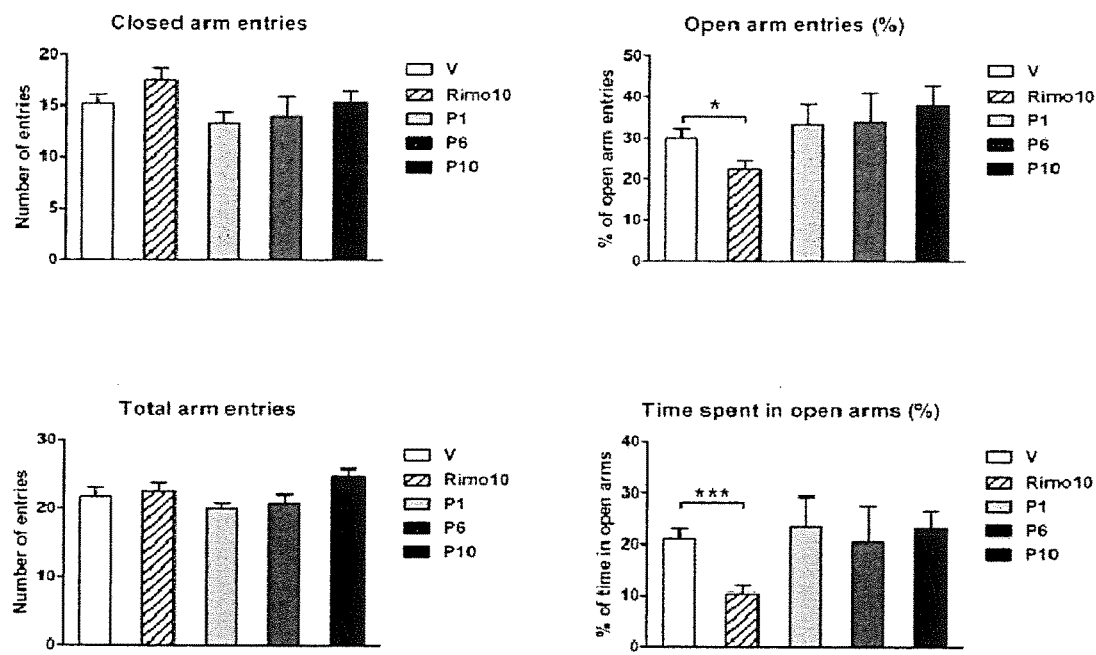

FIG. 15 shows diagrams depicting the lack of effects of pregnenolone on anxiety like behaviors. Anxiety-like behaviors were measured by the % of entries and time spent in the open arms of an elevated plus maze. Pregnenolone did not induce anxiety like behavior even at the highest doses (10 mg/kg) well above its effective behavioral doses between (1 and 6 mg/kg) corresponding to its maximal behavioral effects. The orthosteric antagonist of the CB1 receptor rimonabant at 10 mg/kg induced an increase in anxiety as shown by the decrease of the entries and time spent in the open arms. P1, P6, P10=pregnenolone 1, 6, 10 mg/kg. Rimo 10=rimonabant 10 mg/kg. V=vehicle. *=P<0.05; ***=P<0.001.

Figure 16:
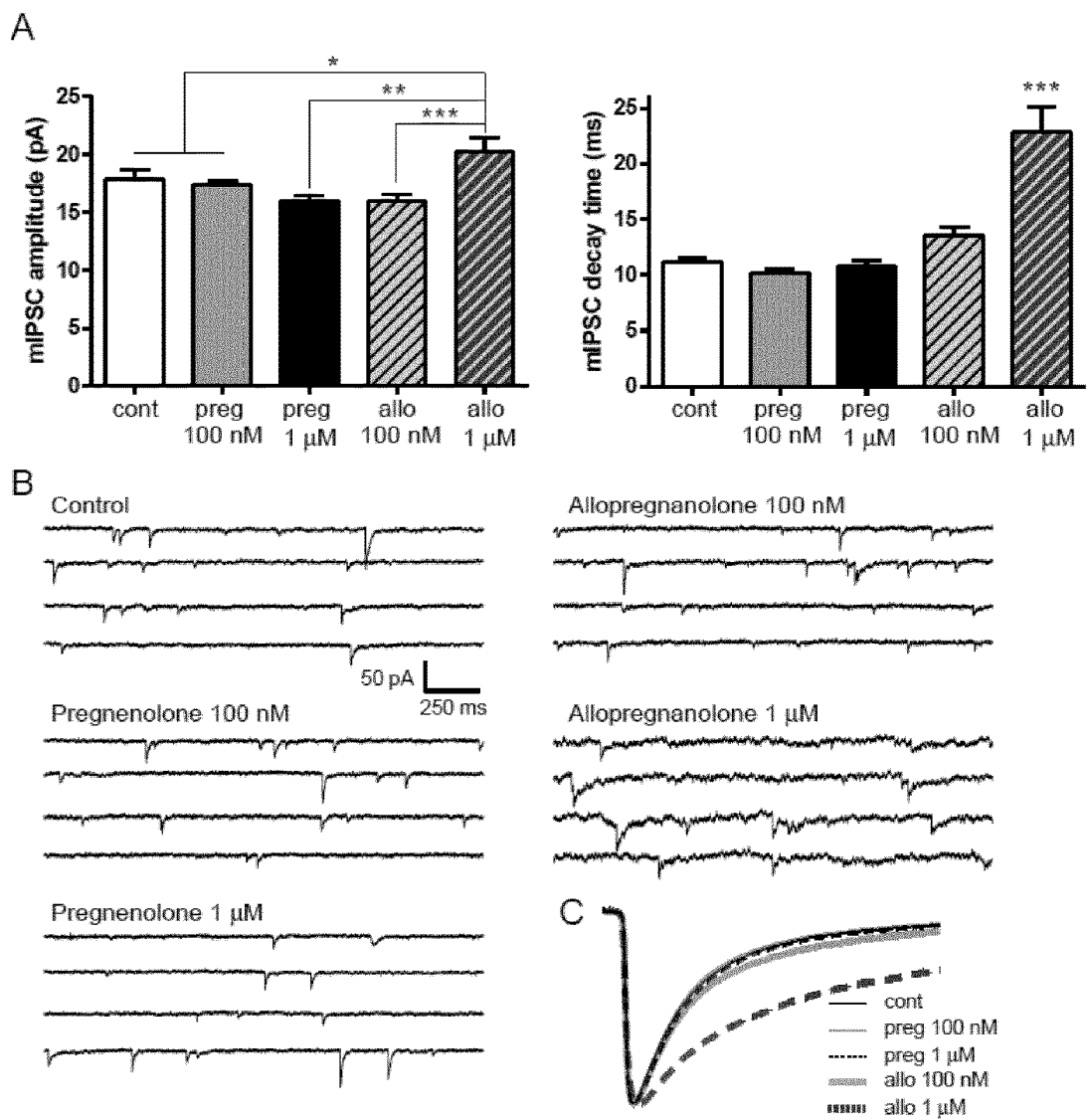

FIG. 16 depict diagrams showing that the lack of effect of pregnenolone on GABA-A receptors-mediated currents. mIPSC where recorded from adult mouse NAc PN voltage-clamped at −80 mV. A. Summary of amplitudes (ANOVA f=5.39, df=4.66, p<0.001) and decay times (ANOVA f=24.7, df=4.66, p<0.0001) of mIPSC from controls (N=16) and slices pre-treated with pregnenolone (100 nM: N=15; 1 µM: N=11) or allopregnanolone (100 nM: N=18; 1□M N=11).

Post hoc tests: *p<0.05, p<0.01, *p<0.001. B. representative traces of mIPSC recording. C. average mIPSC traces normalized to the peak. Note that only allopregnanolone 1 µM substantially affected mIPSC decay phase. cont=controls; preg=pregnenolone; allo=allopregnanolone.

Figure 17:
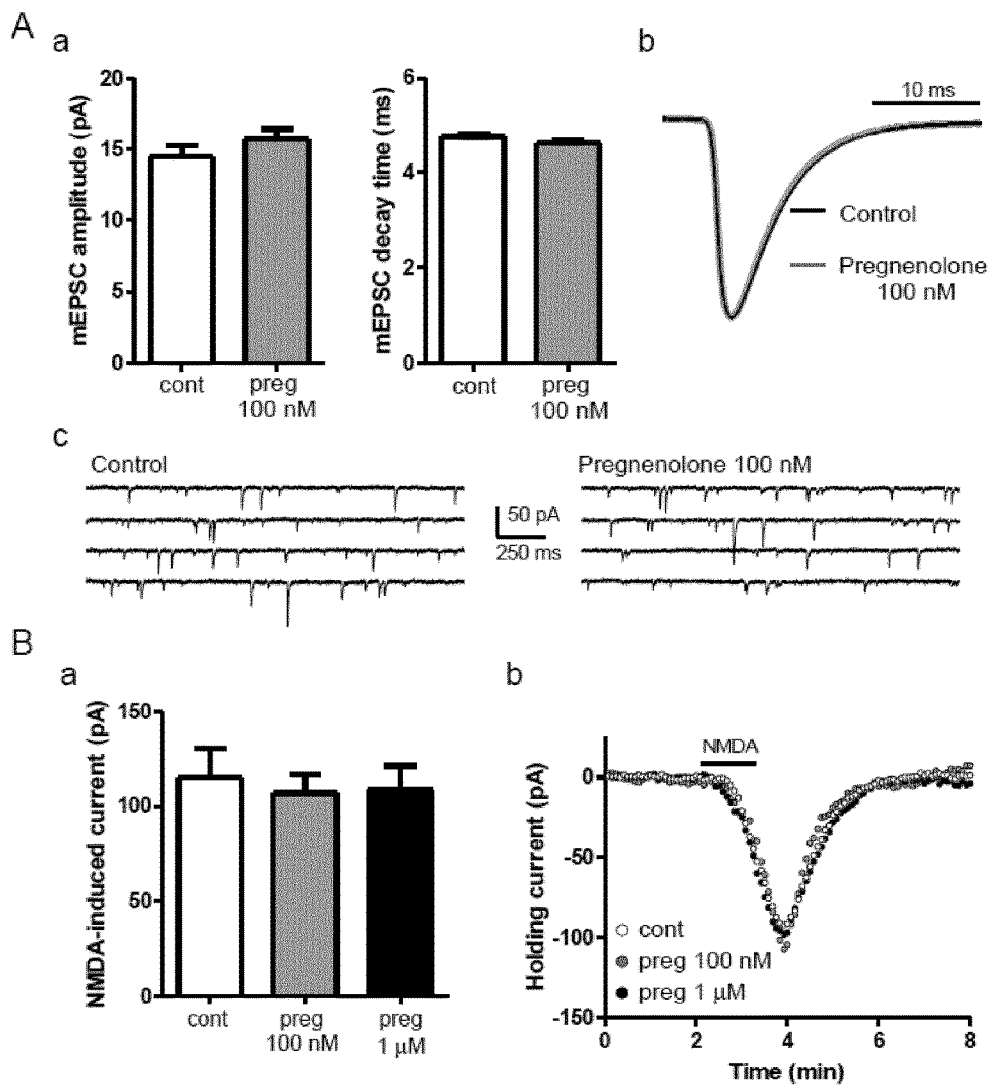

FIG. 17 depict diagrams showing that Pregnenolone does not modify AMPAR nor NMDAR-mediated currents. (A) mEPSC recorded from adult mouse Nucleus accumbens principal neuorons voltage-clamped at −80 mV. a) mEPSC recorded from control (N=16) and pregnenolone (100 nM) pre-treated (N=15) slices showed similar amplitude (T test: t=1.16, df=29, p=0.25) and decay time (T test: t=1.28, df=29, p=0.21). b) Average mEPSC traces normalized to the peak showing that its kinetics was not affected by pregnenolone. c) Representative traces of mEPSC recording. B. Whole cell currents recorded in NAc PN induced by bath application of NMDA 25 µM for 1 min. a) NMDAR-induced currents were comparable between controls (N=17) and slices pre-treated with pregnenolone 100 nM (N=12) and 1 µM (N=7) (ANOVA: f=0.09, df=2.33, p=0.91). b) Representative experiments showing the effect of NMDA on holding currents of NAc PN voltage-clamped at −30 mV. cont=controls; preg=pregnenolone.

Figure 18:
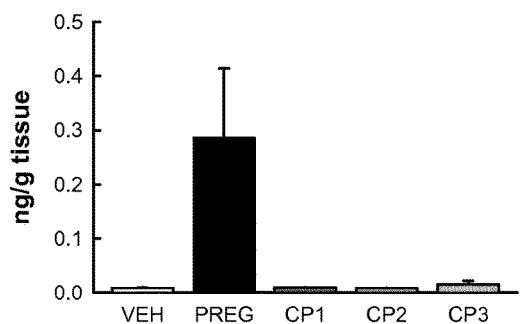
Figure 18:
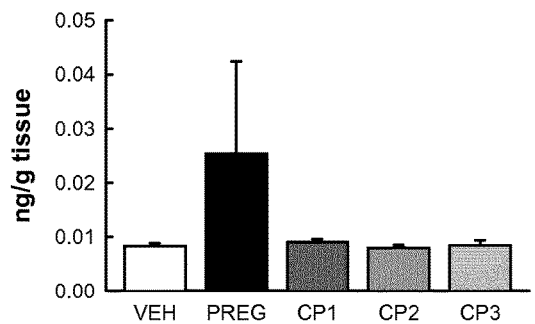

FIG. 18 shows diagrams depicting the effects of the injection of high doses (50 mg/kg, sc) of pregnenolone and of the C3 and C17 synthetic derivatives 3-Fluoropregnenolone (CP1), 17-methylpregnenolone (CP2) and 3-fluoro-17-methylpregnenolone (CP3) on nucleus accumbens steroids content. Pregnenolone but not 3-Fluoropregnenolone, 17-methylpregnenolone or 3-fluoro-17-methylpregnenolone increased allopregnanolone (A) and epiallopregnanolone (B) levels in the accumbens of Wistar rats. Data are expressed as mean±SEM (n=5-7 per group).

Figure 19:
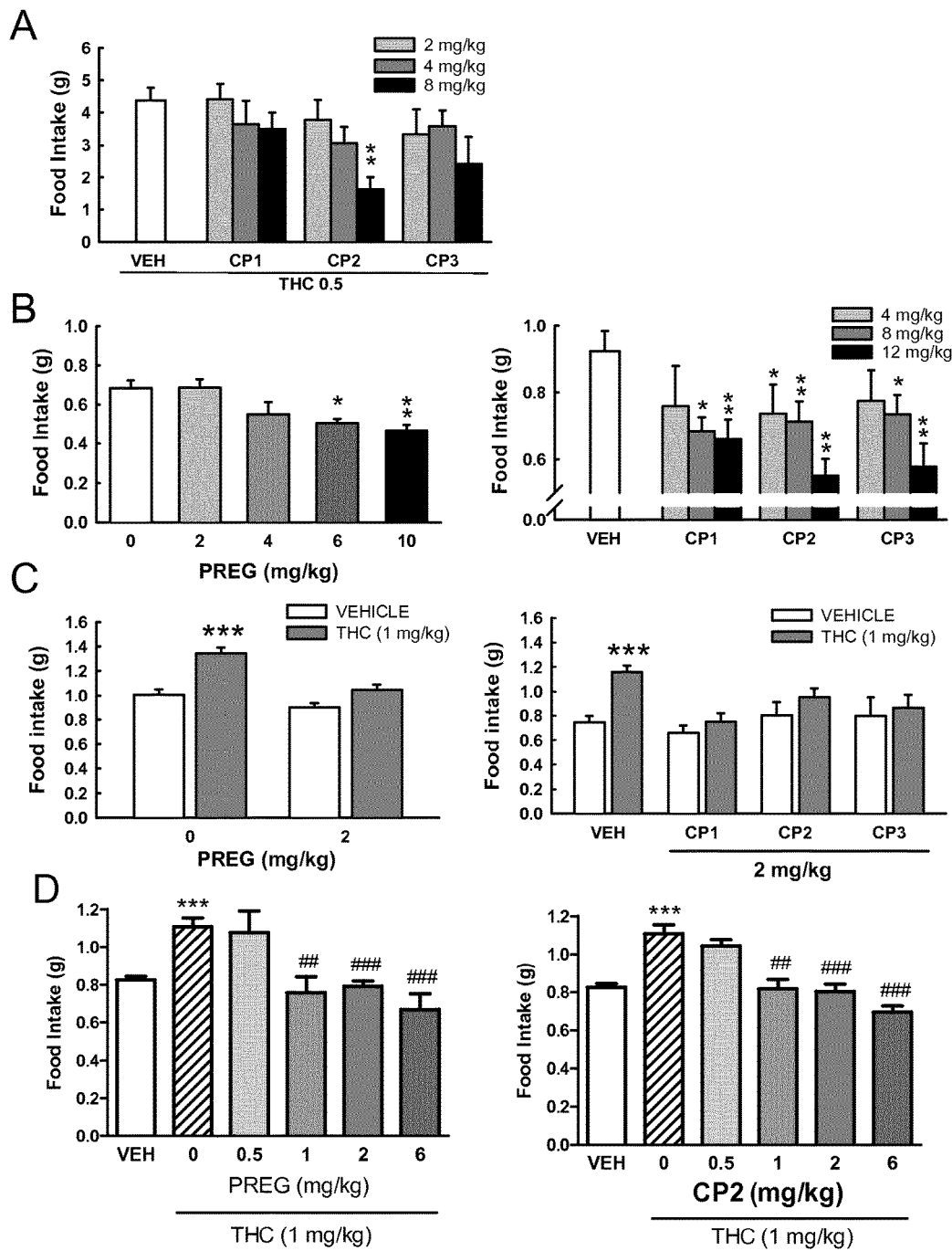

FIG. 19 depicts diagrams showing that the C3 and C17 synthetic derivatives 3-Fluoropregnenolone (CP1), 17-methylpregnenolone (CP2) and 3-fluoro-17-methylpregnenolone (CP3) reduced food intake. (A) The increase in food intake induced by THC (0.5 mg/kg, sc) in ad libitum fed Wistar rats was significantly reduced by 17-methylpregnenolone (8 mg/kg, sc), a non statistically significant trend to decrease was also observed after 3-Fluoropregnenolone and 3-fluoro-17-methylpregnenolone. (B) Pregnenolone [(F4.28)=5.5; P<0.01], 3-Fluoropregnenolone [(F3.20)=3; P<0.05], 17-methylpregnenolone [(F3.20)=5.3; P<0.01] and 3-fluoro-17-methylpregnenolone[(F3.20)=4; P<0.02] dose-dependently decreased food intake in 24 h-food deprived C57B1/6 mice. (C) Pregnenolone, 3-Fluoropregnenolone, 17-methylpregnenolone and 3-fluoro-17-methylpregnenolone (2 mg/kg, sc) decreased THC-induced hyperphagia in 24 h-food deprived C57B1/6 mice. (D) Full dose response effects of pregnononlone and 17-methylpregnenolone on THC-induced hyperphagia in 24 h-food deprived C57B1/6 mice. For both compound the first effective dose was 1 mg/kg. Data are expressed as mean±SEM (n=6-8 per group). *, P<0.05, =P<0.01; *=P<0.001 compared to vehicle-treated animals. ##=P<0.01; ###=P<0.001, compared to THC treated animals.

Figure 20:
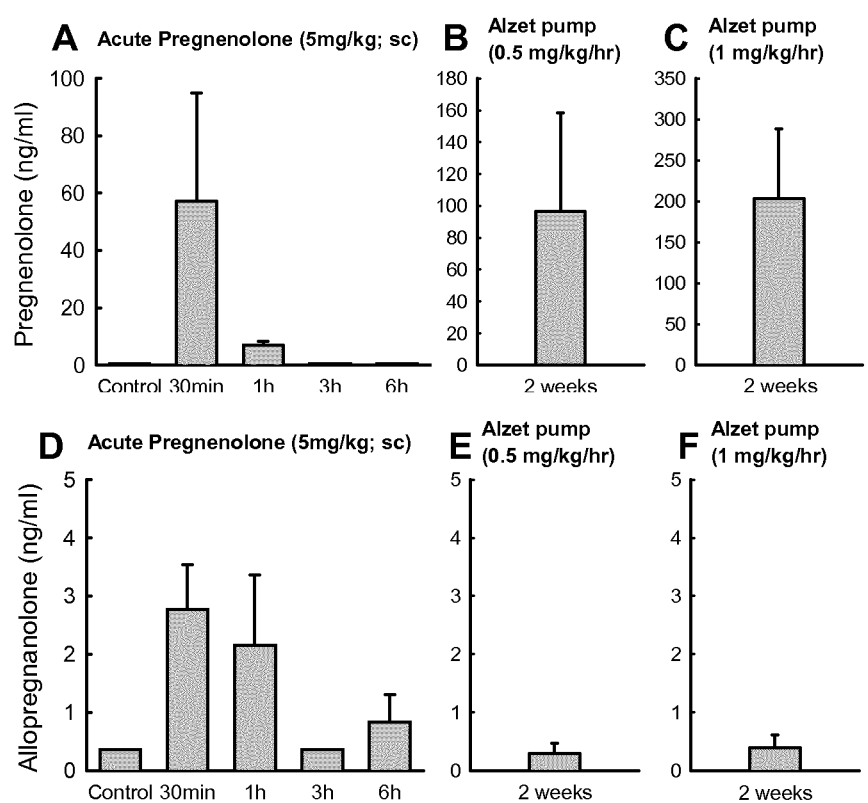

FIG. 20 shows diagrams depicting the effects of a steady state administration of pregnenolone with Alzet minipumps on the level of pregnenolone and down stream metabolite Allopregnanolone. The subcutaneous injection of pregnenolone induced an increase in pregnenolone levels (A) that was short lasting (<1 h) and also increased allopregnanolone levels over at least 1 hour (D). The administration of pregnenolone through Alzet minipumps (B,C) dose dependently increased plasmatic levels of pregnenolone but not the ones of allopregnanolone. (E,F).

EXAMPLES

Examples of Synthesis of Derivatives of Pregnenolone

Pregnenonole is well-known and commercially available and can be used as precursor for the synthesis of it derivatives.

Example of Synthesis of a Derivative of Pregnenolone Having C17 Substituted with an Alkyl:

As shown below, to synthesize a compound substituted with an alkyl at C17 position, in a first step, the corresponding enol acetate is formed. Then, it is treated with a Grignard reagent to generates an enolate which is subsequently trapped with an electrophile. The electrophile would be preferentially an iodo- or bromo-alkyl, -allyl, -benzyl or -aryl.

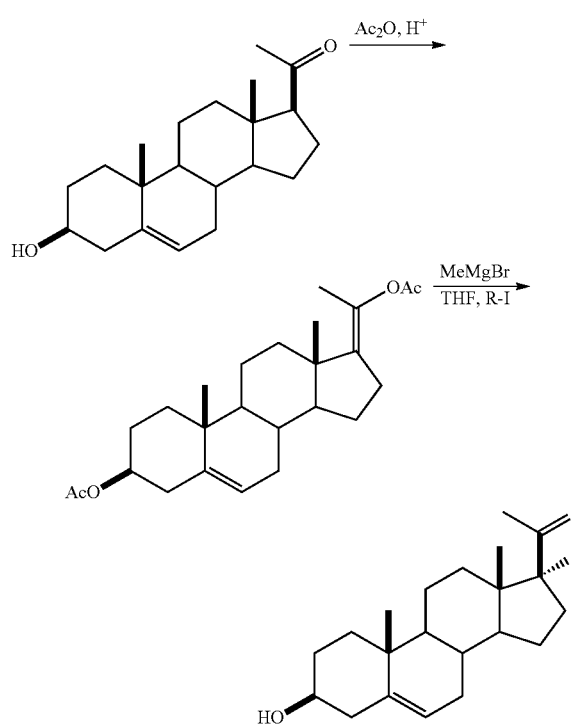

Example of Synthesis of a Derivative of Pregnenolone Having C17 Substituted with —OR The figure below shows how to obtain a C17 substituted with an alkoxy-, benzyloxy- and aryloxypregnenolones thank to copper-mediated functionalization with alcohols.

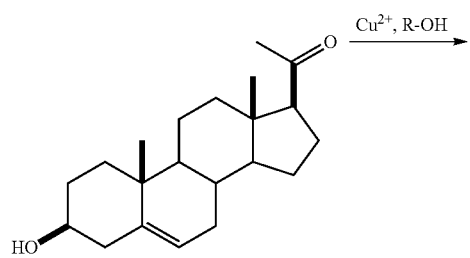

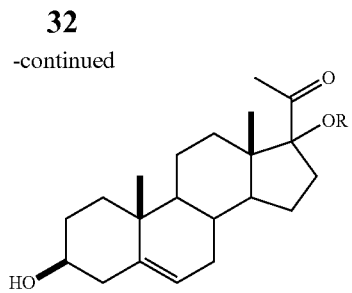

Example of Synthesis of a Derivative of Pregnenolone Having C3 Substituted with Halogen and C17 Substituted with R:

As shown below, the derivative of pregnenolone having C17 substituted with R is treated with DAST in order to change the alcohol function at C3 with a fluorine atom.

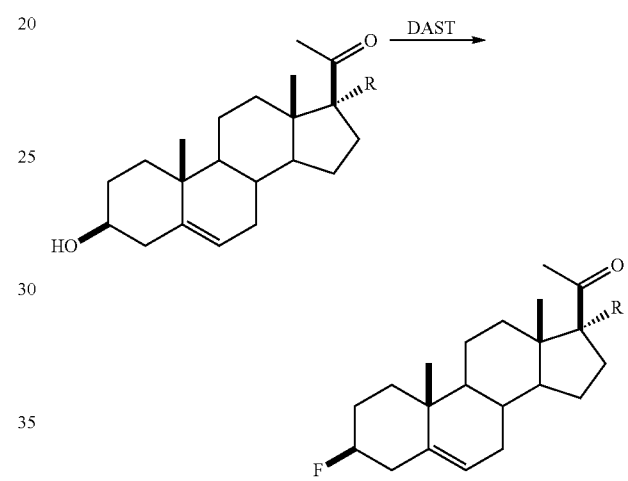

Example of Synthesis of a Derivative of Pregnenolone Having a C3 Substituted with an Alkoxy:

As shown below, the formation of an ether function at C3 position requires, in a first step, the transformation of alcohol into the corresponding tosylate as leaving group. Then, it is treated with the suitable alcohol in order to lead to the formation of C3-alkoxy pregnenolone.

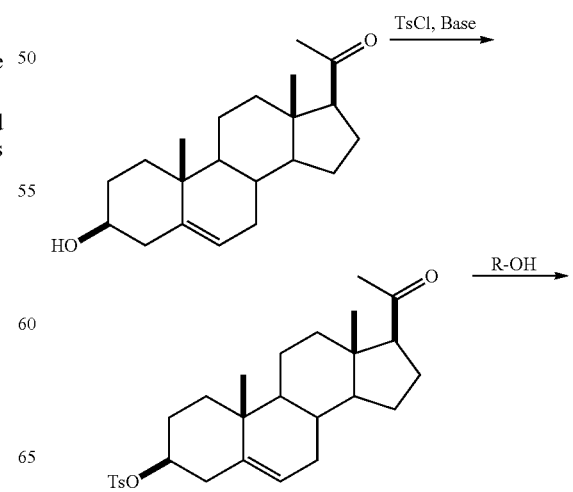

-continued

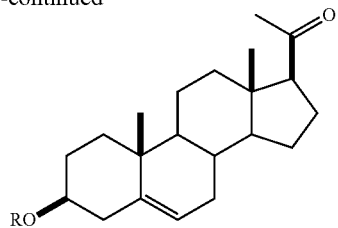

Example of Synthesis of a Derivative of Pregnenolone Having C3 Substituted with =O and C17 Substituted with R:

As shown below, to obtain a derivative of pregnenolone having a C3 substituted with =O and C17 substituted with R, C17-substituted pregnenolone is treated with oxidants to lead to the oxidation of alcohol function into the corresponding ketone followed by the spontaneous isomerization of the double bond to give modified progesterones.

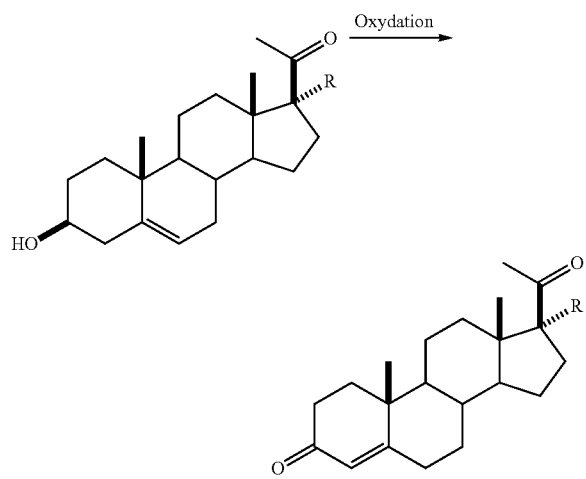

Examples of Role of Pregnenolone and its Derivative in the Inhibition of CB1 Receptor.
Material and Methods:
Animals Animals were individually housed in a temperature (22° C.) and humidity (60%) controlled animal facility under a constant light-dark cycle (light on, 8:00-20:00 h). Except for food intake experiments and during the experimental sessions of WIN 55, 212-2 self administration, food and water were freely available throughout the experiments. After arrival animals were handled periodically for two weeks before experiments. Most of the experiments were performed during the light phase except for the food intake experiments in rats and WIN 55, 212-2 self administration sessions test in CD1 mice that were conducted during the dark phase. All the experiments were conducted in strict compliance with the recommendations of the European Union (86/609/EEC).

Adult male Wistar rats (3-4 months), C57B1/6N mice (2-3 months) C57B1/6j mice (2-3 months) and CD1 mice (weighing 25-30 g at the beginning of the experiments) were purchased from Charles River Laboratories (France). CB1-deficient (CB1−/−) and D1-CB1 mutant (D1-CB1−/−) mice were produced in our laboratory as described (Marsicano et al., Nature. 2002 418:530-4; Monory et al., PLoS Biol. 2007 5(10):e269).

Drugs

Δ9-tetrahydrocannbinol (THC, Sigma-Aldrich, France) was purchased as a 30 mg/ml (w/v) solution in 100% ethanol. Before injection this solution was dissolved with Tween 80 (1 drop/3 ml) and dimethylsulfoxide (DMSO) diluted 1:40 with saline (2.5%). Vehicle solution contained all ingredients (1 drop/3 ml of Tween 80, DMSO (2.5%) and ethanol diluted with saline to obtain a final concentration of 1.8% of ethanol). Cocaine HCl (Coopération Pharmaceutique Française, France), morphine sulfate (Francopia, France), nicotine bitartrate (Sigma-Aldrich, France) and USP alcohol (95%, Sigma-Aldrich, France) were dissolved in saline. HU210, JWH133 and AM251 were purchased from Tocris, UK and WIN 55, 212-2, aminoglutethimide (AMG) pregnenolone (5-Pregnen-3β-ol-20-one) lipopolysaccharides from $E.\ Coli$ 0111:B4 (LPS) from Sigma-Aldrich (France) and rimonabant (SR141716A) from Cayman Chemical (Interchim, Montluçon, France).

The synthetic compounds 3-Fluoropregnenolone; 17-methylpregnenolone and 3-fluoro-17-methylpregnenolone were synthesized by AtlanChimPharma (France). Drug solutions were dissolved in Tween 80 (1 drop/3 ml) and DMSO (2.5%) or NMP (2.5%) and diluted in saline solution. THC, cocaine, morphine, nicotine, ethanol, HU210, JWH133, AM251, WIN 55, 212-2, AMG and SR141716A were injected intraperitoneally (ip) and pregnenolone or pregnenolone derivatives were injected subcutaneously (sc). The injection volumes were 1 ml/kg of body weight for rats and 10 ml/kg for mice.

In SA experiments, WIN 55, 212-2 (Sigma Chemical Co., Madrid, Spain) was dissolved in one drop of Tween 80 and diluted in saline solution. Ketamine hydrochloride (100 mg/kg) (Imalgène 1000; Rhône Mérieux, Lyon, France) and xylazine hydrochloride (20 mg/kg) (Sigma, Madrid, Spain) were mixed and dissolved in ethanol (5%) and distilled water (95%). This anesthetic mixture was administered intraperitoneally prior to catheter implantation in an injection volume of 20 ml/kg of body weight. Thiopental sodium (5 mg/ml) (Braun Medical S.A, Barcelona, Spain) was dissolved in distilled water and delivery by infusion of 0.1 ml through the intravenous catheter. For in vitro human CB1 receptor functional assay, pregnenolone and CP 55940 were dissolved in DMSO to final concentration of 100 mM and stored at −20° C.

Neurosteroid Quantification

Blood and Brain Sampling.

The animals were sacrificed by decapitation and trunk blood was collected in EDTA-coated tubes, centrifuged at 2000×g for 10 min, and the supernatant was stored at −20° C. Brains were quickly harvested, the brain areas were dissected on ice and samples were rapidly frozen in cold ice and stored at −80° C.

Measurement of Steroid Levels by GC/MS.

Plasma, brain and culture medium levels of pregnenolone (5-Pregnen-3β-ol-20-one), allopregnanolone (3α-hydroxy-5α-pregnan-20-one), epiallopregnanolone (3β-hydroxy-5α-pregnan-ol-20-one), testosterone, and 5α dihydrotestosterone were determined by GC/MS according to the of estraction, purification and quantification protocol described previously (George O, et al., Biol Psychiatry. 2010 68: 956-63, Vallee M, et al., Anal Biochem. 2000, 287:153-66).

THC Behavioral Tetrad

Body Temperature.

Body temperature was measured using a rectal probe (RET3 probe, Physitemp instruments, USA) in conscious mice and was monitored by a thermalert monitoring thermometer (TH-5, Physitemp instruments, USA).

Locomotor Activity.

Locomotion was measured by an automated open field system (box size 100×100×30 cm, illumination of 10 lux, videotracking system: Viewpoint, Lyon, France) or Plexiglas cages (19 cm long×11 cm wide×14 cm high) mounted with computer-monitored photocell beams (Imetronic, France). Animals were individually tested for 15 min. The cumulative horizontal distance the animals moved within the box was recorded.

Catalepsy.

Catalepsy was measured by the bar catalepsy test. The forepaws of mice were placed on a 1-cm-diameter bar fixed horizontally at 3.5 cm from the bench surface. The latency to descend was recorded.

Analgesia.

Analgesia was measured using a hot plate analgesia meter (BIO-HC1.00, Bioseb, France). The plate was heated to 52° C.±0.1° C. and the time until mice showed the first sign of discomfort (licking or flinching of the paws or jumping on the plate, here defined as escape latency) was recorded. A cut-off time of 60 s was set to prevent tissue damage.

Object Recognition Task

Object recognition was measured in a two arms L-maze (size of each arm 30 cm length×4.5 cm width) in dim light condition (50-60 lux). Animals were individually tested for three consecutive days for 9 min-session each day, corresponding to habituation, training and test sessions. On day 1 (habituation session), mice were let explore the L maze with no object. On the second day (training session), two identical objects were presented at the end of the each arm of the maze. Although no preferences for arm of object appeared (data not shown) object and arms were randomized for each mouse/condition. On the 3rd day (test session), one of the familiar objects was replaced with a novel object and the total time spent exploring each of the two objects (novel and familiar) was computed. The time spent in each arm and the time spent exploring an object (familiar or novel) were recorded. Object exploration was defined as the orientation of the nose to the object at a distance of less than 2 cm. During the test session, a discrimination index was calculated as the difference between the times spent exploring either the novel or familiar object divided by the total time exploring the two objects. A higher discrimination index is considered to reflect greater memory retention for the familiar object (Puighermanal et al., 2009).

Food Intake Measurements

Food intake was evaluated by measuring consumption of food in the home cages of the animals. For each animal, 50-100 g of standard laboratory chow (U.A.R., France) was placed in the cleaned home cage. The remaining amount of food was weighted 1 h later and the amount of food consumed calculated.

WIN 55, 212-2 Self-Administration

The intravenous self-administration experiments where the animals learned to self-infuse WIN 55, 212-2 (WIN) were conducted in mouse operant chambers (Model ENV-307A-CT, Medical Associates, Georgia, Vt., USA) using procedures previously described (Mendizabal V, et al., Neuropsychopharmacology. 2006, 31:1957-66).

Coupled In Vivo Microdialysis and Electrophysiology General Procedures.

Surgery and perfusion procedure were performed to allow concomitant electrophysiological and microdialysis monitoring. Briefly, rats were anesthetized using a 2% mixture of isoflurane/air, and a catheter was inserted into the femoral vein for intravenous drug administration. Thereafter, animals were placed in a stereotaxic frame (David Kopf Instruments, Phymep, Paris, France) equipped with a nose mask for constant delivery of the gas anesthesia (2% isoflurane during surgery, 1.5% isoflurane during electrophysiology and microdialysis experiment), and their rectal temperature was monitored and maintained at 37±1° C. by a heating pad (CMA 150, Carnégie Medecin, Phymep). A microdialysis probe (CMA/11, 2 mm long, 240 μm outer diameter, Cuprophan; Carnegie Medicin, Phymep) and a recording electrode (glass micropipette TW150E-4, 2-3 μm outer diameter, WPI-Europe, Aston Stevenage, UK) were implanted respectively in the medio-ventral part of the right nucleus accumbens corresponding to the shell subdivision [coordinates, in mm relative to bregma: anteroposterior (AP)=+1.7, lateral (L)=1, ventral (V)–8], and in the right ventral tegmental aerea (VTA) (coordinates, in mm relative to bregma: AP=–5.4-5.8, L=0.4-0.8, V=–7.0-8.5], according to the Paxinos and Watson atlas. Probes were perfused at a constant rate of 2 μL/min by means of a microperfusion pump (CMA 111, Carnegie Medicin, Phymep) with artificial cerebrospinal fluid (aCSF) containing (in mM): 154.1 Cl⁻, 147 Na⁺, 2.7K⁺, 1 $Mg^{2+}$, and 1.2 $Ca^{2+}$, adjusted to pH 7.4 with 2 mM sodium phosphate buffer. Perfusion was then maintained during 2 h to allow the stabilization of dopamine (DA) levels in the perfusates.

Single unit recording of DA neuronal firing and monitoring of DA extracellular levels were started 2 h after the beginning of probe perfusion (stabilization period). Dialysates (30 μL) were collected on ice every 15 min, and immediately analyzed to determine the baseline values of DA extracellular levels, defined by three consecutive samples in which DA content varied by less than 10% (9). Search of DA neurons for electrophysiological recording was performed during the 30 min preceding the drug treatment (THC or cocaine) administration. DA neuron firing rate was recorded for 3-5 min to obtain the firing baseline, defined by a variation of less than 10% of the average frequency discharge of the DA neuron. Pharmacological treatments were performed once obtained a stable baseline for DA neuron firing and DA extracellular levels in the perfusate.

DA Neuron Recording.

Single unit activity of neurons located in the VTA was recorded extracellularly with glass micropipettes filled with 1% Fast Green dissolved in 0.5 M sodium acetate (impedance, 2-5 MΩ). Signals were filtered (bandpass, 0.4-1 kHz) and amplified by a high-impedance amplifier (Dagan 2400A, Dagan Corporation, USA) and individual spikes were isolated by means of a window discriminator (WD-2, Dagan Corporation, USA), displayed on an analog-digital storage oscilloscope (HM507, Hameg, Frankfurt, Germany). Then, the experiments were sampled on line with Spike2 software (Cambridge Electronic Design, Cambridge, UK) by a computer connected to CED 1401 interface (Cambridge Electronic Design, Cambridge, UK). VTA DA neurons were identified according to the already published criteria (12-14). The firing rate was defined as the number of spikes/sec.

DA Assay.

dialysates were injected into an HPLC apparatus equipped with a reverse phase Equisil BDS column (C18; 2×250 mm, particle size 5 μm; Cluzeau Info Labo, Step Foy la Grande France), and an amperometric detector (Antec Leyden DECADE II, Alpha-mos, Toulouse, France) with a glassy carbon electrode set at +450 mV versus Ag/AgCl, in order to quantitate DA. The composition of the mobile phase was (in mM) 70 NaH2PO4, 0.1 $Na_2EDTA$, and 0.1 octylsulfonic acid plus 10% methanol, adjusted to pH 4.8 with orthophosphoric acid. The sensitivity for DA was 0.3 pg/20 μL with a signal/noise ratio of 3:1.

Histology.

At the end of each experiment, a direct continuous current (−20 μA for 15 min) was passed through the electrode to eject Fast Green dye, allowing the identification of the recording site. Afterwards, brains were removed and fixed in NaCl (0.9%)/paraformaldehyde solution (10%). The location of the electrodes in the VTA and the microdialysis probes in the nucleus accumbens was determined by microscopic examination on serial coronal sections (60 μm) stained with Neutral Red.

Diet Induced Obesity and Evaluation of Fat Accumulation 2-months old male C57BL/6J mice were ad libitum fed a 60% high-fat diet (HFD; Catalog #D12492, Research Diets, New Brunswick, N.J.) for 8 weeks and subsequently treated either with pegnenolone or vehicle. Homogeneous distribution of the animals in the 3 treatment groups was guaranteed by matching their body weight, fat mass and fasting glucose levels before the start of the pharmacological treatments.

Body Composition Analysis.

Fat mass and lean mass were assessed in vivo using an EchoMRI analyzer (EchoMedical Systems, Houston, Tex.) before the mice were placed on the HFD, as well as immediately before and at the end of the chronic treatment with pregnenolone or its vehicle.

Plasma Free Fatty Acids Measurement.

Trunk blood from DIO mice was collected at the end of the 4 weeks of treatment and plasma free fatty acids (FFA) were measured by a colorimetric reaction kit, following the manufacturer's instructions (Abcam, catalog #65341).

Plasma TNFalpha Measurement.

Trunk blood was collected and centrifuged at 3000 rpm for 15 min at 4° C. Plasma was stored at −80° C. until measurement of TNFα was carried out. Plasma TNFα levels were assessed using an ELISA kit, following the manufacturer's instructions (Fisher Scientific, Catalog #E6473C).

Electrophysiology on Brain Slices

Slice Preparation.

Animals were deeply anesthetized with Isoflourane and transcardially perfused with a sucrose-based physiological solution at 4° C. (in mM: 23 $NaHCO_3$, 70 Choline Cl, 75 Sucrose, 25 Glucose, 2.5 KCl, 1.25 $NaH_2PO_4$, 7 $MgCl_2$ and 0.5 $CaCl_2$). The brain was removed and sliced (250-300 μm) in the coronal plane using a vibratome (Campden Instruments, Loughborough, UK). During the slicing process, the brain was maintained in the sucrose-based solution. Immediately after cutting, slices were stored at 32° C. for 40 minutes in a low-calcium artificial cerebrospinal fluid (low-$Ca^{2+}$ ACSF) that contained (in mM): 23 $NaHCO_3$, 120 NaCl, 11 Glucose, 2.5 KCl, 1.2 $NaH_2PO_4$, 2.4 $MgCl_2$, 1.2 $CaCl_2$. Slices were then stored in low-$Ca^{2+}$ ACSF at room temperature until recording.

Electrophysiology.

Recordings were performed with an Axopatch-1D amplifier (Molecular Devices, Sunnyvale, Calif.). Data were filtered at 1-2 kHz, digitized at 10 kHz on a Digidata 1332A interface (Molecular Devices), collected on a PC using Clampex 9, and analyzed using Clampfit 10 (Molecular Devices).

Whole cell patch-clamp recordings were performed from NAc core principal neurons (PNs). Cells were identified using differential interference contrast infrared videomicroscopy (Leica DM LFSS microscope, Leica Microsystems, Germany; Camera Till Photonics, Germany).

For recording AMPAR and NMDAR-mediated currents, glass patch clamp electrodes (resistance 4-6 MOhms) were filled with a cesium-based solution as follows (in mM): 125 Gluconic acid, 125 CsOH, 10 HEPES, 10 NaCl, 0.3 EGTA, 0.05 Spermine, 10 TEA-Cl, 2 $MgCl_2$, 0.3 $CaCl_2$, 4 $Na_2ATP$, 0.3 NaGTP, 0.2 cAMP. For recording inhibitory currents, a similar solution was used with the exception of (in mM): 80 Gluconic acid, 80 CsOH, 30 CsCl, 20 NaCl. The higher chloride concentration favor a stronger driving force when recorded at hyperpolarized potentials. Throughout the experiments access resistance, ($R_a$) was evaluated with a 2-mV hyperpolarizing pulse. $R_a$ was not compensated and cells were rejected if $R_a$ was >25MΩ or changed >20% during the experiment. The potential reference of the amplifier was adjusted to zero prior to breaking into the cell.

For fEPSPs, extracellular glass recording and stimulating electrodes were filled with ACSF. Synaptic potentials were evoked by means of two electric stimuli (0.1-0.25 mA, 200 μsec duration) delivered at 20 Hz every 10 seconds. Stimulating electrode was placed at a distance>150 μm in the dorsomedial direction from the recoding electrode.

Data Acquisition and Analysis.

AMPAR-mediated synaptic currents: GABA-A receptors were blocked by adding picrotoxin 50 μM to the superfusion medium. The contribution of NMDAR was ruled out by recording at hyperpolarized potentials. For evoked synaptic currents and mEPSC cell were voltage clamped at −70 mV and −80 mV, respectably. mEPSC were recorded in the presence of TTX 0.5 μM.

NMDAR-mediated currents: Changes in holding currents induced by NMDA were measured in cells voltage clamped at −30 mV, to relieve NMDAR from the voltage-dependent magnesium block. AMPAR and GABA-A receptors were blocked with DNQX 20 μM and picrotoxine 50 μM, respectably.

GABA-A receptors-mediated currents: mIPSC were recorded in the presence of the AMPAR and NMDAR antagonists (DNQX 20 μM and AP-5 50 μM, respectably). mEPSC-mIPSC analysis: Typically, after breaking in, cells were left to equilibrate for 20 minutes and the subsequent 10 minutes recording of mEPSC-mIPSC was used to analysis. mEPSC-mIPSC were detected using a template generated from averaging several typical events (Clampfit 10, Molecular Devices). The template was slid along the data trace one point at a time. At each position, the template was optimally scaled and offset to fit the data. A lower-amplitude threshold of 7 pA and 10 pA were applied for mEPSC and mIPSC, respectably, equivalent to 2.5SD of baseline noise. For each cell, the kinetics of mEPSC-mIPSC was measured from the average event using Clampfit 10. To estimate decay times, a two exponentials curve was fitted between 5 and 95% of the decay phase of the current given by the following equation: $y(t)=A1\cdot e^{(-t/\tau 1)}+A2\cdot e^{(-t/\tau 2)}$, where A is the amplitude, t is the time and τ is the decay time constant. The weighted tau was then calculated.

In Vitro Human CB1 Receptor Assays

The binding assay for orthosteric binding of pregnenolone has been evaluated using Chinese hamster ovary (CHO) cells expressing the human CB1 receptor.

The CB1 binding of pregnenolone has been evaluated by the affinity of pregnenolone for the agonist site of the human CB1 cannabinoid receptor expressed in CHO cells, determined in a radioligand binding assay of the CB1 agonist [3H] CP 55940. The experiments were performed by CEREP France, using the standard procedures of this provider.

Elevated Plus Maze

The elevated plus maze was made by a central platform (10×10 cm) from which departed 4 arms (45×10 cm) at a 90° angle from each other. Two opposite arms, named closed arms had peripheral wall 50 cm high. The two other arms, named open arms had no walls. The maze was suspended at 66 cm from the floor of the room and was brightly lighted (120 lux). The testing consisted in placing the animal in the central platform and the number of entry and the time spent in each compartment of the maze recorded for 5 min. The number of entry and time spent in the open arms are considered and index of anxiety-like behaviors, whilst the total number of entry are and index of locomotor activity.

Study of Metabolism In Vitro

The CHO-K1 cell line (#CCL-61, ATCC-LGC, USA) derived as a subclone from the parental CHO cell line initiated from a biopsy of an adult Chinese hamster ovary was used. The CHO-K1 cells were seeded on 24-well plates (#353047, BD Biosciences, USA) to the appropriate concentration ($25 \times 10^4$ cells/well) in fresh, antibiotic-free medium constituted by 90% DMEM-Glutamax; (#31966-21, Life technologies, USA) and 10% Fetal Bovine Serum (#10270-106, Life technologies, USA).

Steady State Administration of Pregnenolone

Micro-osmotic pumps (Alzet Osmotis Pumps, Charles River, France) with a pump rate of 0.15 μl/hr (model 2006) were filled with pregnenolone dissolved in PEG300 (85%) and ethanol (15%) at a concentration of 125 or 250 mg/ml (corresponding respectively to a daily dose of 12 or 24 mg/kg body weight) and implanted subcutaneously after light anesthesia. All pumps were primed by soaking them in saline at 37° C. for 60 h before implantation.

Statistical Analysis

Statistical analysis were performed using: Two-way or one way analysis of variance (ANOVA), Newman-Keuls, Student's T-tests. All results were expressed as mean±S.E.M. Statistical tests were performed with Graph-Pad Prism (GraphPad Software Inc., La Jolla, Calif., USA) or Statistica 5.0© (StatSoft Inc, Tulsa, Okla., USA).

Results:

I. CB1 Activation Increases Pregnenolone Synthesis and Concentrations

Example 1: THC Increases Pregnenolone Concentrations in the Brain More than Other Drugs of Abuse In this example the inventors analyzed the effects of the injection of the principal drugs of abuse on the production of pregnenolone in male Wistar rats. In all tissues, the first step of steroid synthesis is the production of pregnenolone that has been largely considered as an inactive precursor of downstream active molecules. For example, in the brain, starting from pregnenolone two parallel enzymatic cascades allow producing on one hand allopregnanolone and its stereoisomer epiallopregnanolone and on the other testosterone and its metabolite DHT. These brain steroids were quantified using GC-MS, the only technique able to differentiate their subtle structural differences. The major classes of drugs of abuse were injected subcutaneously or intraperiotenally at doses corresponding to the ED50 for most of their unconditioned behavioural effects: the psychostimulant cocaine (20 mg/kg), the opioid morphine (2 mg/kg), nicotine (0.4 mg/kg), alcohol (1 g/kg) and the active principle of cannabis sativa Δ9 tetrahydrocannabinol (THC) (3 mg/kg). Concentrations of neurosteroids were analyzed 15, 30 and 120 min after the injection in several ascending brain structure, the ventral midbrain the hypothalamus, the striatal complex and the frontal cortex.

Very similar results were obtained in all the brain structures studied (frontal cortex, striatum, accumbens, ventral midbrain). As shown in the example for the ventral striatum (the nucleus accumbens) basal level of steroids (FIG. 1A) ranged from approximately 1 ng/g of tissue for pregnenolone and testosterone to 0.2 ng/g for epiallopregnanolone. DHT and allopregnanolone had intermediate levels around 0.4 ng/g. All drugs of abuse increased brain concentrations of pregnenolone between 15 and 30 min after the injection (FIG. 1B). Strikingly, the increase in pregnenolone induced by THC was several time higher than the one induced by the other drugs of abuse: around 1500% increase for THC compared to approximately 200% increase for the other drugs of abuse.

Example 2: THC Increases Pregnenolone Concentrations in the Brain of Rats in a Dose Dependent Manner In this example the inventors further characterized the effects of the administration of different concentrations of THC (0.3, 0.9, 1.5, 3, 6 and 9 mg/kg) or vehicle to male Wistar rats on body concentrations of pregnenolone measured at the pick of the drug effects that, as shown in the previous example, was observed 30 min after the injection. These experiments demonstrated that the increase in pregnenolone observed in the brain was dose dependent, with an ED50 of approximately 3 mg/kg. The example provides data obtained in the plasma and in several brain structures: frontal cortex (FCX); nucleus accumbens (ACC); striatum (STR); hypothalamus (HYP). After THC administration, pregnenolone increased in all the studied brain structures in a comparable manner. Pregnenolone also increased in the plasma but this increase was several times lower than the one observed in the brain.

Example 3: THC Increases Pregnenolone Concentrations in the Brain of Mice in a Dose Dependent Manner In this example the inventors further characterized the effects of the administration of THC on concentrations of pregnenolone by studying the effects of THC in the mouse. Pregnenolone was measured at the pick of the drug effects, 30 min after the injection. These experiments demonstrated that THC induced a dose-dependent increase in pregnenolone also in mice. The example provides data obtained from the several brain structures: frontal cortex (FCX); nucleus accumbens (ACC); striatum (STR). THC induced a similar increase in pregnenolone concentration in all these brain structures.

Example 4: Agonists of the CB1 Receptor Induce an Increase in Pregnenolone Concentrations Similar to the One Induced by THC The effects of THC in the brain are mediated by a family of G-protein-coupled seven membrane receptors (GCPR) and principally by the CB1 and CB2 receptors. THC increased pregnenolone synthesis via the activation of the CB1 receptor. Thus, the injection to independent groups of rats (n=6-12 per group) of both a synthetic mix CB1/CB2 agonists Win55,212 and of an agonist that have a higher affinity for the CB1 than for the CB2 receptor (HU210)

induced a significant increase in pregnenolone. In contrast, an agonist with a higher affinity for the CB2 than the CB1 receptor (JWH, 133) had a much lower and not significant effects on pregnenolone concentrations Example 5: THC-Induced Increase in Pregnenolone is Suppressed by an Antagonist of the CB1 Receptor The dependence of THC effects on CB1 activation were further demonstrate by the observation that the increase in pregnenolone concentrations induced in the nucleus accumbens of Wistar rats by the administration of THC (3 mg/kg, i.p) was blocked by the administration of a CB1 selective antagonist (AM251, 8 mg/kg, i.p.) that was injected 30 min before the injection of THC (n=6 per group).

Example 6: THC-Induced Increase in Pregnenolone is Suppressed in Mutant Animals Lacking the CB1 Receptor In this example the inventors further analyzed the dependence from the CB1 receptor of the increase in pregnenolone induced by THC. For this purpose the inventors studied the effects of THC on pregnenolone in mutant mice (n=6-8 per group) in which the expression of the CB1 receptor was constitutively deleted. The examples show data obtained in the nucleus accumbens. THC-induced increase in pregnenolone was completely suppressed in mutant animals in which the CB1 receptor had been deleted in all types of cells or selectively in the neuronal population expressing the dopaminergic D1 receptor. In this mutant the CB1 receptor is deleted in most GABA neurons in the accumbens. The latest experiment indicates that in the brain, THC increases pregnenolone by acting on the CB1 receptor expressed by neurons.

Discussion

The data presented in the previous examples converge in supporting the hereby disclosed discovery that: "activation of the CB1 receptors in mammals induces the synthesis of pregnenolone and increase the concentration of this steroid in the body".

The data presented in the previous examples converge then in providing a generalized method for increasing pregnenolone concentrations in the body.

The converging evidence presented in the examples can be summarized as follow:

First, pregnenolone is dose-dependently increased by the administration of three different agonists of the CB1 receptor: THC, HU210 and Win55,212. In contrast, pregnenolone was not significantly increased by an agonist that has a higher affinity for the CB2 than for the CB1 receptor. The increase in pregnenolone concentrations induced by CB1 agonists was confirmed in two different species (the mouse and the rat) and was found both in the brain and in the plasma.

Second, the increase in pregnenolone induced by THC was suppressed by administration of a CB1 antagonist and was abolished in mutant animals lacking the CB1 receptor.

II. Pregnenolone Exerts a Negative-Feedback on the CB1 Receptor and Inhibits the Effects of CB1 Receptor Activation Example 7: THC-Induced Increase in Pregnenolone Provides a Negative Feed-Back on the Activation of the CB1 Receptor In these examples the inventors analyzed the potential functional role of the increase in pregnenolone induced by THC activation of the CB1 receptor. The inventors found that pregnenolone exerts a negative feed-back on the effects that are mediated by the stimulation of the CB1 receptor.

The activation of the CB1 receptor is usually identified by four effects, generally called the cannabinoid tetrade, which include: 1. hypolocomotion, 2. hypothermia, 3. catalepsy (impaired ability to initiate movements), and 4. analgesia. Accordingly, the injection of THC (3, 10, 15 mg/kg) to C57B1/6N (n=7-8 per group) induced a dose-dependent: i) decrease of locomotor activity in the open-field; ii) decrease of body temperature; iii) increase of the latency to initiate movement (increased catalepsy); and iv) an increase in the nociceptive threshold (FIG. 2A-D).

Since the dose of THC at which the tetrad is observed (between 3 and 15 mg/kg of THC) induces a strong increase in pregnenolone concentrations, the inventors analyzed the effects of the inhibitor of pregnenolone synthesis aminoglu-thetimide (AMG, 50 mg/kg, ip) injected 30 min before THC, behaviors were sequentially measured 30 min after THC injection. AMG strongly increased all the behavioural effect of THC (FIG. 2 A-D) and this enhancement was completely reversed by the exogenous injection of pregnenolone (6 mg/kg) (FIG. 2 E-H), demonstrating the dependence from pregnenolone of the observed effects of AMG administration. These data demonstrate that the secretion of pregnenolone induced by the activation of the CB1 receptor serves the function of inhibiting with a negative feedback loop the effects resulting from such an activation of the CB1.

Example 8: Pregnenolone Inhibits the Endocannabinoid Tetrad Induced by Activation of the CB1 Receptor by THC In these examples the inventors analyzed if the exogenous administration of pregnenolone could also inhibit the cannabinoid tetrad induced by THC. Pregnenolone administration (6 mg/kg) before THC and in the absence of AMG decreased all the behaviours of the THC-induced cannabinoid tetrad: locomotor activity, body temperature, catalepsy and pain threshold (FIG. 2 E-H). However, administration of pregnenolone per se in the absence of THC had no effect on locomotor activity, body temperature, catalepsy and pain threshold (FIG. 2 E-H).

Example 9: Pregnenolone Inhibits the Increase in Food Intake Induced by THC

To provide further examples of the ability of pregnenolone to inhibit the effects resulting from the activation of the CB1 receptors, the inventors then studied if pregnenolone (injected 30 min before THC) could also inhibit THC-induced increase in food intake.

THC has been shown to increase food intake in sated rats (0.5 mg/kg, n=7-8 per group) and in 24 hours food-deprived mice (n=7-8 per group 1 mg/kg). In sated rats (FIG. 3A) pregnenolone dose-dependently decreased THC-induced food intake with a statistically significant effect at 2 mg/kg. This dose also suppressed the increase in food intake induced by the injection of THC in mice (FIG. 3B). At this dose pregnenolone did not significantly modified basal food intake (FIG. 3 A, B).

Example 10: Pregnenolone Inhibits the Increase in Food Intake Induced by Food-Deprivation CB1 activation by endogenous endocannabinoid has been involved in the regulation of physiological food intake, i.e.

food intake not stimulated by exogenous CB1 agonists such as THC. The inventors then further investigated if pregnenolone administration was able to modify food intake in food deprived animals that did not received THC.

The inventors found that pregnenolone dose dependently decreased food intake in food-deprived mice (FIG. 3C), however the first statistically significant dose (6 mg/kg) was higher than the one (2 mg/kg) able to block THC-induced food intake.

Example 11: Pregnenolone Inhibits the Increase in Food Intake Induced by Food-Deprivation Through a CB1-Dependent Mechanism Many physiological systems regulate food intake. For this reason in this example the inventors verified if the reduction in food intake induced by pregnenolone in food-deprived animals that were not treated with THC was dependent on the CB1 receptor. The inventors studied the effects of a pre-treatment with the CB1 antagonist SR141716A (0.05 mg/kg, ip) on the reduction in food intake induced by pregnenolone in food-deprived animals. The inventors found that the inhibition induced by pregnenolone on food intake in food deprived animals was dependent on the CB1 receptors. Thus, the CB1 antagonist SR141716A administered to food-restricted mice 30 min before the administration of Pregnenolone suppressed the reduction in food intake induced by pregnenolone administration (FIG. 3D).

Example 12: Pregnenolone Inhibits Self-Administration of CB1 Agonists

In order to analyse the effects of pregnenolone administration on the positive reinforcing effect of CB1 activation that are related to the ability of THC to induce addiction, the inventors used the intravenous self-administration model performed in accordance to protocols previously described (Soria et al., 2006; Mendizabal et al., 2006). Intravenous self-administration is considered the best behavioural model of addiction. In this model animals learn to produce an operant response, in our case pocking the nose in a hole, in order to obtain an intravenous infusion of the drug. Mice readily self-administer the CB1 agonist WIN 55,212 (12.5 µg/kg per injection), showing a clear preference for the device in which responding trigger the infusion of this compound (active) in comparison to an inactive device in which responding had no scheduled consequences (inactive) (FIG. 4A). Administration with a latin square design of 2 or 4 mg/kg of pregnenolone=before the self-administration session profoundly reduced the self-administration of WIN55,212 (FIG. 4B). In addition pregnenolone administration also decreased the motivation to self-administer WIN55,212, as shown by the reduction in the break-point in a progressive ratio (PR) schedule (FIG. 4C). In this schedule animals are required to produce an increasing number of responses (ratio) to obtain one drug infusion, the break-point being the last ratio completed and is considered a reliable measure of the motivation for the drug. On PR session the response requirement to earn an injection escalated according to the following series: 1-2-3-5-12-18-27-40-60-90-135-200-300-450-675-1000.

Example 13: Pregnenolone Inhibits Memory Loss Induced by THC Administration

In this example the inventors further analyzed the ability of pregnenolone to inhibit the effects of CB1 activation. A supplementary effect of CB1 activation is the induction of memory impairments. This effect is related to one of the adverse effects of *cannabis* use: a cognitive impairment characterized by the loss of recent memories. CB1 receptor activation by THC (10 mg/kg) injected 10 min after training strongly impairs memory retention in an object recognition task in mice (FIG. 6).

Pre-treatment with pregnenolone injected immediately after training (6 mg/kg) strongly blunted the amnesic effect of 10 mg/kg of THC. However, pregnenolone (6 mg/kg) did not induce any change in memory retention when administered in the absence of THC (FIG. 6).

Example 14: Pregnenolone Inhibits the Increase in Dopaminergic Activity Induced by THC Administration In this example the inventors further analyzed the ability of pregnenolone to inhibit the effects of CB1 activation. *Cannabis* is thought to exercise its addictive properties by activating the CB1 receptor that in turn increase the release of the neurotransmitter dopamine in the nucleus accumbens, a brain region that regulate the shift from motivation to action. The effects of pregnenolone on the increase in dopaminergic activity produced by THC (FIG. 7) were studied recording two parameters in parallel: 1. the release of dopamine at the level of the dopaminergic terminals in the nucleus accumbens; and 2. the electrical activity of the dopaminergic neurons at the level of their cell body in the ventral tegmental area (VTA). Pregnenolone (2 m/kg injected subcutaneously, 30 min prior to THC) strongly blunted the increase in dopamine release and in the activity of the dopaminergic neurons induced by THC or cocaine was administered intravenously at exponentially increasing cumulative doses (0.15 to 1.2 mg/kg). After each dose, DA neuronal firing was recorded for 1 minute before the subsequent administration. (FIG. 7).

Example 15: Pregnenolone Inhibits the Increase in Dopaminergic Activity Induced by Cocaine Administration In this example the inventors further analyzed the ability of pregnenolone to inhibit the activation of the dopaminergic system. In the previous example pregnenolone was able to antagonize the hyperactivity of the dopaminergic system induced by THC. In the present example (FIG. 8) it is shown the pregnenolone (2 mg/kg injected subcutaneously, 30 min before cocaine) is also able to antagonize the increase in activity of the dopaminergic system induced by psychostimulants such as cocaine. Cocaine was administered intravenously at exponentially increasing cumulative doses (0.0125 to 0.8 mg/kg). After each dose, DA neuronal firing was recorded for 1 minute before the subsequent administration. This results are relevant to schizophrenia because the increase in dopaminergic activity induced by psychostimulants is considered one of the experimental models of psychosis. Thus, to the increase in dopamine induced by psychostimulants is attributed the development of acute psychosis that can occur after the use of these drugs in humans.

Example 16: Pregnenolone Inhibits Body Weight Gain and Fat Accumulation in Animals Submitted to a High Fat Diet In this example the inventors analyzed the ability of pregnenolone to inhibit the effects of CB1 activation in the context of obesity. The effects of pregnenolone on metabolic disorders were studied using the model of diet induced obesity (DIO) in mice. In this procedure animals are maintained on a high fat diet (60% of fat) which progressively induce obesity. After eight weeks on this diet which already induced overweight and excessive fat accumulation in these animals the treatment with pregnenolone was started for thirty days (once a day 2 mg/kg or 5 mg/kg, n=8). Pregnenolone decreased body weight with a delayed effect that appeared after 15 days of treatment (FIG. 9A) but did not modify food intake (FIG. 9B).

As a consequence pregnenolone effects on body weight seemed not due to a primary metabolic effect and not to a behavioral effect on food intake. This was confirmed by an analysis of body composition performed with magnetic resonance which revealed that under pregnenolone treatment there was a different effect on the fat and lean mass of the animals (FIG. 10). In control animals during the high fat diet the percentage of the fat mass progressively increased whilst the one of the lean mass decreased. When animal were treated with the highest dose of pregnenolone (5 mg/kg) the increase in fat mass was suppressed, whilst the decrease in lean mass was blunted.

The lack of effect on food intake on pregnenolone in the DIO model seems in contradiction with what observed using the fasting/refeeding model in which pregnenolone decreased food intake (FIG. 3). This could be due to the feeding condition, a high fat diet in the DIO model versus standard chow in the fasting/re-feeding model, or to a potential specific effect of pregnenolone on the burst of eating that is induced in fasted animals during the first hour of re-exposure to food. For this reason in the fasting/refeeding model food intake is classically evaluated during one hour, whilst in the DIO model food-intake is evaluated over 24 hours. In a subsequent experiment the effects of pregnenolone were studied over 24 hours also in the fasting/refeeding model. The results obtained confirmed the effects of pregnenolone during the first hour of re-feeding but no significant effect was seen over 24 hours. These data indicate a specific effect of pregnenolone on the burst of eating induced by fasting that strongly activates the endocannabinoid system and the CB1 receptor. This lack of effects of pregnenolone on 24 hours food intake is quite different from the known action of the reference CB1 orthosteric receptor antagonist rimonabant that has been previously shown to profoundly reduce food-intake over 24 hours. Similarly, during a high fat diet, rimonanbant has also been shown to reduce food-intake during the first week of treatment, whilst pregnenolone did not (FIG. 9A).

Example 17: Pregnenolone Inhibits the Increase in TNF-Alpha Induced by LPS

In this example the inventors further analyzed the ability of pregnenolone to inhibit the effects of CB1 activation in the context of inflammation and fibrosis. The activation of the CB1 receptor is involved in inflammatory and fibrotic process as shown but the fact that the inhibition of this receptor by ortosteric antagonists such as rimonabant decreases the increase in TNF-alpha induced by proinflammatory stimuli such as LPS. TNF-alpha is one of the cellular responses to inflammatory stimuli more involved in promoting fibrosis. Administration to mice of pregnenolone (6 mg/kg, subcutaneously) 30 min before the administration of LPS halved the increase in TNF-alpha measured 90 min after LPS administration (FIG. 11).

Example 18: Pregnenolone Inhibits the Effects of CB1 Activation on Synaptic Transmission In this example the inventors further analyzed the ability of pregnenolone to inhibit the effects of CB1 activation in the context of synaptic transmission. It is widely documented that activation of CB1 receptors suppresses synaptic transmission by inhibiting neurotransmitters release. This has been observed in many regions of the brain at both excitatory and inhibitory synapses. We assessed whether pregnenolone alters the ability of THC to inhibit excitatory synaptic transmission in the nucleus accumbens (NAc). Whole cell patch clamp recording were performed in the adult NAc and AMPAR-mediated EPSC were induced by electrical stimulation of local axons. Bath perfusion of THC reliably decreased EPSC amplitude in control slices (34.3±3.7% of inhibition). The effect of THC was significantly attenuated when slices were pre-treated with Pregnenolone 100 nM (15.1±1.8% of inhibition, p<0.001) (FIG. 12).

In order to test the effect of pregnenolone on a wider range of THC concentrations, we recorded fEPSP in NAc slices. Due to the possibility to achieved stable fEPSP measurements for several hours, this technique is ideally suited to perform dose-response curves and has previously been used to address CB1 receptor function (Robbe et al., 2001; Mato et al., 2004). Thus, AMPAR-mediated evoked fEPSP were recorded by electrically stimulating local axons. Bath perfusion of THC to control slices inhibited fEPSP in a dose-dependent manner (10 µM: 23.9±6.0%; 20 µM: 35.3±4.7%; 40 µM: 48.6±3.6%). Conversely, THC induced lesser inhibition of synaptic transmission in slices pre-incubated with pregnenolone 100 nM (10 µM: 11.1±3.2%; 20 µM: 22.7±2.7%; 40 µM: 34.6±3.1%; two way ANOVA neurosteroid factor p=0.001) (FIG. 13).

Altogether, these data demonstrate that the neurosteroid pregnenolone impairs the ability of THC to activate a CB1 receptors-dependent modulation of excitatory synaptic transmission.

Discussion:

The data presented in the previous examples converge in demonstrating the hereby disclosed discovery that: "the increase in pregnenolone concentrations induced in the body by the activation of the CB1 provides an endogenous negative feedback on the activity of the CB1 receptor. This negative feed-back is materialized by the fact that pregnenolone endogenously produced or exogenously administered antagonizes the effects of CB1 activation".

The data presented in the previous examples converge then in providing a general method for inhibiting the effects of the activation of the CB1 receptor by the administration of pregnenolone.

These converging evidences can be summarized as follow:

First, the inhibitory action of pregnenolone on CB1-mediated effects were of physiological relevance, since the endogenous increase in pregnenolone induced by CB1 activation, provided an endogenous negative feed-back that served the function of decreasing the effect of CB1 activation. Thus, when the production of pregnenolone induced by CB1 activation was blocked the behavioral effects of THC were increased.

Second, exogenous administration of pregnenolone was able to inhibit a large number of effects induced by the activation of the CB1 receptors: 1. hypolocomotion; 2. catalepsy; 3. hypotermia; 4. analgesia; 5. food intake in fasting-refeeding model; 7. Food intake induced by THC; 6. intravenous self-administration of a CB1 agonists; 7. memory loss induced by THC; _8. activation of the dopaminergic system by THC or cocaine; 9. fat accumulation and body weight gain in a model of obesity; 9. The production of TNF-alpha; 10. The inhibition of synaptic transmission induced by THC. Third, inhibitory action of pregnenolone on CB1-mediated effects was found in two different species: the rat and the mouse.

The convnering effects on these multiple parameters demonstrated here by the inventors are unique and non-predictable on the basis of previous knowledge of the effects of other known steroids that quite at the opposite are predicted to increase and not decrease the effects of the activation of the CB1 receptor. For example many steroids, such as pregnanolone, allopregnanolone and their derivatives have been described to facilitate the activation of the GABA receptor. These steroids should then increase the effects of CB1 activation since compounds that potentiate the activity of the GABA receptor have been shown to increase the effects of CB1 activation by THC (Bellocchio L et al., Nature Neurosci 2010, 13:281-3; Pertwee R G and Wickens A P. Neuropharmacology. 1991, 30:237-44; Pertwee R G, et al., Neuropharmacology. 1988 27:1265-70). Similarly on the basis of current knowledge also progesterone and progestinic compounds, other sex steroids and glucocorticoids are predicted to increase the effects of CB1 activation (Anaraki D K et al., Europ. J. Pharmacol, 2008, 586, 186-196; Rodriguez de Fonseca F, et al., Life Sci. 1993, 54: 159-170; Becker J B, Rudick C N. Pharmacol Biochem Behav. 1999, 64:53-7; Piazza P V and Le Moal M Brain Res Rev 1997, 25:359-72).

III. Pregnenolone is an Inhibitor of the CB1 Receptor with Less Side Effects and Less Non-Specific Actions than Orthosteric Antagonists of the CB1 and Other Neuroactive Steroids Example 19: Pregnenolone does not Modify the Orthosteric Binding to the CB1 Receptor The previous examples indicate that pregnenolone is able to inhibit all the studied effects of CB1 activation. Based on these observations in this example the inventors studied the potential interactions between pregnenolone and the CB1 receptor. The inventors analyzed if pregnenolone could act as an orthosteric antagonist of the CB1. This was not the case, since pregnenolone did not displace the orthosteric binding of the CB1 agonist [3H]CP55,940 to the CB1 receptor present on the plasma membrane of CHO cell (FIG. 14). Although pregnenolone does not act as an orthosteric antagonists preliminary evidence produced by the inventors indicate that it could act as an allosteric inhibitor.

Example 20: Pregnenolone does not Induce Anxiety Like Behaviors

One of the major side effects of orthosteric antagonists of the CB1 is the induction of behavioral side effect and in particular an axiodepressive state. These effects have been judged serious enough by regulatory authorities to suppress the market approval of the first CB1 orthosteric antagonist rimonabant. To substantiate the different safety profile of pregnenolone, its effects have been compared to the ones of the CB1 orthosteric antagonist/inverse agonist rimonabant (both drugs given subcutaneously) using an animal model of anxiety the elevated plus maze. This test has been chosen because an increase in anxiety was the principal undesirable side effect of this compound in humans. Mice were injected subcutaneously with either pregnenolone (1, 6, 10 mg/kg), rimonabant (10 mg/kg) or vehicle (at least n=7 per group) 30 min later they were placed in the central platform of the plus maze and the time spent and the number of entry in the open and closed arms recorder for 5 mins. This study (FIG. 15) confirmed anxiogenic effects of rimonabant as shown by the decrease in the number of entries and in the time spent in the open arm of the plus maze. In contrast pregnenolone induced no increase in anxiety (FIG. 15).

Example 21: Pregnenolone does not Modify the Activity of GABA-A Receptors

In this example the inventors tested the specificity of pregnenolone effects on other neurotransmitter receptors and in particular the GABA-A receptors. Thus, other active steroids such as allopregnanolone and pregnanolone have profound behavioral effects facilitating the activation of the GABA receptors.

In order to evaluate the effect of pregnenolone on the function of post-synaptic GABA we recorded mIPSC and compared its amplitude and decay time between groups. We observed that mIPSC amplitude and decay time were similar between controls (amplitude: 17.9±0.8 pA; decay time: 11.1±0.3 ms) and slices pre-treated with pregnenolone (100 nM and 1 μM, respectively; amplitude: 17.3±0.4 pA, 15.9±0.4 pA; decay time: 10.2±0.4 ms, 10.8±0.5 ms). As opposed to the lack of effect of pregnenolone, the neurosteroid allopregnanolone, known for being a modulator of GABA-A receptors, significantly modified mIPSC properties (100 nM and 1 μM, respectively; amplitude: 15.9±0.5 pA, 20.2±1.2 pA, p<0.001; decay time: 13.6±0.7 ms, 22.7±2.3 ms, p<0.0001) (FIG. 16).

In conclusion, this data suggest that GABA-A-mediated synaptic currents are not modulated by the neurosteroid pregenenolone. This data then confirm, as previously shown (U.S. Pat. No. 5,232,917), that the C3 beta position of pregnenolone suppresses the effect on the GABA receptor. The inventor discover here that the C3 beta position confer instead the property to inhibit the activation of the CB1 receptor.

Example 22: Pregnenolone does not Modify the Activity of the Glutamate Receptors In this example the inventors tested the specificity of pregnenolone effects on other neurotransmitter receptors and in particular the NMDA and AMPA receptors. Thus, other active steroids such as DHEA and DHEA sulphate are supposed to induce behavioral effect by modifying the activity of the glutamate receptors. To evaluate the effect of pregnenolone on AMPA receptors currents, we decided to record action potentials independent mEPSC. In this case, synaptic currents arise from stochastic quantal release of neurotransmitters and assuming that neurosteroids do not change the content of synaptic vesicles, the amplitude and kinetics of the recorded mEPSC depends on the function of the post-synaptic receptors.

We found that pregnenolone did not modify AMPAR function in the adult NAc (FIG. 17A). Thus, AMPAR-mediated mEPSC from controls and pregnenolone (100 nM) treated slices showed similar amplitudes (controls: 14.4±0.8 pA, pregnenolone: 15.7±0.7 pA, p=0.25) and decay times (controls: 4.76±0.08 ms, pregnenolone: 4.62±0.06 ms, p=0.21).

To quantify NMDA receptors-mediated currents we used a different strategy. Because of its slow kinetics and voltage dependence, the isolation of NMDAR-mediated mEPSC is not as reliable as for AMPAR-mediated currents. Thus, we decided to record whole cell currents in response exogenously applied NMDA. In NAc PN voltage-clamped at −30 mV, bath perfusion of NMDA 25 µM for 1 minute induced an inward current of similar magnitude in control slices (115±15.5 pA) and in slices pre-treated with pregnenolone (100 nM: 107±9.6 pA; 1 µM: 108.9±12.5 pA; p=0.91) (FIG. 17 B).

Overall, these experiments show that pregnenolone does not affect the function of the main post-synaptic ionotropic glutamatergic receptors in the rodent adult NAc. These data also indicate that the substitution of the ketone in position 17 of the steroid ring with an ethanone (methylketone) supress activity on the NMDA and AMPA receptors and confer the property to inhibit the activation of the CB1 receptor.

Discussion:

The data presented in the previous examples converge in demonstrating the hereby disclosed discovery that: "pregnenolone act as a inhibitor of the human CB1 receptor with a pharmacological profile different from orthosteric antagonist and from other neuroactive steroids that indicate that pregnenolone will have less unspecific and undesiderable effects than orthosteric antagonists of the CB1 and other neuroactive steroids.

The data presented in the previous examples converge then in providing a general method for inducing an inhibition of the activity of the CB1 receptor by the administration of pregnenolone. Consequently the data presented in the previous examples converge in providing a general method to treat or alleviate all pathologies that are related to the activation of the CB1 receptor and/or pathologies that can benefit from the inhibition of the CB1 receptors by administration of pregnenolone without the potential side effects of orthosteric antagonists of the CB1 and of other active steroids including but not limited to DHEA, Allopregnanolone and pregnanolone These converging evidences can be summarized as follow:

First, pregnenolone does not modify the binding of an orthosteric agonist, whilst it inhibits the effects resulting from the activation of the CB1 receptor. This profile could correspond to the one of an allosteric inhibitor.

Second, pregnenolone differently from orthosteric antagonist does not induce anxiety (example 20) nor reduce food-intake in an obesity model although it reduce fat accumulation (example 18). The pure metabolic effects of pregnenolone devoid of a modification of food intake also predict fewer side effects for pregnenolone. Study on the effects of ortostheric antagonists of the CB1, such as rimonabant, on body weight and metabolism have shown that these compounds act on metabolism with a double action the first due to the weight loss that results from a decrease in food intake (approximately 50% of the effects) and the second from a direct metabolic effect. The side effects of CB1 orthosteric receptor antagonists, and in particular the increase in depression, likely involve their behavioral effects on food intake. Thus, it is well known that in the obese population all manipulations, pharmacological, surgical, or behavioral treatment, that reduce food intake also induce in up to 5% of the subjects serious behavioral disturbances and in particular depression.

Finally, pregnenolone differently from other neuroactive steroids is devoid of effects on the GABA and glutamate receptors. This is important in predicting that pregnenolone will not have the side effects of some of these steroids which can induce important modifications of weakfulness inducing sedation, impairment of memory performances and motor behavior.

IV. Pregnenolone Derivatives for which the Transformation in Other Active Steroids Derived from Pregnenolone has been Limited Act as Inhibitors of the Effects of CB1 Receptor Activation

Example 23: Derivatives of Pregnenolones for which the Transformation in Downstream Active Steroids is Limited do not Produce Allopregnanolone and Epiallopregnanolone In Vivo As examples of the compound described in the general formula A, the inventors tested herein three compounds that were obtained by:

1. The substitution of the OH group at C3 by a fluorine atom, which generated the compound named 3-Fluoropregnenolone (CP1).

2. The quaternization of C17 with a methyl group, which generated the compound named 17-methylpregnenolone (CP2).

3. The substitution of the OH group at C3 by a fluorine atom and the quaternization of C17 with a methyl group, which generated the compound named 3-fluoro-17-methylpregnenolone (CP3).

None of the modified pregnenolone derivatives (compound: CP1, CP2, CP3), injected at high doses (50 mg/kg, n=6-7 per group)) to wistar rat, induced the production of allopregnanolone and epiallopregnanolone (FIG. 18), whilst allopregnanolone and epiallopregnanolone increased after the injection of pregnenolone (50 mg/kg) (FIG. 18). The concentrations of allopregnanolone and epiallopregnanolone were measured in nucleus accumbens of individual animal by GC/MS 30 min after the injections.

Example 24: Derivatives of Pregnenolones for which the Transformation in Downstream Active Steroids In Vitro is Limited In this example the inventors further analyzed the metabolism of pregnenolone derivatives using an in vitro test in CHO cells. These cells derived from the ovary have all the enzymes needed to metabolize pregnenolone in down stream steroids. In particular administration of pregnenolone (1 µM) to these cells for 48 hours produced a significant increase in Allopregnanolone, Epiallopregnanolone and a much smaller increase in THDOC in the culture medium (Table 1A). A total of 55 compounds plus pregnenolone were tested, of these compounds only 25 had an absent or significantly reduced metabolism in down stream active steroids (Table 1B-D, Table 2A,B). The remaining compounds were more or less metabolized in one or several of the downstream steroids of pregnenolone, such as Allopregnanolone, Epiallopregnanolone, THDOC, testosterone and DHEA.

TABLE 1

Pregnenolone derivatives with reduced metabolism in CHO cells.

Table 1 A: Pregnenolone metabolism

|  |  | ALLO | EPIALLO | THDOC | PREG | DHEA | TESTO |
|---|---|---|---|---|---|---|---|
| Control cell cultures | Steroid levels pg/ml | 0.00 | 0.00 | 27.96 | 96.92 | 0.00 | 0.00 |
| Pregnenolone (1 μM) treated cells |  | 3529.99 | 16963.84 | 77.47 | 11440.66 | 0.00 | 0.00 |

Table 1 B: Not detectable metabolism

| Comp. N° | Name | Structure | % changes from Pregnenolone treated cells | | | | pg/ml | |
|---|---|---|---|---|---|---|---|---|
|  |  |  | ALLO | EPIALLO | THDOC | PREG | DHEA | TESTO |
| 14 | 4-Pregnen-17α,20α-diol-3-one |  | −100.00 | −100.00 | −100.00 | −100.00 | 0.00 | 0.00 |
| 24 | 20-Deoxy-pregnenolone |  | −100.00 | −100.00 | −100.00 | −100.00 | 0.00 | 0.00 |
| 74 | 17α-Benzyl-3β-fluoro-pregnanolone |  | −100.00 | −100.00 | −100.00 | −100.00 | 0.00 | 0.00 |
| 77 | 5β-Pregnan-3β-ol-20-one (Epipregnanolone) |  | −100.00 | −100.00 | −100.00 | −100.00 | 0.00 | 0.00 |

TABLE 1-continued

Pregnenolone derivatives with reduced metabolism in CHO cells.

Table 1C: Decrease in Allo and Epiallo > 99%

| Comp. N° | Name | Structure | % changes from Pregnenolone treated cells | | | | pg/ml | |
|---|---|---|---|---|---|---|---|---|
| | | | ALLO | EPIALLO | THDOC | PREG | DHEA | TESTO |
| 40 | 17α-Methyl-progesterone | | −99.70 | −99.83 | −100.00 | −100.00 | 0.00 | 0.00 |
| 42 | 3β-Benzyl-oxy-17α-methyl-pregnenolone | | −99.87 | −99.94 | −94.10 | −100.00 | 0.00 | 0.00 |
| 69 | 17α-Allyl-3β-methoxy-pregnenolone | | −99.59 | −100.00 | −100.00 | −100.00 | 0.00 | 0.00 |
| 73 | 17α-Benzyl-progesterone | | −99.28 | −99.93 | −100.00 | −100.00 | 0.00 | 0.00 |
| 67 | 20-Methyl-amino-5-pregnen-3β-ol | | −99.20 | −99.79 | −100.00 | −99.79 | 0.00 | 0.00 |

TABLE 1-continued

Pregnenolone derivatives with reduced metabolism in CHO cells.

Table 1 D: Decrease in Allo and Epiallo > 97%

| Comp. N° | Name | Structure | % changes from Pregnenolone treated cells |||| pg/ml ||
|---|---|---|---|---|---|---|---|---|
| | | | ALLO | EPIALLO | THDOC | PREG | DHEA | TESTO |
| 41 | 3β-Benzyl-oxy-preg-nenolone | | −98.82 | −99.88 | −100.00 | −99.35 | 0.00 | 0.00 |
| 12 | 4-Pregnen-3β,20α-diol | | −98.64 | −97.17 | −100.00 | −98.80 | 0.00 | 0.00 |
| 18 | 4-Pregnen-20α-ol-3-one | | −98.16 | −96.80 | −100.00 | −100.00 | 0.00 | 0.00 |
| 65 | 17α-Benzyl-preg-nenolone | | −97.26 | −99.72 | −100.00 | −100.00 | 0.00 | 0.00 |
| 72 | 3-Azido-preg-nenolone | | −97.76 | −99.58 | −100.00 | −100.00 | 0.00 | 0.00 |

Results are expressed as percentage changes from CHO cells treated with pregnenolone (table 2A) or as pg/ml (0 = concentrations below the detection limit).
ALLO = Allopregnanolone,
EPIALLO = epiallopregnanolone,
PREG = pregnenolone,
TESTO = testosterone.

TABLE 2

Pregnenolone derivatives with reduced metabolism in CHO cells.

Table 2A: Decrease in Allo. and Epiallo. > 97% and/or decrease in THDOC > 29%

| Comp. N° | Name | Structure | % changes from Pregnenolone treated cells | | | | pg/ml | |
|---|---|---|---|---|---|---|---|---|
| | | | ALLO | EPIALLO | THDOC | PREG | DHEA | TESTO |
| 32 | 17α-Ethyl-pregnenolone | 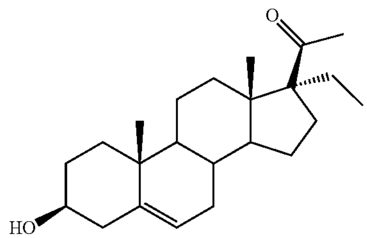 | −97.54 | −98.72 | −88.33 | −100.00 | 0.00 | 0.00 |
| 1 | 3β-Fluoro-pregnenolone | 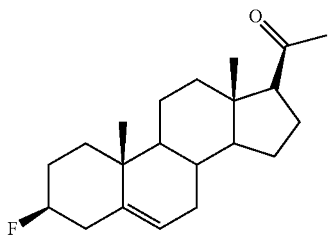 | −99.38 | −99.93 | −81.87 | −100.00 | 0.00 | 0.00 |
| 3 | 3β-Fluoro-17α-methyl-pregnenolone | 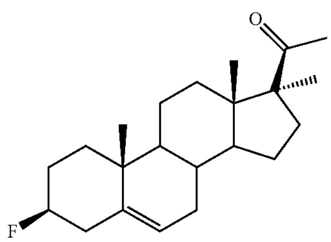 | −99.56 | −100.00 | −71.63 | −100.00 | 0.00 | 0.00 |
| 39 | 5,16-Pregnadien-20-one | 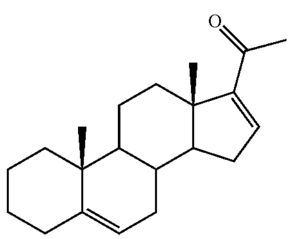 [SMILES: CC(=O)C1=CCC2C3CC=C4CCCC[C@]4(C)C3CC[C@]12C] | −100.00 | −100.00 | −29.14 | −100.00 | 0.00 | 0.00 |

Table 2B: Decrease in Allo and Epiallo > 96% and no decrease in THDOC

| Comp. N° | Name | Structure | % changes from Pregnenolone treated cells | | | | pg/ml | |
|---|---|---|---|---|---|---|---|---|
| | | | ALLO | EPIALLO | THDOC | PREG | DHEA | TESTO |
| 60 | 5β-Pregnan-3,20-dione | 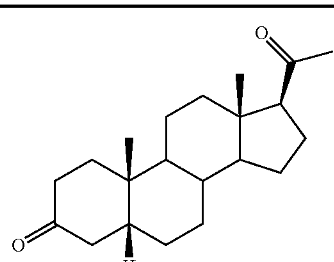 | −100.00 | −100.00 | 78.80 | −99.72 | 0.00 | 0.00 |

TABLE 2-continued

Pregnenolone derivatives with reduced metabolism in CHO cells.

| # | Name | Structure | | | | | |
|---|---|---|---|---|---|---|---|
| 36 | 17-Methoxy-pregnenolone | | −100.00 | −100.00 | 86.37 | −100.00 | 0.00 | 0.00 |
| 35 | 3β-Methoxy-17α methyl-pregnenolone | | −99.98 | −99.96 | 14.83 | −100.00 | 0.00 | 0.00 |
| 20 | 5-Pregnen-3β,20α-diol | | −97.11 | −96.41 | 35.54 | −97.11 | 0.00 | 0.00 |
| 63 | 17α-Benzyl-3β-benzyloxypregnenolone | | −99.01 | −99.84 | 46.63 | −99.87 | 0.00 | 0.00 |
| 70 | 17α-Benzyl-3β-methoxy-pregnenolone | | −99.75 | −100.00 | 12.76 | −99.76 | 0.00 | 0.00 |
| 2 | 17α-Methyl-pregnenolone | | −99.26 | −98.89 | 34.17 | −95.70 | 0.00 | 0.00 |

Results are expressed as percentage changes from CHO cells treated with pregnenolone (table 2A) or as pg/ml (0 = concentrations below the detection limit).
ALLO = Allopregnanolone,
EPIALLO = epiallopregnanolone,
PREG = pregnenolone,
TESTO = testosterone.

As can be seen in table 3 current knowledge on steroid metabolism does not allow to fully predicting which modifications of pregnenolone will reduce notably metabolism and which will not. For example an alpha-hydroxyl group in C20 reduced metabolism whilst a beta-hydroxyl group in C20 did not. Similarly compounds with a beta-hydrogen in C5 had a reduced metabolism whilst C5 alpha compounds were strongly metabolized. Also selective groups in C3 and C17 or some specific combination blocked metabolism.

TABLE 3

Comparison of the modifications of pregnenolone derivatives that reduced or maintained significant metabolism in downstream active steroids.

Table 3 A Modifications in position C3

| Reduced metabolism | | | Metabolized | | |
| --- | --- | --- | --- | --- | --- |
| N° | Name | Structure | N° | Name | Structure |
| 41 | 3β-Benzyl-oxy-pregnenolone | | 33 | 3β-Methoxy-pregnenolone | |
| 72 | 3-Azido-pregnenolone | | 66 | 3β-Amino-pregnenolone | |
| 1 | 3β-Fluoro-pregnenolone | | 34 | 3β-Ethoxy-pregnenolone | |
| | | | 55 | 3β-Acetoxy-pregnenolone | |
| | | | 25 | Pregnenolone hemi-succinate | |

TABLE 3-continued

Comparison of the modifications of pregnenolone derivatives that reduced or maintained significant metabolism in downstream active steroids.

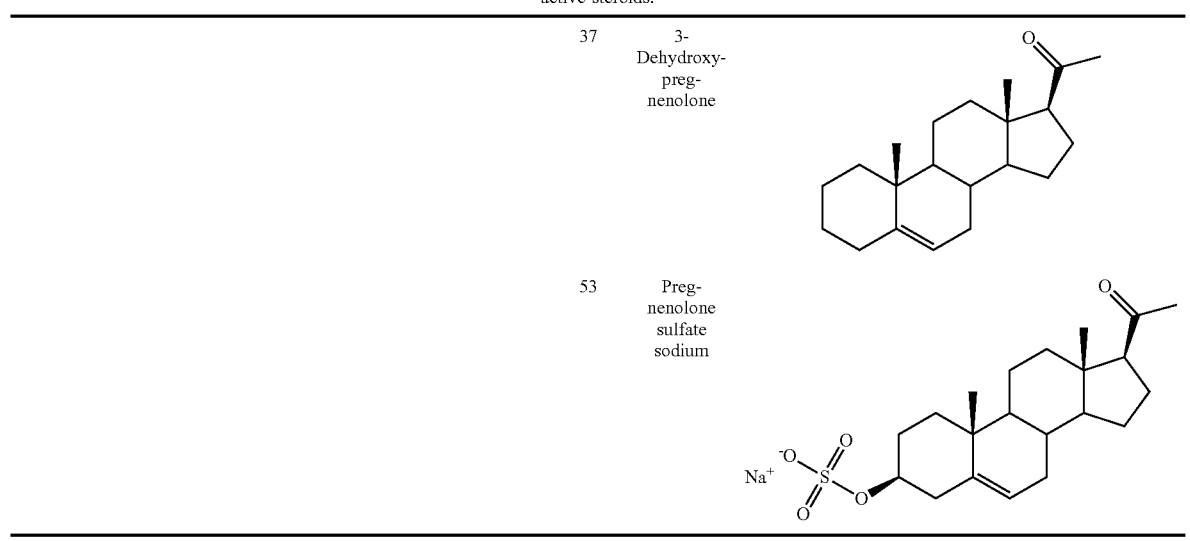

| N° | Name | Structure | N° | Name | Structure |
|---|---|---|---|---|---|
| 14 | 4-Pregnen-17α,20α-diol-3-one | | 13 | 4-Pregnen-3β,20β-diol | |
| 12 | 4-Pregnen-3β,20α-diol | | 15 | 4-Pregnen-17α,20β-diol-3-one | |
| 18 | 4-Pregnen-20α-ol-3-one | | 19 | 4-Pregnen-20β-ol-3-one | |
| 20 | 5-Pregnen-3β,20α-diol | | 21 | 5-Pregnen-3β,20β-diol | |

Table 3 B Modifications in position C20 alpha or beta

Reduced metabolism | Metabolized

TABLE 3-continued

Comparison of the modifications of pregnenolone derivatives that reduced or maintained significant metabolism in downstream active steroids.

Table 3 C Modifications in position C5

| | Reduced metabolism | | | Metabolized | |
|---|---|---|---|---|---|
| N° | Name | Structure | N° | Name | Structure |
| 77 | 5β-Pregnan-3β-ol-20-one (Epipregnanolone) | | 8 | 5α-Pregnan-3β,20α-diol | |
| 60 | 5β-Pregnan-3,20-dione | | 10 | 5α-Pregnan-3α-ol-20-one hemisuccinate (Allopregnanolone hemisuccinate) | |
| | | | 11 | 5α-Pregnan-3β-ol-20-one (Epiallopregnanolone) | |
| | | | 17 | 4-Pregnen-3β-ol-20-one | |
| | | | 29 | 5α-Pregnan-3,20-dione | |

TABLE 3-continued

Comparison of the modifications of pregnenolone derivatives that reduced or maintained significant metabolism in downstream active steroids.

| | | |
|---|---|---|
| 46 | 5α-Pregnan-3α-ol-20-one (Allopregnanolone) | 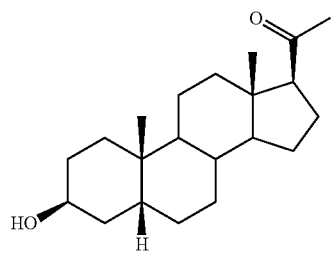 [SMILES: CC(=O)[C@H]1CCC2C3CC[C@@H]4C[C@@H](O)CC[C@]4(C)C3CC[C@@]21C] |
| 47 | Progesterone | 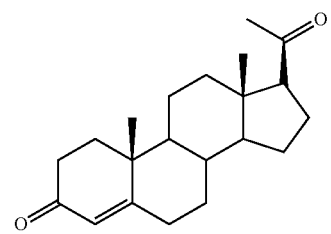 |

Table 3 D Modifications of the bound C16-C17 or of position C16

| Reduced metabolism | | | Metabolized | | |
|---|---|---|---|---|---|
| N° | Name | Structure | N° | Name | Structure |
| 39 | 5,16-Pregnadien-20-one | ![structure] | 6 | 5,16-Pregnadien-3β-ol | ![structure] |
| | | | 7 | 5,16-Pregnadien-3β-ol-20-one | ![structure] |
| | | | 38 | 5,16-Pregnadien-3β,20-diol | ![structure] |

TABLE 3-continued

Comparison of the modifications of pregnenolone derivatives that reduced or maintained significant metabolism in downstream active steroids.

Table 3 E Modifications in position C20 & C21

| Reduced metabolism | | | Metabolized | | |
|---|---|---|---|---|---|
| N° | Name | Structure | N° | Name | Structure |
| 24 | 20-Deoxy-pregnenolone | 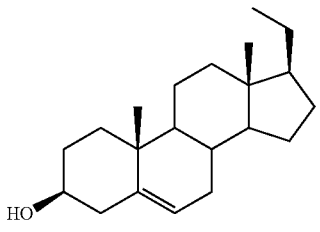 [SMILES: CC[C@H]1CCC2C3CC=C4C[C@@H](O)CC[C@]4(C)C3CC[C@@]21C] | 52 | 4-Pregnen-21-ol-3,20-dione | 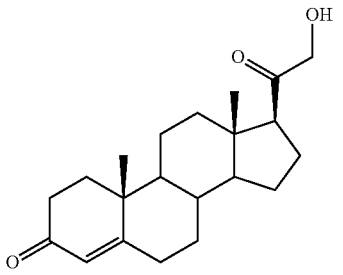 [SMILES: C[C@]12CCC(=O)C=C1CCC1C2CC[C@@]2(C)C1CC[C@@H]2C(=O)CO] |
| 67 | 20-Methyl-amino-5-pregnen-3β-ol | 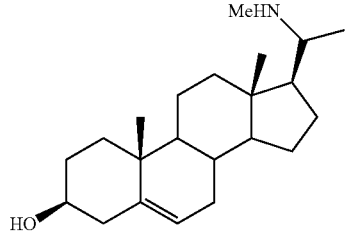 [SMILES: CNC(C)[C@H]1CCC2C3CC=C4C[C@@H](O)CC[C@]4(C)C3CC[C@@]21C] | 26 | 5-Pregnen-3β,21-diol-20-one | 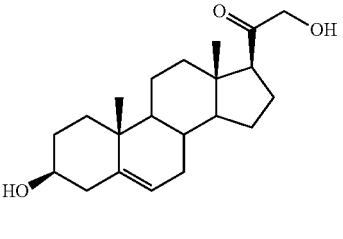 [SMILES: C[C@]12CC[C@H](O)CC1=CCC1C2CC[C@@]2(C)C1CC[C@@H]2C(=O)CO] |
| | | | 76 | 5α-Pregnan 3β,21-diol-20-one | 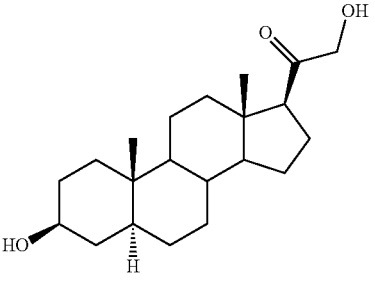 [SMILES: C[C@]12CCC3C(CC[C@H]4C[C@@H](O)CC[C@]34C)C1CC[C@@H]2C(=O)CO] |
| | | | 75 | 5α-Pregnan-3α,21-diol-20-one | 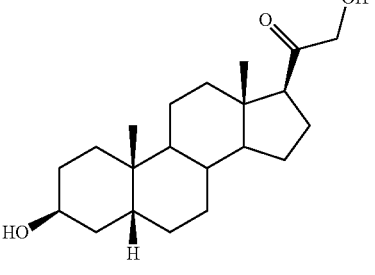 |
| | | | 50 | 5-Androsten-3β-ol-17-one (DHEA) | 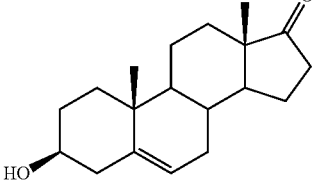 |

TABLE 3-continued

Comparison of the modifications of pregnenolone derivatives that reduced or maintained significant metabolism in downstream active steroids.

Table 3 F Modifications in position C17 and C3

| | Reduced metabolism | | | Metabolized | |
|---|---|---|---|---|---|
| N° | Name | Structure | N° | Name | Structure |
| 2 | 17α-Methyl-pregnenolone | | 71 | 17-Ethoxy-pregnenolone | |
| 65 | 17α-Benzyl-pregnenolone | | 22 | 17α-Hydroxy-pregnenolone | |
| 32 | 17α-Ethyl-pregnenolone | | 64 | 17α-Allyl-pregnenolone | |
| 36 | 17-Methoxy-pregnenolone | | 23 | 17α-Hydroxy-pregnenolone hemi-succinate | |
| 74 | 17α-Benzyl-3β-fluoro-pregnenolone | | | | |
| 73 | 17α-Benzyl-progesterone | | | | |

TABLE 3-continued
Comparison of the modifications of pregnenolone derivatives that reduced or maintained significant metabolism in downstream active steroids.
| | | |
|---|---|---|
| 63 | 17α-Benzyl-3β-benzyloxy-pregnenolone | |
| 70 | 17α-Benzyl-3β-methoxy-pregnenolone | |
| 42 | 3β-Benzyloxy-17α-methyl-pregnenolone | |
| 40 | 17α-Methyl-progesterone | |
| 3 | 3β-Fluoro-17α-methyl-pregnenolone | |
| 35 | 3β-Methoxy-17α-methyl-pregnenolone | |
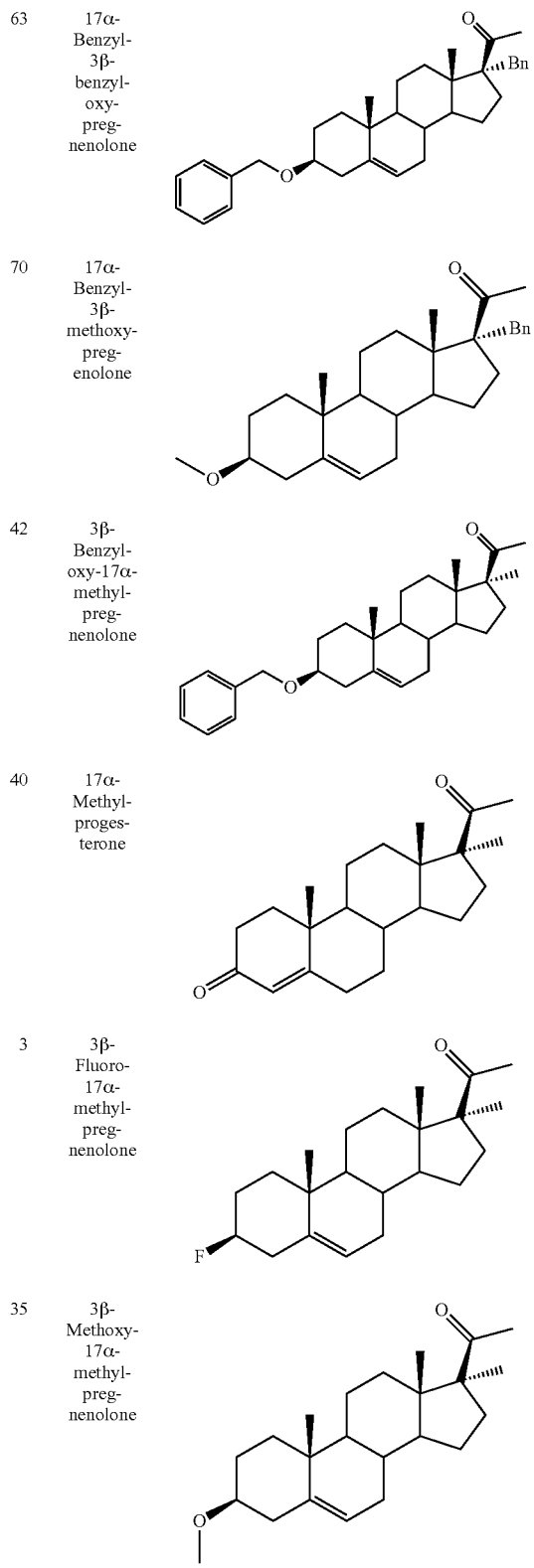

TABLE 3-continued

Comparison of the modifications of pregnenolone derivatives that reduced or maintained significant metabolism in downstream active steroids.

| 69 | 17α-Allyl-3β-methoxy-pregnenolone | 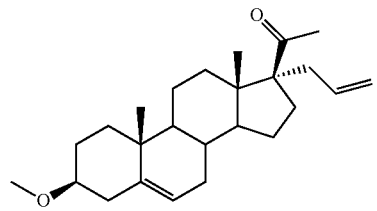 [SMILES: C=CC[C@]1(C(C)=O)CCC2C3CC=C4C[C@@H](OC)CC[C@]4(C)C3CC[C@@]21C] |

Example 25: Derivatives of Pregnenolones for which the Transformation in Downstream Active Steroids is Limited Inhibit the Effects of CB1 Receptor Activation As examples of the compound described in the general formula A, the inventors tested in the hereby presented examples the effect on food intake of compounds 3-Fluoropregnenolone, 17-methylpregnenolone, 3-fluoro-17-methylpregnenolone in rat or mice after stimulation with THC and/or after food deprivation. The compounds 3-Fluoropregnenolone, 17-methylpregnenolone, 3-fluoro-17-methylpregnenolone were able to inhibit the effects of CB1 activation on food intake. Compound 17-methylpregnenolone seemed more effective than pregnenolone and 3-Fluoropregnenolone and 3-fluoro-17-methylpregnenolone in inhibiting the effects of the activation of the CB1 receptor (FIG. 19). Compound 17-methylpregnenolone was able to decrease significantly the increase in food intake induced by THC in rats, whilst only a tendency to decrease food intake was observed for the other two compounds (FIG. 19A). In food-restricted mice all compounds decreased food intake. However, a statistically significant effects was obtained at the lowest dose (4 mg/kg) for compound 17-methylpregnenolone, whilst 6 mg/kg were needed for reaching statistical significance with pregnenolone and 3-Fluoropregnenolone and 3-fluoro-17-methylpregnenolone (FIG. 19B). Finally, THC-induced increase in food intake in mice was decreased by all compounds at (2 mg/kg) in mice (FIG. 19C). A dose response function for THC-induced increase in food-intake showed that both pregnenolone and 17-methylpregnenolone inhibited this behavior at 1 mg/kg, whist 0.5 mg/kg dose was ineffective.

Other pregnenolone derivatives (Table 4) for which the metabolism in downstream active steroids was reduced were tested for their ability to inhibit: 1. effects of the THC-induced cannabinoid tetrade (decrease in body temperature and in locomotor activity, (THC 10 mg/kg, compounds 6 mg/kg 15-30 min before THC) that is recognized as a sound method to evaluate the activation of the CB1 receptor; 2. THC-induced increase in food intake a typical effect of CB1 activation (THC between 0.5 and 1 mg/kg, compounds between 2 and 4 mg/kg 30 min before THC); 3. the increase in TNFalpha induced by LPS, another effects typical of CB1 antagonists (compounds 6 mg/kg 15 min before LPS). For each compound and each test independent groups of animals were used (at least n=6 per compound/per test).

TABLE 4

Inhibition of CB1 activation by pregnenolone derivatives with reduced metabolism.

Table 4 A Compounds with a beta-hydroxyl group in position C3

| | | | CB1 Antagonism | | | |
|---|---|---|---|---|---|---|
| | Compounds with reduced metabolism | | % Inhibition temperature decrease | % increase in motor activity | % Inhibition of THC-Induced food intake | % Inhibition of TNF-α |
| N° | Name | Structure | | | | |
| 77 | 5β-Pregnan-3β-ol-20-one (Epipregnanolone) | 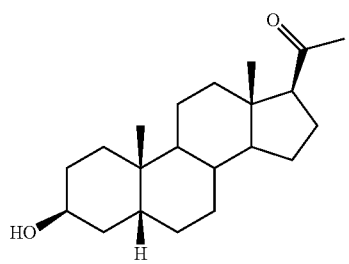 [SMILES: CC(=O)[C@H]1CCC2C3CC[C@@H]4C[C@@H](O)CC[C@]4(C)C3CC[C@@]21C] | 70%, P < 0.0001 | 177%, P < 0.02 | ≥100%, P < 0.01 | 76%, P < 0.003 |

TABLE 4-continued
Inhibition of CB1 activation by pregnenolone derivatives with reduced metabolism.
| 2 | 17α-Methyl-pregnenolone | 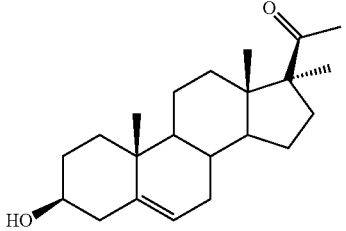 | 43%, P < 0.001 | 240%, P < 0.01 | ≥100%, P < 0.001 | 60%, P < 0.02 |
| 65 | 17α-Benzyl-pregnenolone | 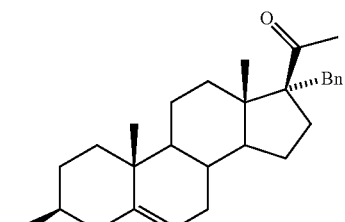 | 53%, P < 0.003 | 142%, P < 0.03 | ≥100%, P < 0.001 | 65%, P < 0.01 |
| 36 | 17-Methoxy-pregnenolone | 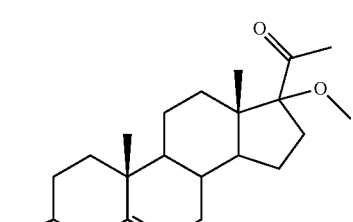 | 54%, P < 0.001 | 326%, P < 0.001 | ≥100%, P < 0.003 | 37%, P < 0.04 |
| 12 | 4-Pregnen-3β,20α-diol | 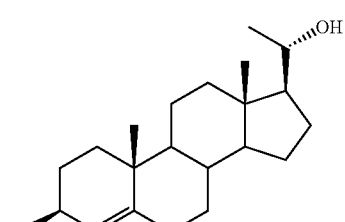 | 42%, P < 0.004 | 100%, P < 0.16 | ≥100%, P < 0.001 | 81%, P < 0.002 |
| 20 | 5-Pregnen-3β,20α-diol | 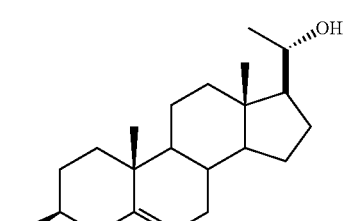 | 34%, P < 0.04 | 123%, P < 0.04 | 85%, P < 0.03 | 65%, P < 0.01 |

TABLE 4-continued

Inhibition of CB1 activation by pregnenolone derivatives with reduced metabolism.

Table 4 B Modifications in position C17, C20 that decrease activity

| | | | CB1 Antagonism | | | |
|---|---|---|---|---|---|---|
| | Compounds with reduced metabolism | | % Inhibition temperature | % increase in motor | % Inhibition of THC-Induced | % Inhibition |
| N° | Name | Structure | decrease | activity | food intake | of TNF-α |
| 32 | 17α-Ethyl-pregnenolone | | 12%, $P > 0.25$ | −2%, $P > 0.25$ | nt | 64%, $P < 0.02$ |
| 24 | 20-Deoxy-pregnenolone | | 25%, $P < 0.08$ | 33%, $P > 0.20$ | nt | 34%, $P > 0.14$ |
| 67 | 20-Methyl-amino-5-pregnen-3β-ol | | 28%, $P < 0.05$ | −20%, $P > 0.35$ | nt | nt |

Table 4 C Modifications in position C3 that maintain activity

| | | | CB1 Antagonism | | | |
|---|---|---|---|---|---|---|
| | Compounds with reduced metabolism | | % Inhibition temperature | % increase in motor | % Inhibition of THC-Induced | % Inhibition |
| N° | Name | Structure | decrease | activity | food intake | of TNF-α |
| 41 | 3β-Benzyl-oxypregnenolone | | 38%, $P < 0.001$ | 106%, $P < 0.03$ | nt | 62%, $P < 0.01$ |

TABLE 4-continued

Inhibition of CB1 activation by pregnenolone derivatives with reduced metabolism.

| 72 | 3-Azido-pregnenolone | | 34%, P < 0.05 | 145%, P < 0.05 | ≥100%, P < 0.001 | 61%, P < 0.02 |
|---|---|---|---|---|---|---|
| 1 | 3β-Fluoro-pregnenolone | | nt | nt | ≥100%, P < 0.01 | 58%, P < 0.02 |
| 3 | 3β-Fluoro-17α-methyl-pregnenolone | | nt | nt | ≥100%, P < 0.01 | nt |
| 39 | 5,16-Pregnadien-20-one | | 56%, P < 0.001 | 309%, P < 0.001 | ≥100%, P < 0.02 | 46%, P < 0.03 |

Table 4 D Modifications in position C3 that decrease activity

| | Compounds with reduced metabolism | | CB1 Antagonism | | | |
|---|---|---|---|---|---|---|
| N° | Name | Structure | % Inhibition temperature decrease | % increase in motor activity | % Inhibition of THC-Induced food intake | % Inhibition of TNF-α |
| 70 | 17α-Benzyl-3β-methoxy-pregnenolone | | 8%, P > 0.49 | 2%, P > 0.48 | nt | nt |

TABLE 4-continued

Inhibition of CB1 activation by pregnenolone derivatives with reduced metabolism.

| 35 | 3β-Methoxy-17α-methyl-pregnenolone | | 33%, P < 0.01 | −32%, P > 0.24 | nt | 57%, P < 0.05 |
| 69 | 17α-Allyl-3β-methoxy-pregnenolone | | 4%, P > 0.39 | −49%, P > 0.1 | nt | nt |

Table 4 E Compounds with a ketone in position C3

| | | | CB1 Antagonism | | | |
| --- | --- | --- | --- | --- | --- | --- |
| | Compounds with reduced metabolism | | % Inhibition temperature decrease | % increase in motor activity | % Inhibition of THC-Induced food intake | % Inhibition of TNF-α |
| N° | Name | Structure | | | | |
| 14 | 4-Pregnen-17α,20α-diol-3-one | | 45%, P < 0.001 | 277%, P < 0.004 | 70%, P < 0.06 | 65%, P < 0.01 |
| 18 | 4-Pregnen-20α-ol-3-one | | 25%, P < 0.04 | 146%, P < 0.1 | 30%, P > 0.25 | 65%, P < 0.01 |
| 40 | 17α-Methyl-progesterone | | 18%, P < 0.02 | 57%, P < 0.21 | 74%, P < 0.07 | 57%, P < 0.02 |

TABLE 4-continued

Inhibition of CB1 activation by pregnenolone derivatives with reduced metabolism.

| 60 | 5β-Pregnan-3,20-dione | 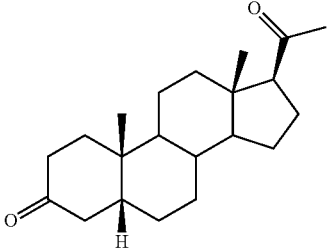 [SMILES: CC(=O)[C@H]1CCC2C3CC[C@@H]4CC(=O)CC[C@]4(C)C3CC[C@@]21C] | 66%, $P < 0.0001$ | 70%, $P < 0.05$ | ≥100%, $P < 0.002$ | 77%, $P < 0.003$ |

Mice (at least n = 6 per group) treated with pregnenolone derivatives (between 2 and 6 mg/kg) were compared to the appropriate controls treated with vehicle. Changes in body temperature and locomotor activity were studied after injection of 10 mg/kg of THC, food intake after injection of THC between 0.5 and 1 mg/kg, TNFα after systemic injection of LPS.
nt = not tested.
Statistics were performed using Student's t-test.

For compounds that maintained a beta-hydroxyl group in position C3, the substitution in C17 with a methyl or a benzyl or a methoxyl group generated pregnenolone derivatives that maintained a good level of antagonism of CB1 activity (Table 4A). Also a good level of activity was observed when position C20 is substituted with an alpha-hydroxyl group and/or the C5-C6 double bound was shifted to the C5-C4 position or was substituted with a beta-hydrogen in C5 (Table 4A). In contrast an ethyl group in position C17, the suppression of the ketone in position C20 or its substitution with a methylamino group profoundly reduced antagonism of CB1 activity (Table 4B). The suppression of the alcohol function in position C3 or its substitution with a fluor or an azide or a benzyloxyl group generated compounds with a good antagonism of CB1 activity (Table 4C). In contrast the substitution of the alcohol in C3 with a methoxyl group induced a profound decrease of CB1 activity (Table 4D). When the alcohol in C3 was substituted with a ketone there was also a general decrease in the antagonism of CB1 activity (Table 4E). However, the reduced activity of the compounds with a ketone in C3 could be ameliorated by modifications in position C5, C20 and C17. An alpha-hydroxyl group in position C20 and C17 or the replacement of the C5-C6 double bond with a beta-hydrogen in position C5 ameliorated the CB1 antagonists of the ketone compounds (Table 4E).

Discussion:

These converging data can be summarized as follow:

First, the general formula A allows producing derivatives of pregnenolone for which the transformation in active steroids derived by pregnenolone is limited. This formula is original because the ability of chemical modification of pregnenolone to reduce or not metabolism in downstream active steroids could not have been predicted by previous knowledge or by an expert of the art.

Second, the general formula I and/or II allows producing derivatives of pregnenolone that are able to inhibit the effects of CB1 activation in different system models: 1. food intake induced by THC in both mice and rats; 2. food intake induced by food restriction in mice; 3. Behaviors belonging to the cannabinoid tetrade induced by THC; 4. Increase in TNFalpha induced by LPS.

V. Inhibition of the Effects of CB1 Receptors Activation is Specific of Pregnenolone and does not Involve Downstream Metabolites Example 26: THC Increased Pregnenolone Concentrations in the Brain of Male Wistar Rats More than the Ones of Pregnenolone-Derived Downstream Active Steroids In this example the inventors show that administration of THC (3 mg/kg sc) to male Wistar rats induced over time a significant increase of some of the pregnenolone-derived steroids and in particular of allopregnanolone and epiallopregnanolone. However, the effect of THC on pregnenolone was of several orders of magnitude higher than any of the effects observed on the downstream steroid derived from pregnenolone (FIG. 1C-F).

When THC was administered at various doses to male Wistar rats, the inventors found that THC increased the concentrations of the pregnenolone downstream derived steroids, allopregnanolone and epialopregananolone, whilst there was no significant increase in testosterone and DHT. However, even after the highest dose of THC, the increase in the concentrations of the other steroids were much smaller than the ones observed for pregnenolone.

Example 27: THC Did not Increase Pregnenolone-Derived Downstream Active Steroids in Mice When THC was administered at various doses to male mice, a strong dose-dependent increase in pregnenolone concentrations was observed. However, in mice pregnenolone-derived downstream active steroids allopregnanolone and epialopregananolone, testosterone and DHT did not increase significantly in the brain.

Example 28: Doses of Pregnenolone that Inhibit Food Intake do not Increase the Concentrations of Pregnenolone-Derived Downstream Active Steroids in the Brain In this example the inventors studied the effects of the doses of pregnenolone (between 2 and 8 mg/kg) that were able to inhibit the effects of CB1 activation in mice. Pregnenolone injections between 2 and 8 mg/kg increased brain levels of pregnenolone; however they did not modify the concentrations of downstream metabolites, such as epiallopregnanolone and allopregnanolone in the brain of mice (FIG. 4).

Discussion

These converging data can be summarized as follow:

First, CB1 activation by THC administration in rats induces a much smaller increase in allopregnanolone and epiallopregnanolone than in pregnenolone. In mice, THC administration did not increase allopregnanolone and epiallopregnanolone significantly. Consequently the negative feed-back on the activity of the CB1, exercised by the endogenous increase in pregnenolone concentrations, which was studied in mice, cannot be due to a subsequent increase of downstream active steroids derived from pregnenolone.

Second, the exogenous administration of pregnenolone in the range of doses at which the inhibition by pregnenolone of the effect of CB1 activation were observed (2-8 mg/kig) in mice did not increase either allopregnanolone or epiallopregnanolone in the brain (FIG. 2). Consequently, the inhibition of the CB1 activity observed after pregnenolone administration cannot be attributed to a subsequent increase of downstream active steroids derived from pregnenolone.

Finally, derivatives of pregnenolone obtained following the formula I and/or II that cannot be transformed in pregnanolone and allopregnanolone and other downstream active steroids are still able to inhibit the effects of CB1 activation. Consequently, the inhibition of the CB1 receptor and/or the inhibition of CB1 effects observed after pregnenolone administration cannot be attributed to downstream active steroids derived from pregnenolone.

VI. Methods for Administering Pregnenolone without Inducing and Increase in Downstream Neuroactive Metabolites Example 39: Administration of Pregnenolone with Methods that Simulate a Slow Release Formulation Allow to Reduce the Metabolism in Down Stream Active Steroids Here the inventors exemplify a method to administer pregnenolone at doses that are able to inhibit the CB1 activation but that do not increase downstream neuroactive steroids.

The effects of pregnenolone administration on plasmatic levels of pregnenolone were compared (n=5 per group) when pregnenolone was administered subcutaneously (6 mg/kg) or by Alzet micro-osmotic pumps (Alzet Osmotis Pumps, Charles River, France, model 2006) that simulate an extended release formulations of pregnenolone. Thus, these mini pump implanted subcutaneously provide a steady release of pregnenolone. Two pregneolone concentrations were used 0.6 mg/kg/hour and 1 mg/kg/hour (10 times and six times lower than the dose administered subcutaneously). Although pregenonolone administration at 6 mg/kg subcutaneously in mice does not increase the concentration of allopregnenolone in the brain (FIG. 4) a significant increase in this downstream active steroid is observed in the plasma (FIG. 20). Pregnenonolone administered subcutaneously at 6 mg/kg increased the plasmatic levels of pregnenolone (around 100 ng/ml) but also induced an increase in allopregnanolone. The half life of pregnenolone administered subcutaneously was quite short (half an hour) and the increase in allopregnanolone was maintained over one hour (FIG. 20). On the contrary when pregnenolone was steadily administered through Alzet minipump at 0.6 mg/kg/hour, pregnenolone increased in the range of the maximum increase observed after the subcutaneous injection but did not increased allopregnanolone (FIG. 20). Also pregnenolone levels remained in the range of effective therapeutic doses over two weeks. Even when pregnenolone was administered at 1 mg/kg/hour which increased pregnenolone plasmatic concentrations at the double of what observed after 6 mg/kg allopregnanolone did not increase (FIG. 20).

Discussion

Pregnenolone has been described in previous documents as a method to treat psychiatric diseases certain type of inflammation and metabolic disorders and certain type of addiction and in particular nicotine addiction and alcohol. However in all this methods pregnenolone was used at high concentrations with the explicit goal to increase down stream neuroactive steroids to which the therapeutic effects of the administration of pregnenolone was attributed. Here we show that pregnenolone in itself without the involvement of down stream neuroactive steroids at doses much lower the ones used in previous documents can be useful to treat the pathologies that involve an activation of the CB1 receptors. In this context since pregnenolone has a very short half-life (approximately 30 min) extended release formulations can be useful in order to maintain pregnenolone levels in the therapeutic range. By simulating such formulations using Alzet minipump we show that a steady administration of pregnenolone at low hourly concentrations allow to reach two objectives: 1. Induce stable concentration of pregnenolone that are in the range of the ones able to block all the effects of CB1 activation (around 100 ng/ml); and 2. Reduce the increase in downstream active steroids such as allopregnanolone. These results then provide a methods, trough the use of extended release formulations of pregnenolone, to administer pregnenolone at low doses to treat diseases involving the CB1 taking advantage of the pharmacological effects of pregnenolone itself and reducing the unwanted effects of down stream steroids.

REFERENCES

Throughout this application, various references describe the state of the art to which this invention pertains. The disclosures of these references are hereby incorporated by reference into the present disclosure.

Aloyo V J, Berg K A, Clarke W P, Spampinato U, Harvey J A. Inverse agonism at serotonin and cannabinoid receptors. Prog Mol Biol Transl Sci. 2010; 91:1-40. Review.

Bab I, Zimmer A. Cannabinoid receptors and the regulation of bone mass. Br J. Pharmacol. 2008 January; 153(2): 182-8. Epub 2007 Dec. 10. Review.

Baker D et al "Endocannabinoids control spasticity in a multiple sclerosis model" FASEB Journal Vol. 15 pages 300-302 February 2001

Barutta F, Corbelli A, Mastrocola R, Gambino R, Di Marzo V, Pinach S, Rastaldi M P, Perin P C, Gruden G. Cannabinoid receptor 1 blockade ameliorates albuminuria in experimental diabetic nephropathy. Diabetes. 2010 April; 59(4):1046-54. Epub 2010 Jan. 12.

Bátkai S, Mukhopadhyay P, Harvey-White J, Kechrid R, Pacher P, Kunos G. Endocannabinoids acting at CB1 receptors mediate the cardiac contractile dysfunction in vivo in cirrhotic rats. Am J Physiol Heart Circ Physiol. 2007 September; 293(3):H1689-95. Epub 2007 Jun. 8.

Beardsley P M, Thomas B F, McMahon L R. Cannabinoid CB1 receptor antagonists as potential pharmacotherapies for drug abuse disorders. Int Rev Psychiatry. 2009 April; 21(2):134-42. Review.

Bell-Anderson K S, Aouad L, Williams H, Sanz F R, Phuyal J, Larter C Z, Farrell G C, Caterson I D. Coordinated improvement in glucose tolerance, liver steatosis and obesity-associated inflammation by cannabinoid 1 receptor antagonism in fat Aussie mice. Int J Obes (Lond). 2011 Mar. 8. [Epub ahead of print]

Bermudez-Silva F J, Viveros M P, McPartland J M, Rodriguez de Fonseca F. The endocannabinoid system, eating behavior and energy homeostasis: the end or a new beginning? Pharmacol Biochem Behav. 2010 June; 95(4): 375-82. Epub 2010 Mar. 27. Review. PubMed PMID: 20347862.

Bifulco M, Grimaldi C, Gazzerro P, Pisanti S, Santoro A. Rimonabant: just an antiobesity drug? Current evidence on its pleiotropic effects. Mol. Pharmacol. 2007 June; 71(6):1445-56. Epub 2007 Feb. 27. Review.

Caraceni P, Pertosa A M, Giannone F, Domenicali M, Grattagliano I, Principe A, Mastroleo C, Perrelli M G, Cutrin J, Trevisani F, Croci T, Bernardi M. Antagonism of the cannabinoid CB-1 receptor protects rat liver against ischaemia-reperfusion injury complicated by endotoxaemia. Gut. 2009 August; 58(8):1135-43. Epub 2009 Mar. 11.

Chien F Y, Wang R F, Mittag T W, Podos S M. "Effect of WIN 55212-2, a cannabinoid receptor agonist, on aqueous humor dynamics in monkey". Arch Ophthalmol. 2003 January; 121(1):87-90.

Comelli F, Bettoni I, Colombo A, Fumagalli P, Giagnoni G, Costa B. Rimonabant, a cannabinoid CB1 receptor antagonist, attenuates mechanical allodynia and counteracts oxidative stress and nerve growth factor deficit in diabetic mice. Eur J. Pharmacol. 2010 Jul. 10; 637(1-3): 62-9. Epub 2010 Apr. 14.

Cosenza-Nashat M A, Bauman A, Zhao M L, Morgello S, Suh H S, Lee S C. Cannabinoid Receptor Expression in HIV Encephalitis and HIV-associated Neuropathologic Comorbidities. Neuropathol Appl Neurobiol. 2011 Mar. 31. doi: 10.1111/j.1365-2990.2011.01177.x. [Epub ahead of print]

Domenicali M, Caraceni P, Giannone F, Pertosa A M, Principe A, Zambruni A, Trevisani F, Croci T, Bernardi M. Cannabinoid type 1 receptor antagonism delays ascites formation in rats with cirrhosis. Gastroenterology. 2009 July; 137(1):341-9. Epub 2009 Jan. 14

Gary-Bobo M, Elachouri G, Gallas J F, Janiak P, Marini P, Ravinet-Trillou C, Chabbert M, Cruccioli N, Pfersdorff C, Roque C, Amone M, Croci T, Soubrie P, Oury-Donat F, Maffrand J P, Scatton B, Lacheretz F, Le Fur G, Herbert J M, Bensaid M. Rimonabant reduces obesity-associated hepatic steatosis and features of metabolic syndrome in obese Zucker fa/fa rats. Hepatology. 2007 July; 46(1): 122-9.

Gaskari S A, Liu H, Moezi L, Li Y, Baik S K, Lee S S. Role of endocannabinoids in the pathogenesis of cirrhotic cardiomyopathy in bile duct-ligated rats. Br J. Pharmacol. 2005 October; 146(3):315-23.

Gazzerro P, Malfitano A M, Proto M C, Santoro A, Pisanti S, Caruso M G, Notarnicola M, Messa C, Laezza C, Misso G, Caraglia M, Bifulco M. Synergistic inhibition of human colon cancer cell growth by the cannabinoid CB1 receptor antagonist rimonabant and oxaliplatin. Oncol Rep. 2010 January; 23(1):171-5.

George, O., Vallee, M., Vitiello, S., Le Moal, M., Piazza, P. V., and Mayo, W. (2010). Low brain allopregnanolone levels mediate flattened circadian activity associated with memory impairments in aged rats. Biol. Psychiatry. 68, 956-963.

Hamamoto D T, Giridharagopalan S, Simone D A. Acute and chronic administration of the cannabinoid receptor agonist CP 55,940 attenuates tumor-evoked hyperalgesia. Eur J. Pharmacol. 2007 Mar. 8; 558(1-3):73-87. Epub 2006 Dec. 9.

Heller J E, Baty D E, Zhang M, Li H, Adler M, Ganea D, Gaughan J, Loftus C M, Jallo J I, Tuma R F. The combination of selective inhibition of the cannabinoid CB1 receptor and activation of the cannabinoid CB2 receptor yields improved attenuation of motor and autonomic deficits in a mouse model of spinal cord injury. Clin Neurosurg. 2009; 56:84-92.

Idris A I. Cannabinoid receptors as target for treatment of osteoporosis: a tale of two therapies. Curr Neuropharmacol. 2010 September; 8(3):243-53. Review.

Idris A I, van't H of R J, Greig I R, Ridge S A, Baker D, Ross R A, Ralston S H. Regulation of bone mass, bone loss and osteoclast activity by cannabinoid receptors. Nat. Med. 2005 July; 11(7):774-9. Epub 2005 May 22.

Jack D. A bright future for osteoporosis treatment. Drug News Perspect. 2005 June; 18(5):341-4.

Janiak P, Poirier B, Bidouard J P, Cadrouvele C, Pierre F, Gouraud L, Barbosa I, Dedio J, Maffrand J P, Le Fur G, O'Connor S, Herbert J M. Blockade of cannabinoid CB1 receptors improves renal function, metabolic profile, and increased survival of obese Zucker rats. Kidney Int. 2007 December; 72(11):1345-57. Epub 2007 Sep. 19.

Jourdan T, Djaouti L, Demizieux L, Gresti J, Vergés B, Degrace P. CB1 antagonism exerts specific molecular effects on visceral and subcutaneous fat and reverses liver steatosis in diet-induced obese mice. Diabetes. 2010 April; 59(4):926-34. Epub 2010 Jan. 28.

Lee H K, Choi E B, Pak C S. The current status and future perspectives of studies of cannabinoid receptor 1 antagonists as anti-obesity agents. Curr Top Med. Chem. 2009; 9(6):482-503. Review.

Lim S Y, Davidson S M, Yellon D M, Smith C C. The cannabinoid CB1 receptor antagonist, rimonabant, protects against acute myocardial infarction. Basic Res Cardiol. 2009 November; 104(6):781-92. Epub 2009 May 22.

Marsicano, G., Wotjak, C. T., Azad, S. C., Bisogno, T., Rammes, G., Cascio, M. G., Hermann, H., Tang, J., Hofmann, C., Zieglgansberger, W., Di, M., V, and Lutz, B. (2002). The endogenous cannabinoid system controls extinction of aversive memories. Nature. 418, 530-534.

Matsuda K, Mikami Y, Takeda K, Fukuyama S, Egawa S, Sunamura M, Maruyama I, Matsuno S. The cannabinoid 1 receptor antagonist, AM251, prolongs the survival of rats with severe acute pancreatitis. Tohoku J Exp Med. 2005 October; 207(2):99-107.

Martín-García E, Burokas A, Martín M, Berrendero F, Rubí B, Kiesselbach C, Heyne A, Gispert J D, Millán O, Maldonado R. Central and peripheral consequences of the chronic blockade of CB1 cannabinoid receptor with rimonabant or taranabant. J. Neurochem. 2010 March; 112(5):1338-13351. Epub 2009 Dec. 17.

Mallat A, Lotersztajn S. Endocannabinoids and their role in fatty liver disease. Dig Dis. 2010; 28(1):261-6. Epub 2010 May 7. Review.

Mendizabal, V., Zimmer, A., and Maldonado, R. (2006). Involvement of kappa/dynorphin system in WIN 55, 212-2 self-administration in mice. Neuropsychopharmacology. 31, 1957-1966.

Milligan G, Smith N J. Allosteric modulation of heterodimeric G-protein-coupled receptors. Trends Pharmacol Sci. 2007 December; 28(12):615-20. Epub 2007 Nov. 19. Review.

Mingorance C, de Sotomayor M A, Marhuenda E, Herrera M D. Chronic treatment with the cannabinoid 1 antagonist rimonabant altered vasoactive cyclo-oxygenase-derived products on arteries from obese Zucker rats. J Cardiovasc Pharmacol. 2010 November; 56(5):560-9.

Monory, K., Blaudzun, H., Massa, F., Kaiser, N., Lemberger, T., Schutz, G., Wotjak, C. T., Lutz, B., and Marsicano, G. (2007). Genetic dissection of behavioural and autonomic effects of Delta(9)-tetrahydrocannabinol in mice. PLoS. Biol. 5, e269.

Mukerji G, Yiangou Y, Agarwal S K, Anand P. Increased cannabinoid receptor 1-immunoreactive nerve fibers in overactive and painful bladder disorders and their correlation with symptoms. Urology. 2010 June; 75(6): 1514.e15-20. Epub 2010 Mar. 25.

Mukhopadhyay P, Bátkai S, Rajesh M, Czifra N, Harvey-White J, Haskó G, Zsengeller Z, Gerard N P, Liaudet L, Kunos G, Pacher P. Pharmacological inhibition of CB1 cannabinoid receptor protects against doxorubicin-induced cardiotoxicity. J Am Coll Cardiol. 2007 Aug. 7; 50(6):528-36. Epub 2007 Jul. 23.

Mukhopadhyay P, Pan H, Rajesh M, Bátkai S, Patel V, Harvey-White J, Mukhopadhyay B, Haskó G, Gao B, Mackie K, Pacher P. CB1 cannabinoid receptors promote oxidative/nitrosative stress, inflammation and cell death in a murine nephropathy model. Br J. Pharmacol. 2010 June; 160(3):657-68.

Mukhopadhyay P, Rajesh M, Bátkai S, Patel V, Kashiwaya Y, Liaudet L, Evgenov O V, Mackie K, Haskó G, Pacher P. CB1 cannabinoid receptors promote oxidative stress and cell death in murine models of doxorubicin-induced cardiomyopathy and in human cardiomyocytes. Cardiovasc Res. 2010 Mar. 1; 85(4):773-84. Epub 2009 Nov. 26.

Nissen S E, Nicholls S J, Wolski K, Rodés-Cabau J, Cannon C P, Deanfield J E, Després J P, Kastelein J J, Steinhubl S R, Kapadia S, Yasin M, Ruzyllo W, Gaudin C, Job B, Hu B, Bhatt D L, Lincoff A M, Tuzcu E M; STRADIVARIUS Investigators. Effect of rimonabant on progression of atherosclerosis in patients with abdominal obesity and coronary artery disease: the STRADIVARIUS randomized controlled trial. JAMA. 2008 Apr. 2; 299(13): 1547-60.

Pandey R, Hegde V L, Singh N P, Hofseth L, Singh U, Ray S, Nagarkatti M, Nagarkatti P S. Use of cannabinoids as a novel therapeutic modality against autoimmune hepatitis. Vitam Horm. 2009; 81:487-504. Review.

Pertwee R G. Inverse agonism and neutral antagonism at cannabinoid CB1 receptors. Life Sci. 2005 Feb. 4; 76(12): 1307-24. Epub 2004 Dec. 8. Review.

Pisanti S, Picardi P, Prota L, Proto M C, Laezza C, McGuire P G, Morbidelli L, Gazzerro P, Ziche M, Das A, Bifulco M. Genetic and pharmacological inactivation of cannabinoid CB1 receptor inhibits angiogenesis. Blood. 2011 Apr. 1.

Pryce G, Baker D "Control of Spasticity in a Multiple Sclerosis Model is mediated by CB1, not CB2, Cannabinoid Receptors" British Journal of Pharmacology Volume 150, Issue 4, pages 519-525, February 2007

Puighermanal, E., Marsicano, G., Busquets-Garcia, A., Lutz, B., Maldonado, R., and Ozaita, A. (2009). Cannabinoid modulation of hippocampal long-term memory is mediated by mTOR signaling. Nat. Neurosci. 12, 1152-1158.

Rinaldi-Carmona, M., Calandra, B., Shire, D., Bouaboula, M., Oustric, D., Barth, F., Casellas, P., Ferrara, P., and Le Fur, G. (1996). Characterization of two cloned human CB1 cannabinoid receptor isoforms. J Pharmacol Exp. Ther. 278, 871-878.

Rossi B, Zenaro E, Angiari S, Ottoboni L, Bach S, Piccio L, Pietronigro E C, Scarpini E, Fusco M, Leon A, Constantin G. Inverse agonism of cannabinoid CB1 receptor blocks the adhesion of encephalitogenic T cells in inflamed brain venules by a protein kinase A-dependent mechanism. J. Neuroimmunol. 2011 April; 233(1-2):97-105. Epub 2011 Jan. 7.

Santoro A, Pisanti S, Grimaldi C, Izzo A A, Borrelli F, Proto M C, Malfitano A M, Gazzerro P, Laezza C, Bifulco M. Rimonabant inhibits human colon cancer cell growth and reduces the formation of precancerous lesions in the mouse colon. Int J Cancer. 2009 Sep. 1; 125(5):996-1003.

Sarnataro D, Pisanti S, Santoro A, Gazzerro P, Malfitano A M, Laezza C, Bifulco M. The cannabinoid CB1 receptor antagonist rimonabant (SR141716) inhibits human breast cancer cell proliferation through a lipid raft-mediated mechanism. Mol. Pharmacol. 2006 October; 70(4):1298-306. Epub 2006 Jul. 5.

Soria, G., Castane, A., Ledent, C., Parmentier, M., Maldonado, R., and Valverde, O. (2006). The lack of A2A adenosine receptors diminishes the reinforcing efficacy of cocaine. Neuropsychopharmacology. 31, 978-987.

Soria, G., Mendizabal, V., Tourino, C., Robledo, P., Ledent, C., Parmentier, M., Maldonado, R., and Valverde, O. (2005). Lack of CB1 cannabinoid receptor impairs cocaine self-administration. Neuropsychopharmacology. 30, 1670-1680.

Sugamura K, Sugiyama S, Fujiwara Y, Matsubara J, Akiyama E, Maeda H, Ohba K, Matsuzawa Y, Konishi M, Nozaki T, Horibata Y, Kaikita K, Sumida H, Takeya M, Ogawa H. Cannabinoid 1 receptor blockade reduces atherosclerosis with enhances reverse cholesterol transport. J Atheroscler Thromb. 2010 Feb. 26; 17(2):141-7.

Sugamura K, Sugiyama S, Nozaki T, Matsuzawa Y, Izumiya Y, Miyata K, Nakayama M, Kaikita K, Obata T, Takeya M, Ogawa H. Activated endocannabinoid system in coronary artery disease and antiinflammatory effects of cannabinoid 1 receptor blockade on macrophages. Circulation. 2009 Jan. 6; 119(1):28-36. Epub 2008 Dec. 22.

Tam J, Vemuri V K, Liu J, Bátkai S, Mukhopadhyay B, Godlewski G, Osei-Hyiaman D, Ohnuma S, Ambudkar S V, Pickel J, Makriyannis A, Kunos G. Peripheral CB1 cannabinoid receptor blockade improves cardiometabolic risk in mouse models of obesity. J Clin Invest. 2010 Aug. 2; 120(8):2953-66. doi: 10.1172/JCI42551. Epub 2010 Jul. 26. Erratum in: J Clin Invest. 2010 Oct. 1; 120(10): 3735.

Tam J, Liu J, Mukhopadhyay B, Cinar R, Godlewski G, Kunos G. Endocannabinoids in liver disease. Hepatology. 2011 January; 53(1):346-55. doi: 10.1002/hep.24077. Review.

Vallee, M., Rivera, J. D., Koob, G. F., Purdy, R. H., and Fitzgerald, R. L. (2000). Quantification of neurosteroids in rat plasma and brain following swim stress and allopregnanolone administration using negative chemical ionization gas chromatography/mass spectrometry. Anal. Biochem. 287, 153-166.

Van Diepen H, Schlicker E, Michel M C. Prejunctional and peripheral effects of the cannabinoid CB(1) receptor inverse agonist rimonabant (SR 141716). Naunyn Schmiedebergs Arch Pharmacol. 2008 October; 378(4): 345-69. Epub 2008 Jul. 25. Review.

Wang X, Horswill J G, Whalley B J, Stephens G J. Effects of the Allosteric Antagonist 1-(4-Chlorophenyl)-3-[3-(6-pyrrolidin-1-ylpyridin-2-yl)phenyl]urea (PSNCBAM-1) on CB1 Receptor Modulation in the Cerebellum. Mol. Pharmacol. 2011 April; 79(4):758-67. Epub 2010 Dec. 28.

Xie S, Furjanic M A, Ferrara J J, McAndrew N R, Ardino E L, Ngondara A, Bernstein Y, Thomas K J, Kim E, Walker J M, Nagar S, Ward S J, Raffa R B. The endocannabinoid system and rimonabant: a new drug with a novel mechanism of action involving cannabinoid CB1 receptor antagonism—or inverse agonism—as potential obesity treatment and other therapeutic use. J Clin Pharm Ther. 2007 June; 32(3):209-31. Review.

Zheng D, Bode A M, Zhao Q, Cho Y Y, Zhu F, Ma W Y, Dong Z. The cannabinoid receptors are required for ultraviolet-induced inflammation and skin cancer development. Cancer Res. 2008 May 15; 68(10):3992-8.

Zyromski N J, Mathur A, Pitt H A, Wade T E, Wang S, Swartz-Basile D A, Prather A D, Lillemoe K D. Cannabinoid receptor-1 blockade attenuates acute pancreatitis in obesity by an adiponectin mediated mechanism. J Gastrointest Surg. 2009 May; 13(5):831-8. Epub 2009 Feb. 19.

The invention claimed is:

1. A pregnenolone derivative wherein said pregnenolone derivative is 17α-Benzyl-3β-fluoropregnenolone, 17α-Benzyl-3β-benzyloxypregnenolone, 3β-Benzyloxy-17α-methylpregnenolone, 17α-Benzylpregnenolone, 3β-Methoxy-17α-methylpregnenolone, 17α-Allyl-3β-methoxypregnenolone or 17α-Benzyl-3β-methoxypregnenolone.

2. A pharmaceutical composition comprising a pregnenolone derivative according to claim 1 and a pharmaceutically acceptable carrier.

* * * * *

UNITED STATES PATENT AND TRADEMARK OFFICE
CERTIFICATE OF CORRECTION

PATENT NO. : 10,150,793 B2
APPLICATION NO. : 14/118420
DATED : December 11, 2018
INVENTOR(S) : Piazza et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 681 days.

Signed and Sealed this
Twenty-fourth Day of November, 2020

Andrei Iancu
*Director of the United States Patent and Trademark Office*